US008772197B2

(12) United States Patent
Hatton et al.

(10) Patent No.: US 8,772,197 B2
(45) Date of Patent: Jul. 8, 2014

(54) COMPOSITIONS FOR CHEMICAL AND BIOLOGICAL DEFENSE

(75) Inventors: Trevor Alan Hatton, Sudbury, MA (US); Lev E. Bromberg, Swampscott, MA (US); Huan Zhang, Falls Church, VA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1178 days.

(21) Appl. No.: 12/672,611

(22) PCT Filed: Aug. 18, 2008

(86) PCT No.: PCT/US2008/073460
§ 371 (c)(1),
(2), (4) Date: May 17, 2010

(87) PCT Pub. No.: WO2009/055128
PCT Pub. Date: Apr. 30, 2009

(65) Prior Publication Data
US 2011/0027869 A1 Feb. 3, 2011

Related U.S. Application Data

(60) Provisional application No. 60/956,517, filed on Aug. 17, 2007.

(51) Int. Cl.
*B01J 20/22* (2006.01)

(52) U.S. Cl.
USPC ............................ 502/401; 502/439; 502/526

(58) Field of Classification Search
USPC .......................................... 502/401, 439, 526
See application file for complete search history.

(56) References Cited

U.S. PATENT DOCUMENTS

| | | |
|---|---|---|
| 2,933,453 A | 4/1960 | Burks, Jr. |
| 3,061,469 A | 10/1962 | Manowitz et al. |
| 3,382,095 A | 5/1968 | Haluska |
| 3,413,077 A | 11/1968 | Bertin et al. |
| 3,505,306 A | 4/1970 | Kazan, Jr. et al. |
| 3,960,477 A | 6/1976 | Harper, Jr. et al. |
| 4,201,822 A | 5/1980 | Cowsar |
| 4,263,305 A | 4/1981 | Epstein et al. |
| 4,352,810 A | 10/1982 | Benschop et al. |
| 4,502,479 A | 3/1985 | Garwood et al. |
| 4,612,016 A | 9/1986 | Jaeger et al. |
| 4,780,102 A | 10/1988 | Harper, Jr. |
| 4,784,699 A | 11/1988 | Cowsar et al. |
| 5,164,253 A | 11/1992 | Greak |
| 5,242,466 A | 9/1993 | Aseervatham et al. |
| 5,262,192 A | 11/1993 | Nelson et al. |
| 5,268,004 A | 12/1993 | Greak |
| 5,276,125 A | 1/1994 | Pedain et al. |
| 5,326,585 A | 7/1994 | Nelson et al. |
| 5,364,411 A | 11/1994 | Beretta et al. |
| 5,501,711 A | 3/1996 | Weltrowski et al. |
| 5,578,088 A | 11/1996 | Schrell et al. |
| 5,634,949 A | 6/1997 | Hohmann et al. |
| 5,652,049 A | 7/1997 | Suzuki |
| 5,667,533 A | 9/1997 | Hauser et al. |
| 5,695,750 A | 12/1997 | Doctor et al. |
| 5,766,687 A | 6/1998 | Rappoport |
| 5,823,978 A | 10/1998 | Cueman et al. |
| 5,830,539 A | 11/1998 | Yan et al. |
| 5,939,198 A | 8/1999 | Howard, Jr. et al. |
| 5,977,014 A | 11/1999 | Plischke et al. |
| 5,980,620 A | 11/1999 | Brodie et al. |
| 6,087,448 A | 7/2000 | Mitchell et al. |
| 6,229,062 B1 | 5/2001 | Mandell et al. |
| 6,361,696 B1 | 3/2002 | Spiegelman et al. |
| 6,497,733 B1 | 12/2002 | Ware, Jr. et al. |
| 6,534,554 B1 | 3/2003 | Mitchell et al. |
| 6,566,574 B1 | 5/2003 | Tadros et al. |
| 6,569,353 B1 | 5/2003 | Giletto et al. |
| 6,706,092 B2 | 3/2004 | Rohrbach et al. |
| 6,723,890 B2 | 4/2004 | Tucker et al. |
| 6,746,491 B2 | 6/2004 | Lack |
| 6,825,138 B2 | 11/2004 | Lack |
| 6,833,075 B2 | 12/2004 | Hughes |
| 6,895,871 B1 | 5/2005 | Smith et al. |
| RE39,246 E | 8/2006 | Putzig |
| 7,138,356 B2 | 11/2006 | Putzig |
| 7,141,518 B2 | 11/2006 | MacDonald et al. |
| 2002/0104169 A1 | 8/2002 | Sivik et al. |

(Continued)

FOREIGN PATENT DOCUMENTS

| | | |
|---|---|---|
| DE | 28 44 667 | 4/1980 |
| EP | 0 906 773 | 4/1999 |
| RU | 1 630 276 | 1/1998 |

OTHER PUBLICATIONS

International Search Report dated Jul. 7, 2009 from PCT/US2008/073460.
Ladziata et al., "Facile Preparation and Reactivity of Polymer-Supported N-(2-Iodylphenyl)-acylamide, an Efficient Oxidizing System," Organic Letters, 8(1):167-170 (2006).
Lei et al., "A facile route to a polymer-supported IBX reagent," Tetrahadron Letters, 44(8):1635-1637 (2003).
Morales-Rojas et al., "Phosphorolytic Reactivity of o-Iodosylcarboxylates and Related Nucleophiles," Chem. Rev., 102(7):2497-2521 (2002).
Moss et al., "An Efficient Iodosobenzoate-Functionalized Polymer for the Cleavage of Reactive Phosphates," Langmuir, 6(10):1614-1616 (1990).

(Continued)

*Primary Examiner* — Edward Johnson
(74) *Attorney, Agent, or Firm* — Foley Hoag LLP

(57) ABSTRACT

One aspect of the present invention relates to reactive compositions and methods of use thereof, wherein a metal oxide cluster is used to connect a reactive group (or groups) to the surface of a substrate. In certain embodiments, the reactive group in the compositions decomposes organophosphate agents through nucleophilic hydrolysis. In certain embodiments, the reactive group in the compositions is bactericidal. Remarkably, the use of metal oxide clusters in the disclosed compositions and methods permits incorporation of higher quantities of nucleophilic and bactericidal groups without the difficulties associated with having to pretreat the substrate prior to its association with the reactive groups.

20 Claims, 47 Drawing Sheets

(56) References Cited

U.S. PATENT DOCUMENTS

| | | |
|---|---|---|
| 2004/0009726 A1 | 1/2004 | Axtell et al. |
| 2004/0121077 A1 | 6/2004 | Park et al. |
| 2004/0266641 A1 | 12/2004 | Gentschev et al. |
| 2005/0101211 A1 | 5/2005 | Ramkumar |
| 2005/0109981 A1 | 5/2005 | Tucker et al. |
| 2005/0129914 A1 | 6/2005 | Rim et al. |
| 2005/0215425 A1 | 9/2005 | Clair et al. |
| 2005/0215426 A1 | 9/2005 | Putzig |
| 2006/0030691 A1 | 2/2006 | Putzig |
| 2006/0040388 A1 | 2/2006 | Bromberg et al. |
| 2006/0051266 A1 | 3/2006 | Green et al. |
| 2006/0089611 A1 | 4/2006 | Herfert et al. |
| 2006/0148104 A1 | 7/2006 | Marini et al. |
| 2006/0157513 A1 | 7/2006 | Solomon |
| 2006/0172133 A1 | 8/2006 | Naasani |
| 2006/0254427 A1 | 11/2006 | Trend et al. |
| 2007/0048175 A1 | 3/2007 | Tichy et al. |
| 2007/0065822 A1 | 3/2007 | Hastwell et al. |

OTHER PUBLICATIONS

Moss et al., "Efficient Catalytic Cleavage of Reactive Phosphates by an o-Iodosobenzoate Functionalized Surfactant," J. Am. Chem. Soc., 108(4):788-793 (1986).

Moss et al., "Immobilized Iodosobenzoate Catalysts for the Cleavage of Reactive Phosphates," J. Org. Chem., 55(7):2064-2069 (1990).

Moss et al., "Iodosobenzoate-Microemulsion Reagents for the Cleavage of a Reactive Phosphate," Langmuir, 9(11):2902-2906 (1993).

Moss et al., "Kinetics of Cleavage of Thiophosphates and Phosphonothioates by Micellar Iodosocarboxylates and Copper Metallomicelles," Langmuir, 16(16):6485-6491 (2000).

Moss et al., "Polymer-Bound Iodosobenzoate Reagents for the Cleavage of Reactive Phosphates," Tetrahedron Letters, 29(20):2433-2436 (1988).

Moss et al., "Silica Functionalized With Iodosobenzoate for the Catalytic Cleavage of Reactive Phosphates," J. Chem. Soc., Perkin Trans. 1, 1350-1352 (1989).

Mülbaier et al., "The Synthesis and Oxidative Properties of Polymer-Supported IBX," Angew. Chem. Int. Ed. Engl., 40(23):4393-4394 (2001).

Panetta et al., "Synthesis of 4-Alkyl-2-iodosobenzoic Acids: Potent Catalysts for the Hydrolysis of Phosphorus Esters," J. Org. Chem., 55(18):5202-5205 (1990).

Reed et al., "Preparation of Soluble and Insoluble Polymer Supported IBX Reagents," Bioorg. Med. Chem. Lett., 12(15):2047-2049 (2002).

Sorg et al., "Oxidizing Polymers: A Polymer-Supported, Recyclable Hypervalent Iodine(V) Reagent for the Efficient Conversion of Alcohols, Carbonyl Compounds, and Unsaturated Carbamates in Solution," Angew. Chem. Int. Ed., 40(23):4395-4397 (2001).

Sakuratani, K., "Polymer-Supported Hypervalent Iodine Reagents," Synlett, 12:1966-1975 (2002).

Figure 12
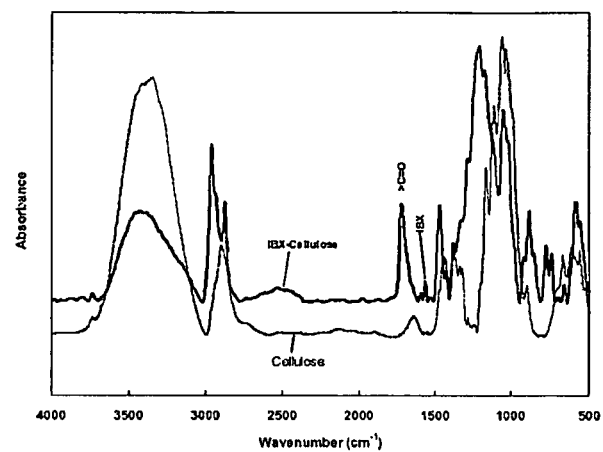
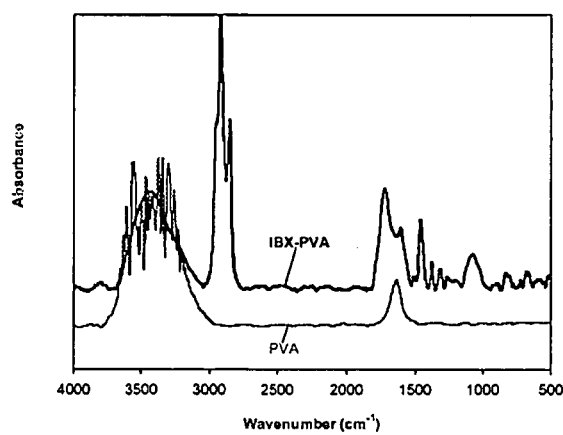

Figure 17

| Medium | Species (conditions) | $t_{1/2}$ (h) | $k"$ ($M^{-1}s^{-1}$) | Reference |
|---|---|---|---|---|
| IBX-PVA in water | CP (25°C, pH 7.4)<br>CPO (25°C, pH 7.4) | 6.42<br>2.49 | $2.5 \times 10^{-2}$<br>$1.1 \times 10^{-1}$ | Present work |
| PVA in water | CP (25°C, pH 7.4)<br>CPO (25°C, pH 7.4) | 727<br>27.7 | | Present work |
| IBX-Cellulose in water | CP (25°C, pH 7.4) | 27.7 | $9.9 \times 10^{-3}$ | Present work |
| Cellulose in water | CP (25°C, pH 7.4) | 727 | | Present work |
| Water | CP (40°C, pH 8) | 269 | | Noblet et al. 1996, *3685*. |
| Water | CP (25°C, pH 9) | 85 | | Duirk et al. 2006, *546*. |
| HOCl aqueous solution | CP (25°C, pH 7.5)<br>CPO (25°C, pH 6.3) | $<10^{-3}$<br>$<10^{-3}$ | 140<br>420 | Duirk et al. 2006, *546*. |
| Red brown earth, 16% water | CP (25°C, pH 7.1) | $(7-11) \times 10^3$ | | Baskaran et al. 1999, *1222*. |
| Human blood | CP (37°C, pH 7.4)<br>CPO (37°C, pH 7.4) | >3 h<br>$1.5 \times 10^{-2}$ | | Brzak et al. 1998, *203*. |

Figure 24
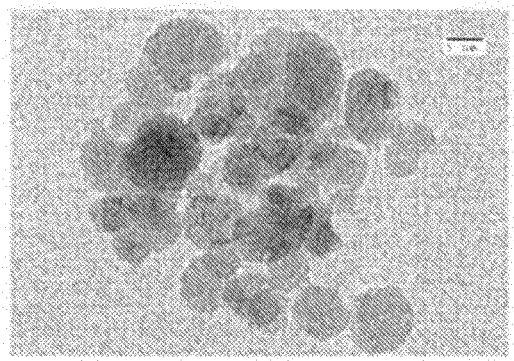
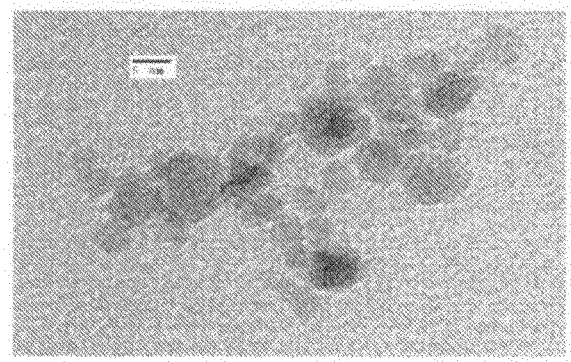

Figure 47
(a)
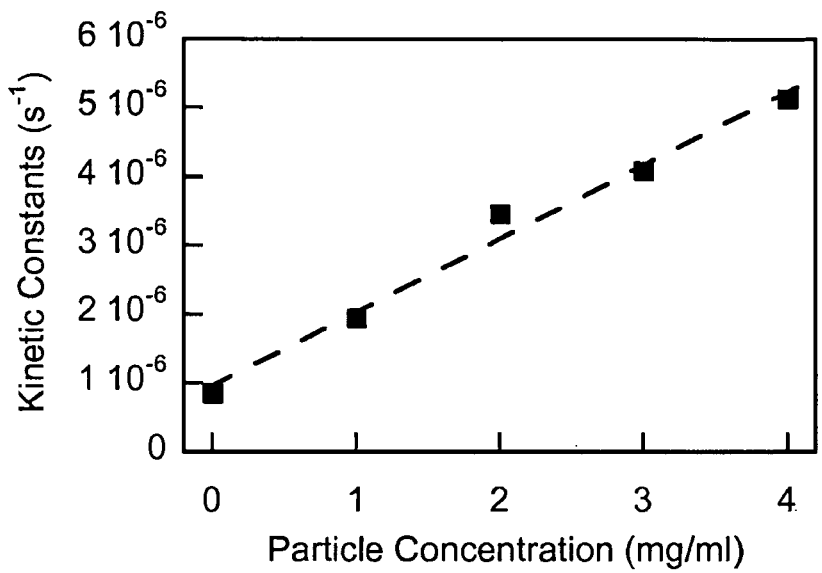
(b)
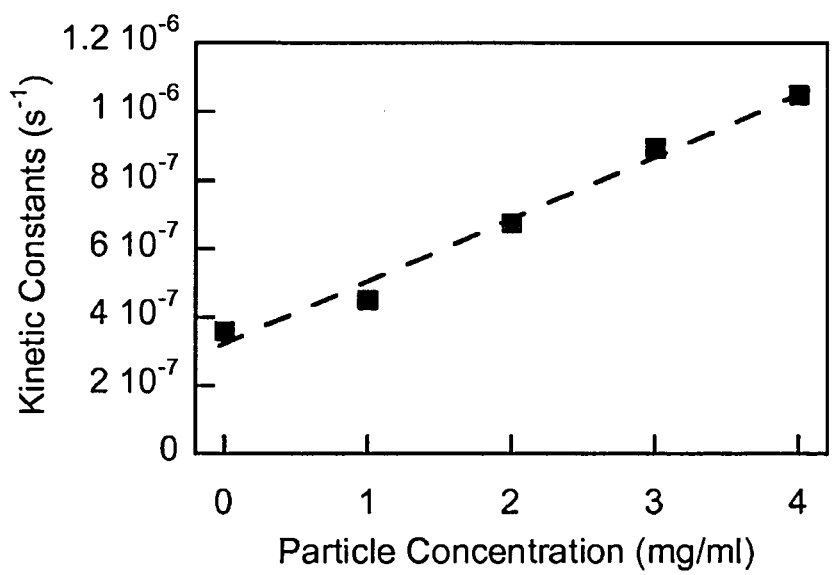

COMPOSITIONS FOR CHEMICAL AND BIOLOGICAL DEFENSE

RELATED APPLICATIONS

This application is the U.S. National Stage of International Patent Application No. PCT/US2008/073460, filed Aug. 18, 2008, which claims the benefit of priority to U.S. Provisional Patent Application Ser. No. 60/956,517, filed Aug. 17, 2007; both of which are hereby incorporated by reference in their entireties.

GOVERNMENT SUPPORT

This invention was made with government support under grant W911NF-07-1-0139was awarded by the Army Research Office. The government has certain rights in this invention.

BACKGROUND OF THE INVENTION

The presence of organophosphate esters (OPEs) in industrial and agricultural drain waters, spills, runoffs, and drifts, as well as OPE agent-based chemical munitions that may be released during warfare or a terrorist attack, poses great risks to human health and the environment. The worldwide number of exposures to OPEs in pesticides and insecticides is estimated at some 3,000,000 per year; the resulting total number of deaths and casualties is estimated at over 300,000 per year. Eyer, P. "The role of oximes in the management of organophosphorus pesticide poisoning," *Toxicol Rev.* 2003, 22(3), 165-190. Numerous OPE-based pesticides, insecticides and warfare agents, such as sarin, soman, and VX, in addition to being carcinogenic, act as nerve poisons which may cause cumulative damage to the nervous system and liver. The primary mechanism of action of the OPEs is irreversible inhibition of acetylcholinesterases; essential enzymes for breaking down acetylcholine and maintaining normal nerve function, resulting in the accumulation of the neurotransmitter acetylcholine at nerve synapses. Structures of the nerve poison sarin and a model analogue used in this study, diisopropyl fluorophosphate (DFP), are given in FIG. 1. The acute toxicity of various pentavalent organophosphorus (OP) compounds toward living species has resulted in the widespread use of phosphoric, thiophosphoric, and phosphonothioic acid derivatives as biocides for animal and crop protection as well as in the development of chemical weapons of mass destruction. Quin, L. D. A Guide to Organophosphorus Chemistry; Wiley: New York, 2000; Compton, J. A. Military Chemical and Biological Agents; Telford Press: NJ, 1997; p 135; Gallo, M. A.; Lawryk, N.J. Organic Phosphorus Pesticides. The Handbook of Pesticide Toxicology; Academic Press: San Diego, Calif., 1991; Sultatos, L. G., *J. Toxicol. Environ. Health,* 1994, 43(3), 271-289; Morales-Rojas, H.; Moss, R. A., *Chem. Rev,* 2002, 102(7), 2497-2522. Development of an economical strategy for dealing with possible OP contamination is critical.

Some of the first OPE-decontaminating agents were oxidizers, such as bleaching powders. See Yang, Y. C. et al. "Decontamination of chemical warfare agents," *Chem. Rev.* 1992, 92(8), 1729-1743. However, the activity of bleaches decreases upon long-term storage; therefore, to have the desired effect, copious amounts of bleach must be used. Moreover, because bleaches are corrosive, they are not compatible with many surfaces.

At present, the decontamination solutions of choice are DS-2 (a non-aqueous liquid composed of diethylenetriamine, ethylene glycol, monomethyl ether, and sodium hydroxide) and STB (super tropical bleach). Although DS-2 is generally not corrosive to metal surfaces, it damages skin, paints, plastics, rubber, and leather materials. STB, while effective, has the same environmental problems as bleaches and cannot be used on the skin. Consequently, personal decontamination equipment typically consists of packets of wipes containing such chemicals as sodium hydroxide, ethanol, and phenol. These chemicals are selected to provide a nucleophilic attack at the phosphorous atom of nerve agents.

Efforts aimed at alternatives to oxidizers have focused on the development of processes for the catalytic destruction (CD) of nerve agents and pesticides. Chiron, S. et al. "Pesticide chemical oxidation: state-of-the-art," *Water Research* 2000, 34(2), 366-377; and Russell, A. J. et al. "Biomaterials for mediation of chemical and biological warfare agents," *Annu. Rev. Biomed. Eng.* 2003, 5, 1-27. It was first recognized in the 1950s that certain metal ions, especially Cu(II), had the ability to catalyze the hydrolysis of nerve agents and their stimulants. The catalytic activity of such chemicals was significantly enhanced when Cu(II) was bound to certain ligands. For example, diisopropyl phosphorofluoridate (DFP) has a hydrolytic half-life of approximately 2 days in water, 5 hours in water when $CuSO_4$ is added, and just 8 minutes in water when Cu(II) bound to either histidine or N,N'-dipyridyl is added in an approximately 2:1 ratio of metal complex to substrate. Sarin was found to be even more susceptible to metal-based catalysis with a half-life of only 1 minute in the presence of tetramethyl-EDA-Cu(II) complex (1:1 metal complex to substrate). However, the use of free copper-ligand complexes for catalyzing the degradation of nerve agents also has disadvantages. First, the nerve agent must be brought into contact with a solution of the metal-ion-containing catalyst. Second, the ratio of metal to chelate must be carefully controlled. Third, solubility issues can still limit the pH range and choice of chelates for use in a particular environment. Catalytic hydrolysis is an important step in the detoxification of insecticides and chemical warfare agents; reactions show high specificity and dramatically enhanced rates.

In addition, researchers have begun to look at enzymes stabilized by attachment to a polymeric support as catalysts for the degradation of nerve agents. These enzymes, variously known as organophosphorous acid anhydrases, phosphotriesterases, sarinase, or others, are extracted either from microorganisms, such as *Pseudomonas diminuta*, or from squid. The enzymatic approach shows promise but is limited by the specificity of the proteins for their substrates, e.g., a parathion hydrolase would not be effective against another nerve agent. Further, the enzymes require a very specific range of conditions, e.g., pH, to function properly. In addition, field conditions can involve concentrated solutions of nerve agents, which can overwhelm the relatively low concentration of enzymes, which can be immobilized on a support.

The shortcomings of the free metal-ligand complexes and enzymatic approaches has caused the majority of the practical catalytic destruction technologies to focus on acid-catalyzed or base-catalyzed hydrolysis or nucleophile-aided hydrolysis. Magee, R. S. "U.S. chemical stockpile disposal program: the search for alternative technologies. In Effluents From Alternative Demilitarization Technologies," ed. F W Holm, Dordrecht: Kluwer Acad., 1998, 22, 112; Amos, D.; Leake, B. "Clean-up of chemical agents on soils using simple washing or chemical treatment processes," *J. Hazard. Mater.* 1994, 39, 107-117; Yang, Y. C. "Chemical detoxification of nerve agent," *Acc. Chem. Res.* 1999, 32, 109-15; and Yang, Y. C.; Baker, J. A.; Ward, J. R. "Decontamination of chemical warfare agents," *Chem. Rev.* 1992, 92(8), 1729-1743. In this regard, α-nucleophiles, such as hydroperoxides, hypochlorite, iodosocarboxylates, hydroxamates, and oximates, have been investigated alone or in concert with surfactants. Wagner, G. W.; Yang, Y.-C. "Rapid Nucleophilic/Oxidative Decontamination of Chemical Warfare Agents," *Ind. Eng. Chem. Res.* 2002, 41(8), 1925-1928; Moss, R. A.; Chung, Y. C. "Immobilized iodosobenzoate catalysts for the cleavage of reactive phosphates," *J. Org. Chem.* 1990, 55(7), 2064-2069; and Fanti, M.; Mancin, F.; Tecilla, P.; Tonellato, U. "Ester Cleavage Catalysis in Reversed Micelles by Cu(II) Complexes of Hydroxy-Functionalized Ligands," *Langmuir* 2000, 16(26), 10115-10122. However, very few reagents are currently available that are both inexpensive and non-toxic as well as catalytic. Rather, most of these compounds show only stoichiometric dephosphorylating activities at neutral pH. Bhattacharya, S.; Snehalatha, K. "Evidence for the Formation of Acylated or Phosphorylated Monoperoxyphthalates in the Catalytic Esterolytic Reactions in Cationic Surfactant Aggregates," *J. Org. Chem.* 1997, 62(7), 2198-2204. Notable exceptions include micellar iodosobenzoate, and related derivatives, micelle-forming metallocomplexes, and immobilized metal chelate complexes. Moss, R. A.; Chung, Y. C. "Immobilized iodosobenzoate catalysts for the cleavage of reactive phosphates," *J. Org. Chem.* 1990, 55(7), 2064-2069; Menger, F. M.; Gan, L. H.; Johnson, E.; Durst, D. H. "Phosphate ester hydrolysis catalyzed by metallomicelles," *J. Amer. Chem. Soc.* 1987, 109(9), 2800-2803; and Chang et al. (US 2003/0054949 A1). Most studies have concentrated on homogeneous or micellar catalysts, which do not afford the advantages of catalyst recycle. Additionally, operational cost and environmental footprint are always a concern.

Magnetic nanoparticles have attracted attention for possible applications to biological and environmental separations because they permit fast and economical removal of target compounds from complex media by use of magnetic fields. Magnetite nanoparticles are most commonly utilized and often prepared by co-precipitation of Fe(II) and Fe(III) salts in water. The procedure is simple and can be run on a large scale with "off the shelf" raw materials. Magnetic nanoparticles may also be functionalized by reactive groups and used as catalysts. Because the particles are small, the surface area per unit volume is high and mass transfer resistances are small.

Even given the advances discussed above, destruction of stockpiled chemical weapons and OPE biocides accumulated in the biosphere by environmentally friendly means remains challenging, calling for continuing development. Singh B K, Walker A. "Microbial degradation of organophosphorus compounds" *FEMS Microbiol Rev.* 2006, 30(3), 428-471; Russell A J, Berberich J A, Drevon G F, Koepsel R R. "Biomaterials for mediation of chemical and biological warfare agents," *Annu Rev Biomed Eng.* 2003, 5, 1-27; Raushel F M. "Bacterial detoxification of organophosphate nerve agents," *Curr Opin Microbiol.* 2002, 5(3), 288-295. As mentioned above, chemical means of OP decomposition by hydrolysis or oxidation are among the common decontamination techniques. Acid- or base-catalyzed hydrolysis or nucleophile-aided hydrolysis enable highly specific and efficient pathways of the OP decontamination. Magee, R. S. "U.S. chemical stockpile disposal program: the search for alternative technologies. In: Effluents From Alternative Demilitarization Technologies," Holm, F. W., editor, Dordrecht: Kluwer Acad. 1998, 22, 112; Amos, D., Leake, B. "Clean-up of chemical agents on soils using simple washing or chemical treatment processes," *J. Hazard. Mater.* 1994, 39, 107-117; Yang, Y. C. "Chemical detoxification of nerve agent," *Acc. Chem. Res.* 1999, 32, 109-115; Yang, Y. C.; Baker, J. A.; Ward, J. R. "Decontamination of chemical warfare agents," *Chem. Rev.* 1992, 92(8), 1729-1743; Wagner, G. W., Yang, Y.-C., "Rapid nucleophilic/oxidative decontamination of chemical warfare agents," *Ind. Eng. Chem. Res.* 2002, 41(8), 1925-1928; Moss, R. A., Chung, Y. C. "Immobilized iodosobenzoate catalysts for the cleavage of reactive phosphates," *J. Org. Chem.* 1990, 55(7), 2064-2069; Fanti, M., Mancin, F., Tecilla, P., Tonellato, U., "Ester cleavage catalysis in reversed micelles by Cu(II) complexes of hydroxy-functionalized ligands," *Langmuir* 2000, 16(26), 10115-10122.

Interestingly, hypervalent iodine carboxylates, such as 2-iodoxybenzoic acid (IBX, 1-hydroxy-1,2-benziodoxol-3 (1H)-one 1-oxide) and o-iodoso- or iodosylbenzoic acid (IBA) (Scheme 1) and their tautomers and derivatives, have attracted increasing interest because of their selective, mild, and environmentally friendly properties in organic reactions, such as oxidation of alcohols into carbonyl compounds, oxidation of thiols to disulfides, single electron-transfer agents in cyclization of unsaturated amines to heterocycles and amides to γ-lactams, cleavage of oximes and hydrazones into the corresponding carbonyl compounds, etc. E. B. Merkushev, "Organic Compounds of Polyvalent Iodine—Derivatives of Iodosobenzene," *Russ. Chem. Rev.* 1987, 56 (9), 826-845; A. Varvoglis, "Hypervalent Iodine in Organic Synthesis," Academic Press, San Diego (1997); Wirth, T. "IBX-new reactions with an old reagent," *Angew. Chem. Int. Ed.* 2001, 40(15), 2812-2814.

Compounds classified as α-nucleophiles have strong hydrolytic reactivity, excellent chemical stability in the targeted complex systems, and relatively straightforward preparations. For example, hypervalent iodine carboxylates are very reactive α-nucleophiles due to the large electron density on the exocyclic oxygen and the short endocyclic I—O bond capable of attacking electrophilic P—O centers in the OPE compounds. Morales-Rojas, H.; Moss, R. A. "Phosphorolytic Reactivity of o-Iodosylcarboxylates and Related Nucleophiles," *Chem. Rev.* 2002, 102(7), 2497-2522.

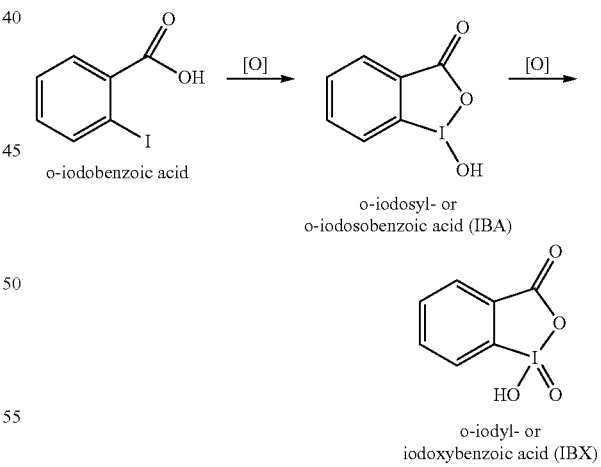

Moss and co-workers exploited the nucleophilic reactivity of hypervalent iodine carboxylates for the degradation of organophosphorus substrates. Moss, R. A., Chung, Y. C. "Immobilized iodosobenzoate catalysts for the cleavage of reactive phosphates," *J. Org. Chem.* 1990, 55(7), 2064-2069; R. A. Moss, H. Morales-Rojas, "Kinetics of Cleavage of Thiophosphates and Phosphonothioates by Micellar Iodosocarboxylates and Copper Metallomicelles," *Langmuir* 2000, 16(16), 6485-6491; Morales-Rojas, H.; Moss, R. A. "Phosphorolytic Reactivity of o-Iodosylcarboxylates and Related Nucleophiles," Chem. Rev. 2002, 102(7), 2497-2522. Furthermore, it has been shown that reactivity of these agents can be improved by the reactant incorporation into the self-assembled colloids, such as surfactant micelles. Moss, R. A.; Morales-Rojas, H. Langmuir 2000, 16, 6485; Moss, R. A.; Kim, K. Y.; Swarup, S. J. Am. Chem. Soc. 1986, 108, 788; Morales-Rojas, H.; Moss, R. A. "Phosphorolytic Reactivity of o-Iodosylcarboxylates and Related Nucleophiles," Chem. Rev. 2002, 102(7), 2497-2522. The rate enhancements observed in these aggregated systems are primarily due to the increases in the concentrations of reactants in the small interfacial volumes in which the reactions occur. Over the years, powerful reagents for the chemical degradation of the OPE compounds were created via syntheses of iodoso-modified surfactants and hydrophobic iodosocarboxylates with enhanced binding to the micellar pseudophase. C. A. Panetta, S. M. Garlick, H. Dupont Durst, F. R. Longo, J. R. Ward "Synthesis of 4-alkyl-2-iodosobenzoic acids: potent catalysts for the hydrolysis of phosphorus esters," J. Org. Chem. 1990, 55(18), 5202-5205; R. A. Moss, R. Fujiyama, H. Zhang, Y. C. Chung, K. McSorley "Iodosobenzoate-microemulsion reagents for the cleavage of a reactive phosphate," Langmuir 1993, 9(11), 2902-2906; Moss, R. A.; Morales-Rojas, H. "Kinetics of Cleavage of Thiophosphates and Phosphonothioates by Micellar Iodosocarboxylates and Copper Metallomicelles," Langmuir 2000, 16(16), 6485-6491; R. A. Moss, K. Y. Kim, S. Swamp "Efficient catalytic cleavage of reactive phosphates by a functionalized o-iodosobenzoate surfactant," J. Am. Chem. Soc. 1986, 108(4), 788-793. Polymers modified with covalently attached iodosobenzoate groups have also been synthesized for the purpose of creating solid decontaminates and were reported to be capable of inducing the cleavage of the P—O bond. Moss, R. A.; Bolikal, D.; Durst, H. D.; Hovanec, J. W. Tetrahedron Lett. 1988, 29, 2433; Moss, R. A.; Chung, Y.-C.; Durst, H. D.; Hovanec, J. W. J. Chem. Soc. Perkin Trans. 1 1989, 1350; Moss, R. A.; Chung, Y.-C. J. Org. Chem. 1990, 55, 2064; R. A. Moss, Y.-C. Chung "An Efficient Iodosobenzoate-Functionalized Polymer for the Cleavage of Reactive Phosphates" Langmuir 1990, 6, 1614-1616. Polymer-supported iodoxybenzoic acid has also been utilized as a reagent for alcohol oxidation and OP hydrolysis. Mulbaier, M., Giannis, A., "The synthesis and oxidative properties of polymer-supported IBX," Angew. Chem. Int. Ed. 2001, 40(23), 4393-4394; Z. Lei, C. Denecke, S. Jegasothy, D. C. Sherrington, N. K. H. Slater and A. J. Sutherland, "A facile route to a polymer-supported IBX reagent," Tetrahedron Lett. 2003, 44(8), 1635-1637; Morales-Rojas, H.; Moss, R. A. "Phosphorolytic Reactivity of o-Iodosylcarboxylates and Related Nucleophiles," Chem. Rev. 2002, 102(7), 2497-2522.

Immobilization of iodoso- and iodoxybenzoate reagents into paints, synthetic fabrics and other colloidal systems can result in self-decontaminating materials. R. A. Moss, Y. C. Chung, "Immobilized iodosobenzoate catalysts for the cleavage of reactive phosphates," J. Org. Chem. 1990, 55(7), 2064-2069. Moss and Chung reported iodosobenzoate catalysts immobilized onto macroreticular acrylate resin with pending dimethylamino groups, which mimicked a micellar catalyst and exhibited reactivity comparable to aqueous micellar suspensions. Moss, R. A.; Chung, Y.-C. J. Org. Chem. 1990, 55, 2064.; R. A. Moss, Y.-C. Chung "An Efficient Iodosobenzoate-Functionalized Polymer for the Cleavage of Reactive Phosphates," Langmuir 1990, 6, 1614-1616. Numerous reported synthetic routes toward IBA and IBX moiety immobilization included (but were not limited to) silylation of silica or titanium dioxide followed by coupling with dimethylamine iodobenzoate derivative with the subsequent oxidation of the iodo- to iodoso-reagents, coupling of hydroxyiodobenzoic acid to an aminoalkyl-derivatized macroporous resin, chloromethyl polystyrene, or silica gel via an aryl ether or phenoxide linkers, modification of nylon into aminonylon, which could be further quaternized with iodobenzoate, leading to the quaternary ammonium iodobenzoate nylon derivative, or quaternization of dimethylamino groups of a commercially available resin by iodobenzoate moieties followed by their oxidation to iodosobenzoate groups. R. A. Moss, Y. C. Chung, "Immobilized iodosobenzoate catalysts for the cleavage of reactive phosphates," J. Org. Chem. 1990, 55(7), 2064-2069; R. A. Moss, Y.-C. Chung "An Efficient Iodosobenzoate-Functionalized Polymer for the Cleavage of Reactive Phosphates," Langmuir 1990, 6, 1614-1616; Mulbaier, M., Giannis, A., "The synthesis and oxidative properties of polymer-supported IBX," Angew. Chem. Int. Ed. 2001, 40(23), 4393-4394; Sorg, G., Mengel, A., Jung, G., Rademann, J. "Oxidizing polymers: a polymer-supported, recyclable hypervalent iodine (V) reagent for the efficient conversion of alcohols, carbonyl compounds, and unsaturated carbamates in solution," Angew. Chem. Int. Ed. 2001, 40(23), 4395-4397; Reed, N. N., Delgado, M., Hereford, K., Clapman, B., Janda, K. D., "Preparation of soluble and insoluble polymer supported IBX reagents," Bioorg. Medicinal Chem. Lett. 2002, 12, 2047-2049; Togo, H.; Sakuratani, K. "Polymer-supported hypervalent iodine reagents," Synlett 2002, 12, 1966-1975; Ladziata, U., Willging, J., Zhdankin, V. V. "Facile Preparation and Reactivity of Polymer-Supported N-(2-Iodyl-phenyl)-acylamide, an Efficient Oxidizing System," Org. Lett. 2006, 8(1), 167-170.

However, all of the approaches described above were multistep syntheses involving either careful choice or extensive chemical derivatization of a surface prior to the conjugation of an iodocarboxylate moiety, for example. Therefore, needed is a method of derivatizing substrates to enable them to decompose organophosphate agents, without the need for extensive pretreatment of the substrate prior to derivatization.

SUMMARY OF THE INVENTION

One aspect of the present invention relates to reactive compositions, wherein a metal oxide cluster is used to connect a reactive group (or groups) to the surface of a substrate. In certain embodiments, the reactive group in the compositions decomposes organophosphate agents through nucleophilic hydrolysis. In certain embodiments, the reactive group in the compositions is bactericidal. Remarkably, the use of metal oxide clusters in the inventive compositions permits incorporation of higher quantities of nucleophilic and bactericidal groups without the difficulties associated with having to pretreat the substrate prior to its association with reactive groups.

Aspects of the present invention relate to compositions and methods for sorbing (e.g., adsorption and chemisorption) and destroying organophosphate chemical agents. One aspect of the invention relates to a strategy toward modification of polymers having hydroxyl or amino groups on their surface by the o-iodoxybenzoyl (IBX) groups. IBX-modified poly (vinyl alcohol) and microcrystalline cellulose were shown to be capable of hydrolyzing diisopropyl fluorophosphate (DFP), an analog of sarin and soman, at pH 7.4 with the apparent second-order rate constants (k") of $4.6 \times 10^{-2}$ and $2.7 \times 10^{-2}$ M-1 s$^{-1}$ respectively. The IBX-Cellulose and IBX-PVA suspensions accelerated chlorpyrifos degradation 26- and 122-fold compared to the corresponding unmodified cellulose and PVA suspensions, respectively. The methods of modification are appropriate for a wide variety of surfaces, e.g., enabling the production of surfaces for chemical defense applications.

BRIEF DESCRIPTION OF THE FIGURES

FIG. 12 depicts FTIR spectra of IBX-modified polymers and their unmodified counterparts.

FIG. 17 tabulates the half-life ($t_{1/2}$) and second-order rate constant (k") of chlorpyrifos (CP) and chlorpyrifos oxon (CPO) degradation in various media.

FIG. 24 depicts cluster structure before (a) and after (b) overall chemical modification. Samples were prepared by putting a water dispersion of particles at 0.005 wt % on the TEM grid and evaporating the water at room temperature.

FIG. 47 depicts (a) dependence of observed hydrolytic kinetic constants of methyl-paraoxon on particle concentration. Slope of the linear fitting was second order kinetic constant: $k_{cat}=1.1\times10^{-6}$ (mg/mL)$^{-1}$s$^{-1}$; and (b) dependence of observed hydrolytic kinetic constants of ethyl-paraoxon on particle concentration. Slope of the linear fitting was second order kinetic constant: $k_{cat}=1.8\times10^{-7}$ (mg/mL)$^{-1}$s$^{-1}$.

DETAILED DESCRIPTION OF THE INVENTION

Figure 1:
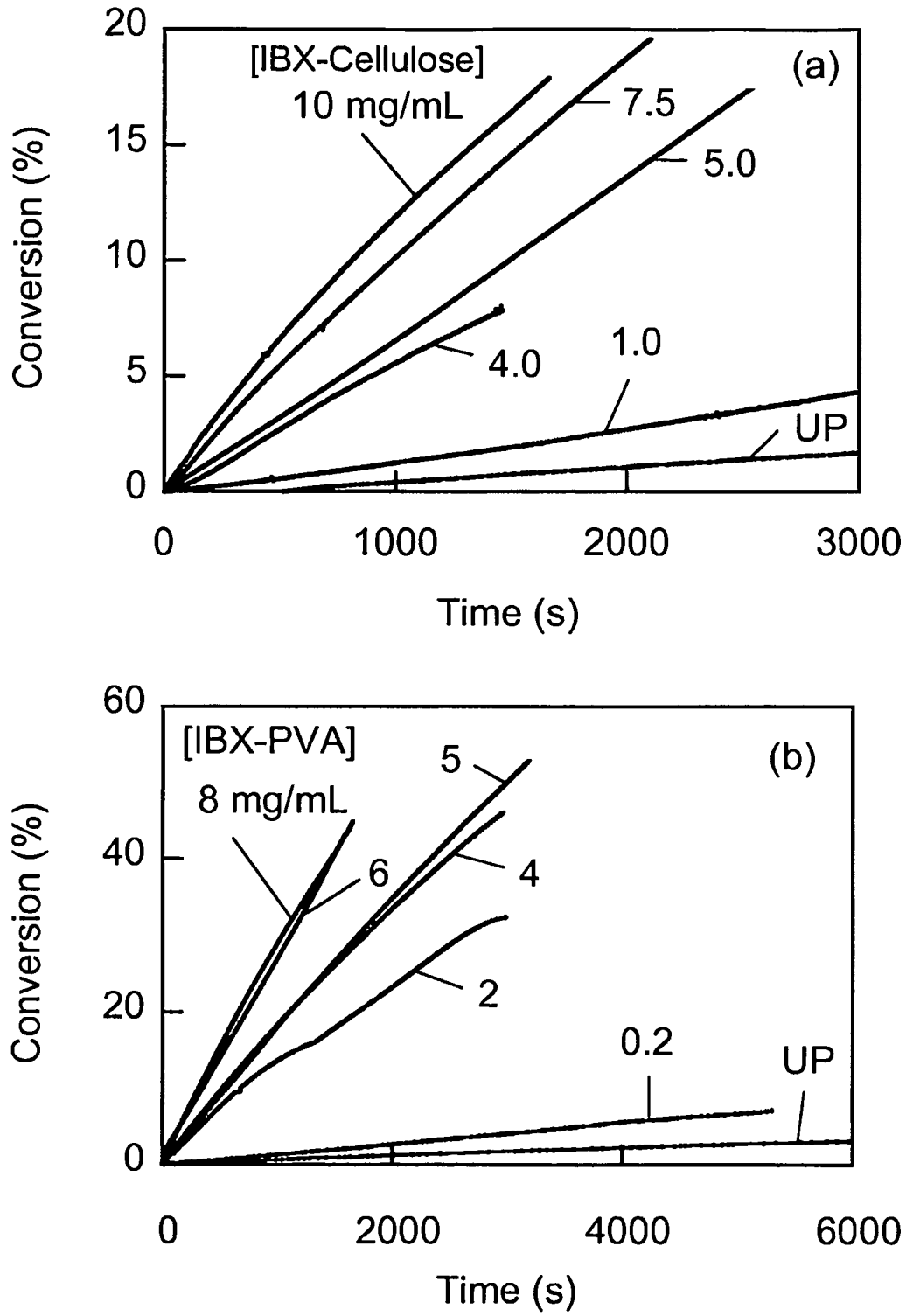
FIG. 1 depicts kinetic data from DFP hydrolysis in IBX-Cellulose (a) and IBX-PVA (b) suspensions. Conversion, %=100×$C_t$/[DFP]$_o$. "UP" stands for 10 mg/mL solution of unmodified polymer, while numbers designate polymer concentration in mg/mL. [DFP]$_o$=6 mM, pH 7.4, 50 mM Tris buffer, 25° C.

One aspect of the present invention relates to compositions and methods for destroying dangerous substances, such as chemical and biological agents. Organophosphorus pesticides and warfare agents are not readily hydrolyzed in aqueous media without applying extremes of pH, heat, or bleach. Remarkably, the methods of the invention are carried out by contacting the target substance with a substrate comprising a nucleophilic group.

As used herein, the term "substrate" refers to substrates upon which reactive groups can be disposed. Non-limiting examples of substrates include colloids and other types of particles; surfaces (including exterior or the interior, of a vehicle, aircraft, building, protective barrier, furniture, computer, paper sheet, interfacial layers and the like); textiles (including garments, woven or non-woven fabrics or article therefrom); paint; coatings; inks; adhesives; absorbents; toners; membranes; filters; and the like. In certain embodiments, the colloid is dispersed in air, water, organic solvent, fresh water, ocean water, or bodily fluid.

In certain embodiments, the substrate is a colloid dispersed in a gas or a liquid (such as air, fresh or ocean water, bodily fluids, or organic solvents). In certain embodiments the substrate is a surface, exterior or interior, of a vehicle, aircraft, building, protective barrier, furniture, computer, paper sheet and the like dispersed in a liquid or gas (such as air, water, or organic solvents). In certain embodiments, the substrate is a fiber, textile, garment, sheet of paper, woven or non-woven fabrics or article therefrom dispersed in a liquid or a gas (such as air, fresh or ocean water, bodily fluids, or organic solvents). In certain embodiments, the substrate is paint, a coating, ink, an adhesive, an absorbent, toner, a membrane, a filter and the like dispersed in a liquid or a gas (such as air, fresh or ocean water, bodily fluids, or organic solvents). In certain embodiments, the substrate is a particle dispersed in a liquid or a gas (such as air, fresh or ocean water, bodily fluids, or organic solvents).

Two exemplary depictions of compositions of the invention are shown below in Scheme 1. Scheme 1 depicts a substrate bonded to a cluster, wherein X is a moiety on the surface of the substrate that can covalently or non-covalently bind the substrate to the cluster. Several clusters can be bonded to a single substrate (limited only by the number of Xs on the surface and steric constraints). In addition, the cluster is connected to one or more reactive groups through one or more linkers. Several linkers can be bonded to a single cluster (again, only limited by the number of reactive centers and sterics); and the cluster can be attached to the substrate through one or more bonds. By this approach, a large number of reactive groups can be connected to a substrate.

Scheme 1.
Pictorial representations of selected modified substrates of the invention.

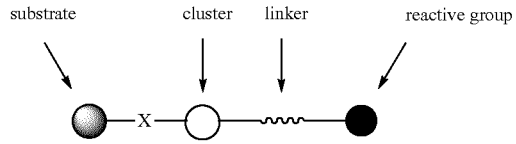

-continued

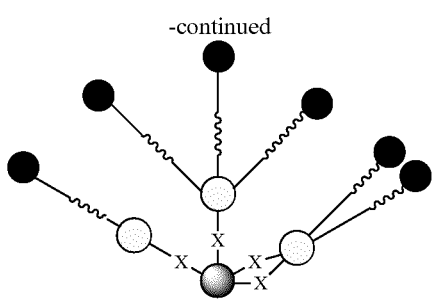

As used herein, "cluster" is a small group of atoms or molecules chosen from, but not limited to metals and metal oxides (such as, for example, silica, titania and ceria). In certain embodiments, the cluster consists essentially of metals or metal oxides. In certain embodiments, the cluster comprises one or metals or metal oxides selected from oxides of the metals of Groups 1-15 of the Periodic Table. These metals include Li, Na, K, Mg, Ca, Sr, Ba, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg. The term "metal" is also used to include metalloids belonging to Groups 13-15. These metalloids include B, Al, Ga, In, Tl, Si, Ge, Sn, Pb, As, Sb, and Bi. In certain embodiments, the metals of the metals or metal oxides belong to Groups 8-12, which include Fe, Ru, Os, Co, Rh, Ir, Ni, Pd, Pt, Cu, Ag, Au, Zn, Cd, and Hg. In certain embodiments, the cluster comprises metal oxides selected from the group consisting of the oxides of Fe, Ni, Cu or Zn.

In certain embodiments, the metal oxides are magnetic metals or metal oxides. Magnetic metals may include $Fe^0$, $Co^0$, $Ni^0$; metal oxides of the invention may include Fe either as Fe(II), Fe(III), or a mixture of Fe(II)/Fe(III). Non-limiting examples of such oxides include FeO, $Fe_2O_3$, and $Fe_3O_4$. The inorganic compound may also be a mixed oxide of the type $M^1{}_xM^2{}_{3-x}O_4$, wherein $M^1$ represents a divalent metal ion and $M^2$ represents a trivalent metal ion. For example, the inorganic compound may be magnetic ferrites of the formula $M^1Fe_2O_4$, wherein $M^1$ represents a divalent ion selected from the following: Mn, Co, Ni, Cu, Zn, or Ba, pure or in admixture with each other or in admixture with ferrous ions.

The substrate and cluster can be attached in a variety of ways. In certain embodiments, the substrate and cluster are connected through a coordination bond metal-organic, a covalent bond, a hydrogen bond or an ionic bond. In certain embodiments, —OH or —$NH_2$ moieties on the surface of the colloid bind to a metal atom in the cluster.

As used herein, a "reactive group" is a chemical entity capable of either degrading organophosphorus compounds and/or inhibiting the growth of bacteria. In certain embodiments, the reactive group is selected from the group consisting of oximates, iodosobenzoates, iodoxybenzoates, imidazoles, and guanidines, as well as nucleophilic, oxidative, and bactericidal groups. The bactericidal groups can be effective against Gram-positive bacteria, Gram-negative bacteria, or both.

In certain embodiments the "linker" is an alkylene chain. However, any continuous chain of covalently bonded or coordinated atoms can be used to connect the cluster to the reactive group. In certain embodiments, branched linkers can be used wherein more than one end of the linker is bound to a reactive moiety.

In certain embodiments, the invention provides for functional, modified organic-inorganic colloids. In one embodiment, the modification is by the o-iodoxybenzoyl (IBX) group. In certain embodiments, the present invention describes a simple yet widely applicable route toward the modification of colloids containing hydroxyl or amino groups on their surface with covalently bound (conjugated), but still reactive o-iodoxy- or iodosobenzoate groups, without the necessity of the colloids' pre-treatment. For example, polymers which have been able to be modified included cellulose and poly(vinyl alcohol) (PVA), which are among the most common components of textiles. In certain embodiments, the modification is an imidazole group.

In certain embodiments, the value of the modification involving IBX stems not only from its nucleophilic properties, but also from the fact that it is a very active oxidant toward thiols, thiophosphinates, and thiophosphate esters such as O-ethyl S-(2-diisopropylaminoethyl)methylphosphonothioate (VX) as well as its analogs and stimulants. Chemospecific cleavage of the P—S bond is of importance in certain demilitarization techniques, primarily because a simple basic hydrolysis of VX affords a highly toxic phosphonothioate fragment, which renders this process useless for decontamination purposes. Notably, upon reduction, the IBX is converted into o-iodosobenzoate, a powerful nucleophile capable of catalytically cleaving the P—O bonds of the organophosphates.

In certain embodiments, the present invention exploits both the nucleophilic and the oxidative properties of, for example, IBX-modified polymers. The possibility of partial reduction of the IBX to IBA groups by the alcohol groups present on the polymer (when excess Oxone is removed by the modified polymer purification) may in fact be advantageous for the nucleophilic cleavage of P—O groups, as the IBA group is a nucleophile even more powerful than the IBX group. Moss, R. A.; Morales-Rojas, H.; Zhang, H.; Park, B.-D., *Langmuir,* 1999; 15(8), 2738-2744. On the other hand, IBX is a much stronger oxidant than IBA. Thottumkara, A. P.; Bowsher, M. S.; Vinod, T. K. *Org. Lett.,* 2005; 7(14), 2933-2936. In certain embodiments, the strong nucleophile is a hydroxamate.

In certain embodiments, O,O-diethyl O-(3,4,5-trichloro-2-pyridyl) phosphorothioate (chlorpyrifos) was chosen as a model compound enabling further revelation of the potential of IBX-modified colloids for the destruction of chemical agents including thiophosphates. In certain embodiments, modified polymers were active toward decomposition by nucleophilic hydrolysis of a model chemical warfare stimulant, diisopropyl fluorophosphate, an analog of sarin and soman. In certain embodiments, the modified polymers were active toward decomposition by hydrolysis and oxidation of a widely used organophosphate insecticide, chlorpyrifos.

One approach to colloid modification of the present invention is given in Scheme 2, which is not intended to limit the methods of the present invention. In certain embodiments, the colloid contains hydroxy- or amino-groups on the surface. In certain embodiments, the modifier contains trialkoxysilanylalkylcarbamoyloxy-iodobenzoic acid and is capable of covalently bonding with the colloid's surface via the sol-gel reaction. The iodobenzoic group of the modified colloid's surface is preferably modified by oxidation into nucleophilic and reactive o-iodoxybenzoic (IBX) group by oxidizing agents such as a mixture of $KHSO_5$—$KHSO_4$—$K_2SO_4$ salts and methanesulfonic acid, potassium permanganates, acidic perchlorates, and the like.

Scheme 2.

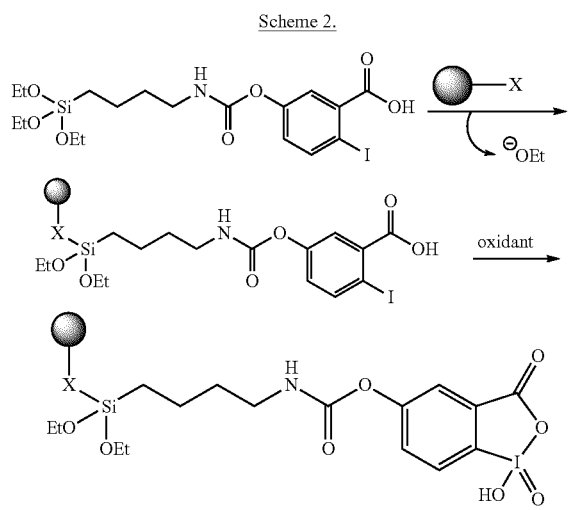

One route toward substrate modification with iodoxybenzoate groups (IBX), where ● represents the substrate (such as a metal oxide particle, a polymer molecule, a solid surface or a ceramic); X represents —OH (or —O—) or —NH$_2$ (or —N(H)—).

Each substrate may have a plurality of Xs, though above only one is shown.

In certain embodiments, the invention describes methods to modify a substrate which comprises pendant carboxyl groups with α-nucleophilic groups, such as hydroxamates, oximes and oximates. The substrates containing oxime groups on their surface decompose esters, such as nitrophenyl acetate. Such oxime-modified substrates are preferably magnetic and recoverable by high gradient magnetic separation. Imidazole-modified substrates have similar properties as oxime-modified substrates. Hydroxamic acid-modified particles also decompose nitrophenyl acetate. Also, OP compounds, such as methyl-paraoxon and ethyl-paraoxon are decomposed by the hydroxamic acid-modified particles.

In certain embodiments, the invention relates to the modification of substrate to comprise drugs, such as antimicrobial agents. The colloids modified with said antimicrobial agents, such as bisguanide or N-alkylguanidine, are bactericidal toward both Gram-positive and Gram-negative bacteria. In certain embodiments, the bactericidal drug is chlorhexidine.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "associated with" as used herein in such phrases as, for example, "an inorganic metal oxide associated with an stabilizing compound," refers to the presence of either weak or strong or both interactions between molecules. For example weak interactions may include, for example, electrostatic, van der Waals, or hydrogen-bonding interactions. Stronger interactions, also referred to as being chemically bonded, refer to, for example, covalent, ionic, or coordinative bonds between two molecules. The term "associated with" also refers to a compound that may be physically intertwined within the foldings of another molecule, even when none of the above types of bonds are present. For example, an inorganic compound may be considered as being in association with a polymer by virtue of it existing within the interstices of the polymer.

The terms "comprise" and "comprising" are used in the inclusive, open sense, meaning that additional elements may be included.

The term "including" is used to mean "including but not limited to". "Including" and "including but not limited to" are used interchangeably.

The term "polymer" is used to mean a large molecule formed by the union of repeating units (monomers). The term polymer also encompasses copolymers.

The term "co-polymer" is used to mean a polymer of at least two or more different monomers.

The term "particle size" is used to mean a number-average or weight-average particle size as measured by conventional particle size measuring techniques well known to those skilled in the art, such as dynamic or static light-scattering, sedimentation field-flow fractionation, photon-correlation spectroscopy, or disk centrifugation. By "an effective average particle size of less than about 1000 nm" it is meant that at least about 90% of the particles have a number-average or weight-average particle size of less than about 1000 nm when measured by at least one of the above-noted techniques.

The term "interstices" is used to mean a space, especially a small or narrow one, between things or parts.

The term "chemical coprecipitation" as used herein refers to a common technique for making aqueous magnetic fluids from metal salts. This technique may be used to produce ferrite particles, such as magnetite ($Fe_3O_4$), maghemite ($\gamma$—$Fe_2O_3$), or cobalt ferrite ($CoFe_2O_4$).

The term "diamagnetic" as used herein means having a negative magnetic susceptibility.

The term "magnet" as used herein refers to a substance composed of ferromagnetic or ferrimagnetic material having domains that are aligned to produce a net magnetic field outside the substance or to experience a torque when placed in an external magnetic field.

The term "magnetic core" as used herein refers to a piece of magnetic material, often of iron oxide or ferrite that is within a copolymer shell, coil, transformer, or electromagnet.

The term "magnetic field" as used herein refers to a vector field occupying physical space wherein magnetic forces may be detected, typically in the presence of a permanent magnet, current-carrying conductor, or an electromagnetic wave.

The term "magnetic field strength" as used herein refers to a vector field used to describe magnetic phenomena, having the property that the curl of the field is equal to the free current density vector in the meter-kilogram-second system of units.

The term "magnetic separation" as used herein refers to a process that uses a magnetic solid and an external magnetic field to separate materials or compounds. Examples of magnetic separation include magnetocollection, magnetoflocculation, and magnetoanisotropic sorting.

The term "magnetic susceptibility" as used herein refers to the ratio of the magnetization of a substance to the applied magnetic field strength.

The term "magnetite" as used herein refers to a chemical compound represented as $Fe_2O_3$*$FeO$ or $Fe_3O_4$ in the spinel iron oxide species with a 2:1 molar ratio of Fe ions that are present in their III and II oxidation states, respectively.

The term "magnetite nanoparticles" as used herein refers to either the magnetic core of the magnetic particles that make up a magnetic fluid, or to the magnetic particles as a whole, including both the magnetite core and the polymer shell that stabilizes them in the surrounding liquid.

The term "non-magnetic particle" as used herein refers to a particle that does not have inherent magnetic properties.

The term "superparamagnetism" as used herein refers to the tendency of fine particles to behave independently of one another in a manner similar to paramagnets, so that the particles show a net magnetization in the presence of a magnetic field, but then rapidly relax to show zero net magnetization when the applied magnetic field is removed.

The term "nucleophile" is recognized in the art, and as used herein means a chemical moiety having a reactive pair of electrons. Examples of nucleophiles include uncharged compounds, such as water, amines, mercaptans and alcohols, and charged moieties, such as alkoxides, thiolates, carbanions, oximes and a variety of organic and inorganic anions.

The term "α-nucleophile" is recognized in the art, and as used herein means a nucleophile possessing a heteroatom with an unshared electron pair adjacent to the nucleophilic center.

The term "n-nucleophile" is recognized in the art, and as used here means a nucleophile comprising a lone pair of electronics in a non-bonding orbital.

The term 'Gram-positive bacteria' is an art recognized term for bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abcessus*, *Mycobacterium avium* complex, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terrae*, *Mycobacterium tuberculosis*, *Mycobacterium ulcerans*, *Nocardia* spp., *Peptococcus niger*, *Peptostreptococcus* spp., *Proprionibacterium* spp., *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, *Streptococcus sanguis*.

The term "Gram-negative bacteria" is an art recognized term for bacteria characterized by the presence of a double membrane surrounding each bacterial cell. Representative Gram-negative bacteria include *Acinetobacter calcoaceticus*, *Actinobacillus actinomycetemcotnitans*, *Aeromonas hydrophila*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chalmydia pneumoniae*, *Chlamydia psittaci*, *Chlamydia trachomatis*, *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella* spp., *Legionella* spp., *Leptospira* spp., *Moraxella catarrhalis*, *Morganella morganii*, *Mycoplasma pneumoniae*, *Neisseria gonorrhoeae*, *Neisseria meningitidis*, *Pasteurella multocida*, *Plesiomonas shigelloides*, *Prevotella* spp., *Proteus* spp., *Providencia rettgeri*, *Pseudomonas aeruginosa*, *Pseudomonas* spp., *Rickettsia prowazekii*, *Rickettsia rickettsii*, *Rochalimaea* spp., *Salmonella* spp., *Salmonella typhi*, *Serratia marcescens*, *Shigella* spp., *Treponema carateum*, *Treponema pallidum*, *Treponema pallidum endemicum*, *Treponema pertenue*, *Veillonella* spp., *Vibrio cholerae*, *Vibrio vulnificus*, *Yersinia enterocolitica*, *Yersinia pestis*.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "alkylene" is art-recognized, and as used herein, pertains to a bidentate moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated. Examples of linear saturated $C_{1-10}$alkylene groups include, but are not limited to, —$(CH_2)_n$— where n is an integer from 1 to 10, for example, —$CH_2$—(methylene), —$CH_2CH_2$— (ethylene), —$CH_2CH_2CH_2$— (propylene), —$CH_2CH_2CH_2CH_2$-(butylene), —$CH_2CH_2CH_2CH_2CH_2$— (pentylene) and —$CH_2CH_2CH_2CH_2CH_2CH_2$— (hexylene). Examples of branched saturated $C_{1-10}$alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)$—$CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—. Examples of linear partially unsaturated $C_{1-10}$alkylene groups include, but are not limited to, —CH=CH— (vinylene), —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—$CH_2$—CH=CH—, and —CH=CH—$CH_2$—$CH_2$—CH=CH—. Examples of branched partially unsaturated $C_{1-10}$alkylene groups include, but are not limited to, —$C(CH_3)$=CH—, —$C(CH_3)$=CH—$CH_2$—, and —CH=CH—CH($CH_3$)—. Examples of alicyclic saturated $C_{1-10}$alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-10}$alkylene groups include, but are not limited to, cyclopentenylene (e.g., 4-cyclopenten-1, 3-ylene), and cyclohexenylene (e.g., 2-cyclohexen-1,4-ylene, 3-cyclohexen-1,2-ylene, and 2,5-cyclohexadien-1,4-ylene).

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphonate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art recognized and includes an aromatic or non-aromatic ring in which each atom of the ring is carbon. The flowing art-recognized terms have the following meanings: "nitro" means —$NO_2$; the term "halogen" designates —F, —Cl, —Br or —I; the term "sulfhydryl" means —SH; the term "hydroxyl" means —OH; and the term "sulfonyl" means —$SO_2^-$.

The terms "amine" and "amino" are art-recognized and include both unsubstituted and substituted amines, e.g., a moiety that may be represented by the general formulas:

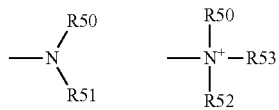

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

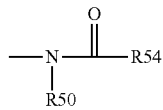

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

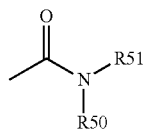

wherein R50 and R51 are as defined above. Certain embodiments of the amide in the present invention will not include imides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

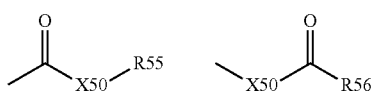

wherein X50 is a bond or represents an oxygen or a sulfur, and R55 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "oxime" is an art recognized moiety that may be represented by the general formula:

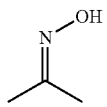

An "oximate anion" is a deprotonated oxime. Examples of useful oximes readily forming oximate anions include, but are not limited to, salicylaldoxime, 2-pyridinealdoxime, 2-hydroxy-5-nonylacetophenone oxime, 1-cetyl-3-(2-oximopropyl)imidazolium chloride, oxime methacrylate, hexadecyltrimethylammonium anti-pyruvaldehyde 1-oximate, anti-pyruvaldehyde 1-oxime (monoisonitrosoacetone), O-(2, 3,4,5,6,-pentafluorobenzyl)hydroxylamine hydrochloride, 1,1'-trimethylene bis(4-hydroxyiminomethyl)pyridinium dichloride (trimedoxime), 4-amino-4-methyl-2-pentanone oxime, and the like.

The term "hydroxamic acid" is an art recognized moiety that may be represented by the general formula:

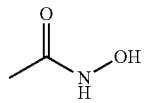

A "hydroxamate anion" is a deprotonated hydroxamic acid.

The term "sulfonate" is art recognized and includes a moiety that may be represented by the general formula:

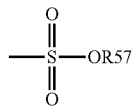

in which R57 is an electron pair, hydrogen, alkyl, cycloalkyl, or aryl.

The term "sulfate" is art recognized and includes a moiety that may be represented by the general formula:

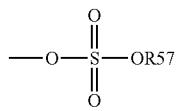

in which R57 is as defined above.

The term "sulfonamido" is art recognized and includes a moiety that may be represented by the general formula:

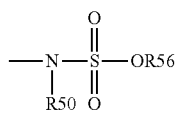

in which R50 and R56 are as defined above.

The term "sulfamoyl" is art-recognized and includes a moiety that may be represented by the general formula:

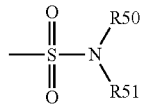

in which R50 and R51 are as defined above.

The term "sulfonyl" is art recognized and includes a moiety that may be represented by the general formula:

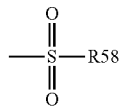

in which R58 is one of the following: hydrogen, alkyl, alkenyl, alkynyl, cycloalkyl, heterocyclyl, aryl or heteroaryl.

The term "sulfoxido" is art recognized and includes a moiety that may be represented by the general formula:

in which R58 is defined above.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoroethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoroethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. Protective Groups in Organic Synthesis, 2nd ed.; Wiley: New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Compositions

One aspect of the invention relates to a composition, comprising a substrate, a cluster, and a reactive group; wherein a bond connects the cluster to the substrate, and a linker connects the cluster to the reactive group.

Another aspect of the invention relates to a composition comprising a substrate, a cluster, and a reactive group; wherein a bond connects the cluster to the substrate, and a second bond connects the cluster to the reactive group.

In certain embodiments, the present invention relates to any one of the aforementioned compositions, wherein the substrate is a polymer, vehicle, aircraft, building, protective barrier, furniture, computer, paper sheet, fiber, textile, garment, woven fabric, non-woven fabric, paint, coating, ink, adhesive, absorbent, toner, membrane, filter or particle.

In certain embodiments, the present invention relates to any one of the aforementioned compositions, wherein the substrate is a polymer.

In certain embodiments, the present invention relates to any one of the aforementioned compositions, wherein the substrate is a polymer having pendant hydroxyl or amino groups.

In certain embodiments, the present invention relates to any one of the aforementioned compositions, wherein the substrate is a polysaccharide.

In certain embodiments, the present invention relates to any one of the aforementioned compositions, wherein the substrate is cellulose or poly(vinyl alcohol).

In certain embodiments, the present invention relates to any one of the aforementioned compositions, wherein the bond is a coordination bond metal-organic, a covalent bond, a hydrogen bond or an ionic bond.

In certain embodiments, the present invention relates to any one of the aforementioned compositions, wherein the second bond is a coordination bond metal-organic, a covalent bond, a hydrogen bond or an ionic bond.

In certain embodiments, the present invention relates to any one of the aforementioned compositions, wherein the cluster is a metal oxide cluster.

In certain embodiments, the present invention relates to any one of the aforementioned compositions, wherein the cluster is ceria.

In certain embodiments, the present invention relates to any one of the aforementioned compositions, wherein the cluster is silica.

In certain embodiments, the present invention relates to any one of the aforementioned compositions, wherein the cluster is titania.

In certain embodiments, the present invention relates to any one of the aforementioned compositions, wherein the cluster is an iron oxide.

In certain embodiments, the present invention relates to any one of the aforementioned compositions, wherein the substrate is a polymer having pendant hydroxyl or amino groups; the cluster is metal oxide cluster; and the bond is a bond from the oxygen of the pendant hydroxyl, or the nitrogen of the pendant amino, to the metal in the metal oxide.

In certain embodiments, the present invention relates to any one of the aforementioned compositions, wherein the linker is represented by $B^1$—Y—Z—$B^2$; $B^1$ is a bond to the cluster; Y is alkylene; Z is absent, —O—, —N(H)—, —S—, —C(=O)O—, —C(=O)N(H)—, —OC(=O)O—, —OC(=O)N(H)—, —N(H)C(=O)O—, —N(H)C(=O)N(H)—, —C(=O)S—, —S(=O)—, —S(=O)$_2$—, —C(=O)—, —C(=NH)—, or —C(=S)—; and $B^2$ is a bond to the reactive group.

In certain embodiments, the present invention relates to any one of the aforementioned compositions, wherein the linker is represented by $B^1$—(CH$_2$)$_n$—Z—$B^2$; $B^1$ is a bond to the cluster; n is 1-10 inclusive; Z is absent, —O—, —N(H)—, —S—, —C(=O)O—, —C(=O)N(H)—, —OC(=O)O—, —OC(=O)N(H)—, —N(H)C(=O)O—, —N(H)C(=O)N(H)—, —C(=O)S—, —S(=O)—, —S(=O)$_2$—, —C(=O)—, —C(=NH)—, or —C(=S)—; and $B^2$ is a bond to the reactive group.

In certain embodiments, the present invention relates to any one of the aforementioned compositions, wherein the linker is represented by $B^1$—(CH$_2$)$_n$—Z—$B^2$; $B^1$ is a bond to the cluster; Z is —C(=O)O—, —OC(=O)N(H)—, —N(H)C(=O)O—, or —N(H)C(=O)N(H)—; and $B^2$ is a bond to the reactive group.

In certain embodiments, the present invention relates to any one of the aforementioned compositions, wherein the linker is represented by $B^1$—(CH$_2$)$_3$—N(H)C(=O)O—$B^2$; $B^1$ is a bond to the cluster; and $B^2$ is a bond to the reactive group.

In certain embodiments, the present invention relates to any one of the aforementioned compositions, wherein the reactive group is a chemical entity capable of degrading organophosphorus compounds.

In certain embodiments, the present invention relates to any one of the aforementioned compositions, wherein the reactive group is a chemical entity capable of degrading thioether compounds.

In certain embodiments, the present invention relates to any one of the aforementioned compositions, wherein the reactive group is a chemical entity capable of inhibiting the growth of bacteria.

In certain embodiments, the present invention relates to any one of the aforementioned compositions, wherein the reactive group comprises an oximate, an iodosobenzoate, an iodoxybenzoate, an amidooxime, an imidazole, an amine, a peroxide, a guanidine, a nucleophile, an oxidant, or a bactericide.

In certain embodiments, the present invention relates to any one of the aforementioned compositions, wherein said nucleophile is selected from the group consisting of oximes, hydroxamic acids, hydrazines, hydrazones, imidazoles, iodosoaryl compounds and sulfoxides.

In certain embodiments, the present invention relates to any one of the aforementioned compositions, wherein the reactive group is

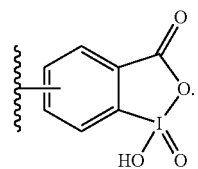

In certain embodiments, the present invention relates to any one of the aforementioned compositions, wherein the reactive group is

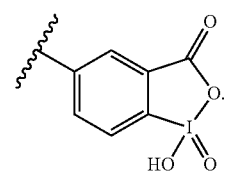 [SMILES: *c1ccc2c(c1)C(=O)OI2(=O)O]

In certain embodiments, the present invention relates to any one of the aforementioned compositions, wherein the reactive group comprises an oximate.

In certain embodiments, the present invention relates to any one of the aforementioned compositions, wherein the reactive group comprises an imidazole.

In certain embodiments, the present invention relates to any one of the aforementioned compositions, wherein the reactive group is poly(acrylamidoxime).

In certain embodiments, the present invention relates to any one of the aforementioned compositions, wherein the reactive group is chlorhexidine; and said chlorhexidine is bonded to the linker through one of its amines.

In certain embodiments, the present invention relates to any one of the aforementioned compositions, wherein the cluster is silica; and the tether-reactive group is

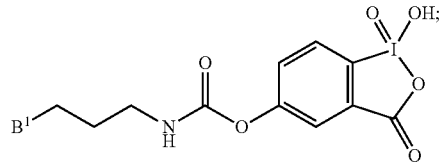

and $B^1$ is a bond to a silicon atom in the cluster.

Organophosphates

Organophosphates are rapidly absorbed by inhalation, ingestion and through the skin. The absorbed chemical as well as the active metabolite bind to the cholinesterase enzymes found in red blood cells and plasma. The binding to these enzymes leads to their inactivation and hence renders them incapable of degrading an important neurotransmitter, acetycholine. The excessive acetylcholine then accumulates at nerve junctions in the skeletal muscle system and in the autonomic and central nervous systems. With time, typically after 24 to 36 hours, this inactivation becomes irreversible.

Organophosphate esters are used as both insecticides and chemical warfare agents. Exemplary phosphate esters which can be hydrolyzed by the compositions and methods of the present invention are phosphates, phosphorofluoridates, phosphonates, and their sulfur analogs such as phosphorothionates. Exemplary organophosphate esters include parathion, malathion, diazinon, phosmet (Imidan®), chlorpyrifos (Lorsban®), sarin, tabun (ethylphosphorodimethylamidocyanidate), soman (pinacolyl methylphosphonerfluoridate), GF (Cyclohexyl methylphosphonofluoridate) and VX (ethyl S-2-diisopropyl aminoethyl methylphosphoro-thioate). Due to the toxicity of may organophosphates, such as those listed above, hydrolysis of a model OPE nerve agent, diisopropyl fluorophosphate (DFP), was used in the exemplification disclosed herein.

Destruction of an Organophosphate by Inventive Compositions

The compositions of the present invention can be used in processes for the decontamination of chemical warfare nerve agents and pesticides. In certain embodiments, the compositions will hydrolyze materials which contain either a phosphono-group or a phosphoro-group. One or both of the hydrolysis and adsorption properties can be employed in particular decontamination process depending upon the particular needs at the site of the decontamination.

Decontamination is accomplished simply by contacting one of the inventive compositions with the phosphate ester to adsorb and/or hydrolyze it. If a step of adsorption without hydrolysis is desired for a particular decontamination process, then a sufficient amount of said composition should be employed to adsorb substantially all of the phosphate ester. The proper amount of composition to be used in a particular clean-up can be determined by routine experimentation.

Inventive Compositions as Protective Barriers in Fabrics

Heightened awareness of the hazards of chemical pollutants and pesticides, coupled with a growing threat of chemical exposure due to accidental spills or terrorist action, poses a challenge to develop countermeasures. Current protection gear (e.g., gloves, masks, and clothing) is based on the removal of environmental toxins using efficient adsorption materials, and/or the use of impermeable barriers. Both approaches suffer from problems such as weight, cost, bulkiness, regeneration capabilities, and disposal safety concerns. Therefore, there is an urgent need to develop non-corrosive, environmentally benign, cost-effective, lightweight, robust, self-decontaminating, hazardous material-free systems for handling and neutralizing pesticides and toxins present in air or water. Such systems can comprise protective layers in fabrics used in wearable garments. To illustrate the performance of the novel compositions as protective barriers, they were embedded in Polartec® fabric (Malden Mills, Lawrence, Mass.) as described herein.

Methods

One aspect of the present invention relates to a method of making a modified substrate, comprising the step of reacting under sol-gel conditions a substrate with pendant hydroxyl or amino groups with a compound comprising a cluster tethered via a tether to a reactive group.

Another aspect of the present invention relates to a method of making a modified substrate, comprising the steps of reacting a substrate with pendant hydroxyl or amino groups with a metal oxide, thereby forming a metal oxide cluster bonded to said substrate; and reacting said cluster with a compound having a reactive group, thereby tethering the reactive group to the cluster via a tether.

Another aspect of the present invention relates to a method for the hydrolysis of a compound which contains at least one oxidized phosphorus group or killing a bacteria, comprising the step of contacting said compound with a composition for sufficient to hydrolyze at least some of the oxidized phosphorus groups in said compound or to kill the bacteria; wherein said composition comprises a substrate, a cluster, and a reactive group; wherein a bond connects the cluster to the substrate, and a linker connects the cluster to the reactive group.

Another aspect of the present invention relates to a method for the hydrolysis of a compound which contains at least one oxidized phosphorus group or killing a bacteria, comprising the step of contacting said compound with a composition for sufficient to hydrolyze at least some of the oxidized phosphorus groups in said compound or to kill the bacteria; wherein said composition comprises a substrate, a cluster, and a reactive group; wherein a bond connects the cluster to the substrate, and a second bond connects the cluster to the reactive group.

In certain embodiments, the present invention relates to any one of the aforementioned methods, wherein the substrate is a polymer, vehicle, aircraft, building, protective barrier, furniture, computer, paper sheet, fiber, textile, garment, woven fabric, non-woven fabric, paint, coating, ink, adhesive, absorbent, toner, membrane, filter or particle.

In certain embodiments, the present invention relates to any one of the aforementioned methods, wherein the substrate is a polymer.

In certain embodiments, the present invention relates to any one of the aforementioned methods, wherein the substrate is a polymer having pendant hydroxyl or amino groups.

In certain embodiments, the present invention relates to any one of the aforementioned methods, wherein the substrate is a polysaccharide.

In certain embodiments, the present invention relates to any one of the aforementioned methods, wherein the substrate is cellulose or poly(vinyl alcohol).

In certain embodiments, the present invention relates to any one of the aforementioned methods, wherein the bond is a coordination bond metal-organic, a covalent bond, a hydrogen bond or an ionic bond.

In certain embodiments, the present invention relates to any one of the aforementioned methods, wherein the second bond is a coordination bond metal-organic, a covalent bond, a hydrogen bond or an ionic bond.

In certain embodiments, the present invention relates to any one of the aforementioned methods, wherein the cluster is a metal oxide cluster.

In certain embodiments, the present invention relates to any one of the aforementioned methods, wherein the cluster is ceria.

In certain embodiments, the present invention relates to any one of the aforementioned methods, wherein the cluster is silica.

In certain embodiments, the present invention relates to any one of the aforementioned methods, wherein the cluster is titania.

In certain embodiments, the present invention relates to any one of the aforementioned methods, wherein the cluster is an iron oxide.

In certain embodiments, the present invention relates to any one of the aforementioned methods, wherein the substrate is a polymer having pendant hydroxyl or amino groups; the cluster is metal oxide cluster; and the bond is a bond from the oxygen of the pendant hydroxyl, or the nitrogen of the pendant amino, to the metal in the metal oxide.

In certain embodiments, the present invention relates to any one of the aforementioned methods, wherein the linker is represented by $B^1$—Y—Z—$B^2$; $B^1$ is a bond to the cluster; Y is alkylene; Z is absent, —O—, —N(H)—, —S—, —C(=O)O—, —C(=O)N(H)—, —OC(=O)O—, —OC(=O)N(H)—, —N(H)C(=O)O—, —N(H)C(=O)N(H)—, —C(=O)S—, —S(=O)—, —S(=O)$_2$—, —C(=O)—, —C(=NH)—, or —C(=S)—; and $B^2$ is a bond to the reactive group.

In certain embodiments, the present invention relates to any one of the aforementioned methods, wherein the linker is represented by $B^1$—$(CH_2)_n$—Z—$B^2$; $B^1$ is a bond to the cluster; n is 1-10 inclusive; Z is absent, —O—, —N(H)—, —S—, —C(=O)O—, —C(=O)N(H)—, —OC(=O)O—, —OC(=O)N(H)—, —N(H)C(=O)O—, —N(H)C(=O)N(H)—, —C(=O)S—, —S(=O)—, —S(=O)$_2$—, —C(=O)—, —C(=NH)—, or —C(=S)—; and $B^2$ is a bond to the reactive group.

In certain embodiments, the present invention relates to any one of the aforementioned methods, wherein the linker is represented by $B^1$—$(CH_2)_3$—Z—$B^2$; $B^1$ is a bond to the cluster; Z is —OC(=O)O—, —OC(=O)N(H)—, —N(H)C(=O)O—, or —N(H)C(=O)N(H)—; and $B^2$ is a bond to the reactive group.

In certain embodiments, the present invention relates to any one of the aforementioned methods, wherein the linker is represented by $B^1$—$(CH_2)_3$—N(H)C(=O)O—$B^2$; $B^1$ is a bond to the cluster; and $B^2$ is a bond to the reactive group.

In certain embodiments, the present invention relates to any one of the aforementioned methods, wherein the reactive group is a chemical entity capable of degrading organophosphorus compounds.

In certain embodiments, the present invention relates to any one of the aforementioned methods, wherein the reactive group is a chemical entity capable of degrading thioether compounds.

In certain embodiments, the present invention relates to any one of the aforementioned methods, wherein the reactive group is a chemical entity capable of inhibiting the growth of bacteria.

In certain embodiments, the present invention relates to any one of the aforementioned methods, wherein the reactive group comprises an oximate, an iodosobenzoate, an iodoxybenzoate, an amidooxime, an imidazole, an amine, a peroxide, a guanidine, a nucleophile, an oxidant, or a bactericide.

In certain embodiments, the present invention relates to any one of the aforementioned methods, wherein said nucleophile is selected from the group consisting of oximes, hydroxamic acids, hydrazines, hydrazones, imidazoles, iodosoaryl compounds and sulfoxides.

In certain embodiments, the present invention relates to any one of the aforementioned methods, wherein the reactive group is

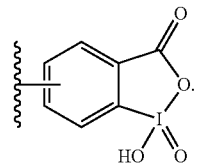

In certain embodiments, the present invention relates to any one of the aforementioned methods, wherein the reactive group is

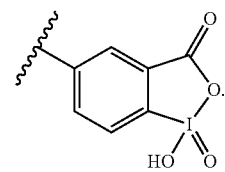 [SMILES: *c1ccc2c(c1)C(=O)OI2(=O)O]

In certain embodiments, the present invention relates to any one of the aforementioned methods, wherein the reactive group comprises an oximate.

In certain embodiments, the present invention relates to any one of the aforementioned methods, wherein the reactive group comprises an imidazole.

In certain embodiments, the present invention relates to any one of the aforementioned methods, wherein the reactive group is poly(acrylamidoxime).

In certain embodiments, the present invention relates to any one of the aforementioned methods, wherein the reactive group is chlorhexidine; and said chlorhexidine is bonded to the linker through one of its amines.

In certain embodiments, the present invention relates to any one of the aforementioned methods, wherein the cluster is silica; and the tether-reactive group is

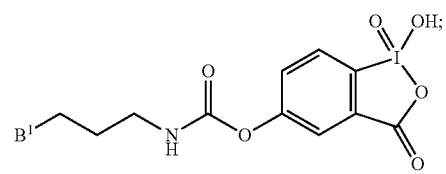

and $B^1$ is a bond to a silicon atom in the cluster.

Selected Articles of the Invention

One aspect of the present invention relates to an article selected from the group consisting of filters, wipes, sponges, gas masks, membranes, wearable protective garments or air filtration systems; wherein said article comprises any one of the aforementioned compositions.

Another aspect of the invention relates to an article, comprising a surface and a coating on said surface, wherein said coating comprises a plurality of any of the aforementioned compositions.

In certain embodiments, the present invention relates to any one of the aforementioned article, wherein said coating has a mass per surface area of less than about 500 μg/cm$^2$.

In certain embodiments, the present invention relates to any one of the aforementioned article, wherein said coating has a mass per surface area of less than about 100 μg/cm$^2$.

In certain embodiments, the present invention relates to any one of the aforementioned article, wherein said coating has a mass per surface area of less than about 50 μg/cm².

In certain embodiments, the present invention relates to any one of the aforementioned article, wherein said coating has a mass per surface area of less than about 10 μg/cm².

In certain embodiments, the present invention relates to any one of the aforementioned article, wherein said coating has a mass per surface area of less than about 5 μg/cm².

In certain embodiments, the present invention relates to any one of the aforementioned article, wherein said surface is selected from the group consisting of non-synthetic fibers, cellulosic fibers, cotton, proteinaceous fibers, wool, silk, synthetic fibers, nylon, polyester, polyurethane, polyanhydride, polyorthoester, polyacrylonitrile, polyphenazine, latex, teflon, dacron, acrylate polymer, chlorinated rubber, fluoropolymer, polyamide resin, vinyl resin, Gore-tex®, Marlex®, expanded polytetrafluoroethylene, low density polyethylene, high density polyethylene, polypropylene, and poly(ethylene terephthalate).

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of Iodoxybenzoate (IBX)-modified Substrates and their Properties

Materials Used. Microcrystalline cellulose (powder, ~20 μm), poly(vinyl alcohol) (PVA, 98% hydrolyzed, average Mw 13-23 kDa), 2-amino-5-hydroxybenzoic acid (1) (99%), methanesulfonic acid (99.5%), Oxone® tetrabutylammonium salt (active oxygen, ~1.6%), isoniazid (isonicotinyl hydrazide, ≥99%), O,O-diethyl O-(3,4,5-trichloro-2-pyridyl) phosphorothioate (CP, chlorpyrifos, 99%), diisopropylfluorophosphate (DFP, 99%), 1,2,4-trichlorobenzene (TCB, >99%), ethylmethyl phosphonate (EMP, >98%), and NMR glassware were all obtained from Sigma-Aldrich Chemical Co. DFP was stored at −70° C. and equilibrated at roam temperature in a sealed container prior to use. 3-Isocyanatopropyl-triethoxysilane (99%, Silquest® A-Link™ silane) was received as a generous gift from GE Silicones (Friendly, W. Va.). Chlorpyrifos oxon (CPO, >98%) was obtained from ChemService, Inc. (West Chester, Pa.). Cellulose was lyophilized from its 10-wt % suspension in deionized water. All other chemicals, solvents, and gases were obtained from commercial sources and were of highest purity available.

Synthesis of 5-Hydroxy-2-iodo-benzoic acid (2). Suspension of 2-amino-5-hydroxybenzoic acid (5.0 g, 32.7 mmol) in deionized water (100 mL) was mixed with 60 mL of concentrated sulfuric acid, which was added dropwise, resulting in a clear solution, which was held at 4° C. overnight, yielding suspension of white crystals. The suspension, while still cold, was mixed with 20 mL of an aqueous solution of sodium nitrite (2.4 g, 34.8 mmol). The resulting yellow-orange solution was mixed with 20 mL of an aqueous solution of potassium iodide (7.4 g, 44.6 mmol), which was added dropwise. The resulting mixture, dark-brown in color, was kept at 90° C. for 1 h and then was kept at 4° C. overnight affording dark red to brown crystals, which filtered off and redissolved in 100 mL of deionized boiling water. Activated charcoal (7 g) was added to the hot solution, which was held at 90° C. for 1 h. The slurry, while hot, was filtered off using filter paper (retention, 10 μm) and the supernatant was kept at 4° C. resulting in faintly orange crystals, which were filtered off and dried in a desiccator at r.t. $C_7H_5IO_3$, found (calc): C, 31.51 (31.84); H, 2.14 (1.91); I, 47.31 (48.07). $^1$H NMR (400 MHz, DMSO-$d_6$): δ 5.1 (s, 1H, OH), 6.81, 7.38, 7.71 ($H_3$, $H_5$, $H_2$, 1H each, in aromatic ring), 11 (s, 1 H, COOH). Yield, 3.2 g (37 mol %).

Synthesis of 5-[3-(Triethoxysilanyl)-propylcarbamoyloxy]-2-iodo-benzoic acid (3). Solution of 2 (264 mg, 1 mmol) and 5 mg of dibutyltin dilaurate in 100 mL of dry THF was mixed with 247 mg (1 mmol) of 3-isocyanatopropyltriethoxysilane and the resulting solution was kept under reflux at 70° C. for 8 h. Following solvent evaporation under vacuum and washing by hexane and drying under vacuum, the ensuing faintly yellowish paste weighed 460 mg (yield 90 mol %). $C_{17}H_{26}INO_7Si$, found (calc): C, 39.33 (39.93); H, 4.44 (5.12); I, 24.41 (24.82); N, 3.76 (2.74), $^1$H NMR (400 MHz, DMSO-$d_6$): δ 1.0 (m, C—$CH_2$—Si), 1.76 (m, $CH_3$), 2.94 (m, C—$CH_2$—N), 3.94 (m, C—$CH_2$—O), 7.14 (1H, $H_3$ benzene), 7.73 (d, $H_2$, $H_5$ benzene), 9.79 (1H, NH—C=O), 13 (1H, COOH).

Synthesis of Cellulose modified by iodoxybenzoic acid (IBX-Cellulose). Iodobenzoic acid derivative (3) (190 mg, 0.37 mmol) was dissolved in dry THF (20 mL) and the resulting solution was mixed with 190 mg (1 mmol) of microcrystalline cellulose. To the resulting suspension, 5 μl of deionized water were added and the suspension was refluxed while stirring at 70° C. for 16 h. To the suspension, Oxone® tetrabutylammonium salt (250 mg) in 1 mL THF and methanesulfonic acid (96 μL, 1 mmol) were added and reaction continued at 70° C. for 2 h. The solvents were then evaporated under vacuum; the resulting paste was suspended in water and dialyzed (membrane MW cut-off, 3500) against deionized water. The modified polymer was then filtered off, lyophilized and stored at −70° C. prior to the use. $C_{45}H_{72}INO_{32}Si$, found (calc., based on one (3-dimethylsilanyl-propyl)-carbamic acid 1-hydroxy-1,3-dioxo-1,3-dihydro-1$\lambda^5$-benzo[d][1,2]iodoxol-5-yl ester moiety per five glucose units), C, 39.30 (41.77); H, 6.16 (5.61); I, 9.56 (9.81); N, 1.09 (1.08); Si, 2.25 (2.17). $^1$H NMR (400 MHz, $D_2O$): δ 0.73 (m, Si—$CH_2$), 1.66, 1.78 (m, OH), 2.0 (m, OH), 3.0 (m, O—HC—C, pyran), 3.12, 3.22 (m, C—HC—C pyran), 3.88, 4.1, 4.18 (m, tetrahydropyran), 7.18, 7.45 (m, aromatic ring). FTIR (KBr): 3450 (bonded O—H . . . O), 2970 (—$CO_2^-$), 2860 ($CH_2$ stretch), 1730 (C=O stretch), 1610, 1570 (IBX vibrations), 1460 ($CH_2$), 1220 (C—O—C stretch), 1060 (C—O valence), 890 (Si—O stretch), 785 (Si—$CH_2$), 590 (aryl-I). Lei, Z.; Denecke, C.; Jegasothy, S.; Sherrington, D. C.; Slater, N. K. H.; Sutherland, A. J. *Tetrahedron Lett.* 2003, 44(8), 1635-1637. Determination of iodoxybenzoate groups was accomplished by isoniazid titration as described previously. Macalady, D. L.; Wolfe, N. L. *J. Agric. Food Chem.*, 1983, 31, 1139-1147. In brief, the polymer suspension was diluted by 10% sulfuric acid and a measured amount of isoniazid was added. Excess of potassium iodide was then added and the liberated iodine was titrated with 0.1 M thiosulfate in the presence of traces of starch near the end point. The presence of unmodified cellulose was not observed to interfere with the analysis. A content of IBX groups was determined to be 0.7 meq/g of dry cellulose.

Synthesis of Polyvinyl alcohol) modified with iodoxybenzoic acid (IBX-PVA). Solution of iodobenzoic acid derivative (3) (190 mg, 1.0 mmol) in dry THF (20 mL) was mixed with 222 mg (3 mmol per monomer) of PVA dissolved in 10 mL deionized water and the resulting mixture was kept at 70° C.

for 8 h. To the resulting opaque suspension, Oxone® tetrabutylammonium salt (300 mg) in 1 mL water and methanesulfonic acid (96 μL, 1 mmol) were added and reaction continued at 80° C. for 2 h. The suspension was then equilibrated at r.t. and dialyzed (membrane MW cut-off, 6000) against deionized water, lyophilized, and stored at −70° C. prior to use. $C_{27}H_{46}INO_{12}Si$, found (calc., based on one (3-dimethylsilanyl-propyl)-carbamic acid 1-hydroxy-1,3-dioxo-1,3-dihydro-1$\lambda^5$-benzo[d][1,2]iodoxol-5-yl ester moiety per six butan-2-ol units), C, 42.70 (44.32); H, 5.84 (6.34); I, 17.20 (17.35); N, 1.84 (1.91); Si, 3.65 (3.84). $^1$H NMR (400 MHz, $D_2O$): δ 0.89 (m, Si—$CH_2$), 1.28, 1.65 (m, C—$CH_2$ in the main chain), 1.79 (m, $CH_2$—C—Si), 3.01 (2H, $CH_2$—N), 3.82 (m, CH— in the main chain), 7.36, 7.41 (m, aromatic ring), 8.65 (1H, NH), $^{13}$C NMR (100.57 MHz, $D_2O$), δ 12.26 (>C—Si), 45.51 (methylene in the main chain), 59.31, 61.66 (methine in the main chain), 122.26, 127.34, 132.15 (aromatic ring), 162.73, 182.05 (>C=O). FTIR (KBr): 3450 (bonded O—H···O), 2930, 2860 ($CH_2$ stretch), 1730 (C=O stretch), 1620 (IBX vibrations), 1460 ($CH_2$), 1380, 1310, 1090 (C—O valence), 890 (Si—O stretch), 830 (Si—$CH_2$), 598 (aryl-I). Content of the IBX groups was determined to be 1.2 meq/g of dry PVA by the isoniazid titration.

Overview of Synthetic Route. In the synthetic route described herein, 2-amino-5-hydroxybenzoic acid (1) was converted into 5-hydroxy-2-iodobenzoic acid (2) by a Sandmeyer reaction (Scheme 3). The 2-iodobenzoic acid is a convenient synthetic source of IBX, and thus the 5-hydroxy-2-iodobenzoic acid will combine an OH group as an available linking handle with the easy conversion into an IBX derivative. Schulze, A.; Giannis, A., *Synthesis*, 2006, No. 2, 257-260; Frigerio, M.; Santagostino, M.; Sputore, S. *J. Org. Chem.*, 1999, 64(12), 4537-4538.

Compound (2) was thus linked to a commercially available reagent, bifunctional 3-isocyanatopropyltriethoxysilane by a urethane bond, in a water-free organic solvent, affording a 5-[3-(triethoxysilanyl)-propylcarbamoyloxy]-2-iodo-benzoic acid (3) (Scheme 4).

Scheme 3.
Synthesis of 5-hydroxy-2-iodobenzoic acid (2).

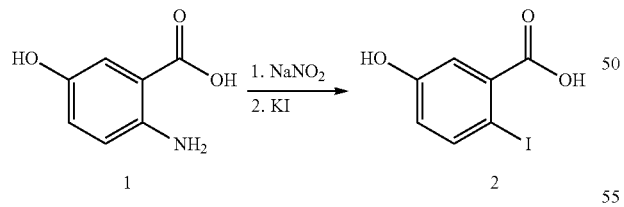

Compound (3) was then conjugated to a substrate by a water-catalyzed sol-gel process (Scheme 5). The iodobenzoic groups were converted into IBX by Oxone® (2 $KHSO_5$—$KHSO_4$—$K_2SO_4$) in combination with methanesulfonic acid (Scheme 5 and FIG. 18). Sorg, G.; Mengel, A.; Jung, G.; Rademann, J., *Angew. Chem. Int. Ed.*, 2001, 40 (23) 4395-4397. Judging by the presence of strong carbonyl vibration bands around 2970 and 1730 $cm^{-1}$ in the FTIR spectra (FIG. 12) of the modified polymers, significant fractions of the hydroxy groups on cellulose or PVA were oxidized to carbonyl groups in the process of the IBX formation.

Scheme 4.
Synthesis of 5-[3-(Triethoxysilanyl)-propylcarbamoyloxy]-2-iodobenzoic acid (3).

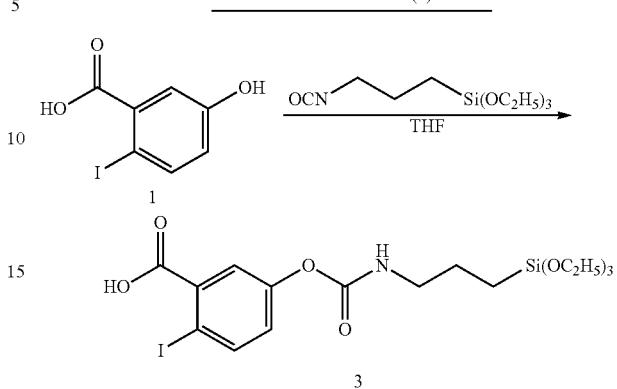

Scheme 5. Synthesis of IBX-modified polymers.

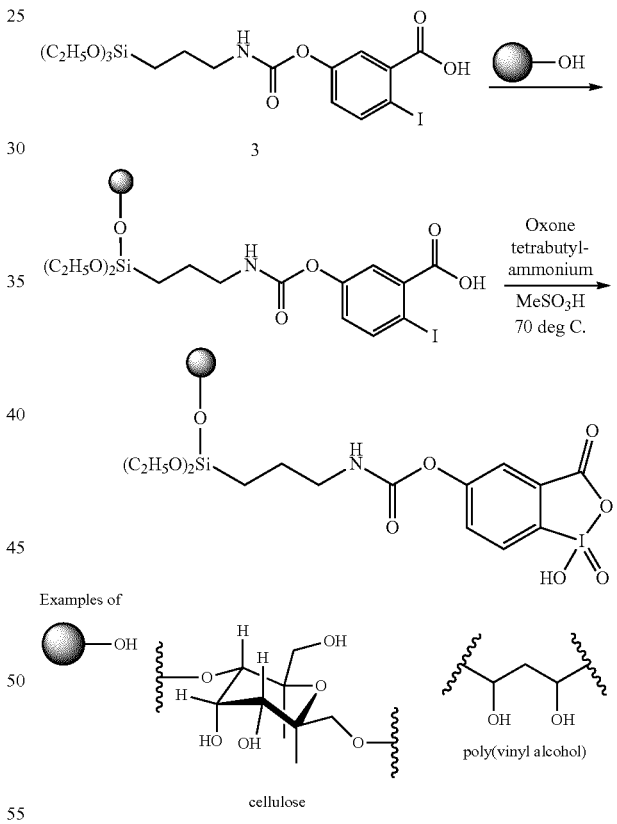

Figure 18:
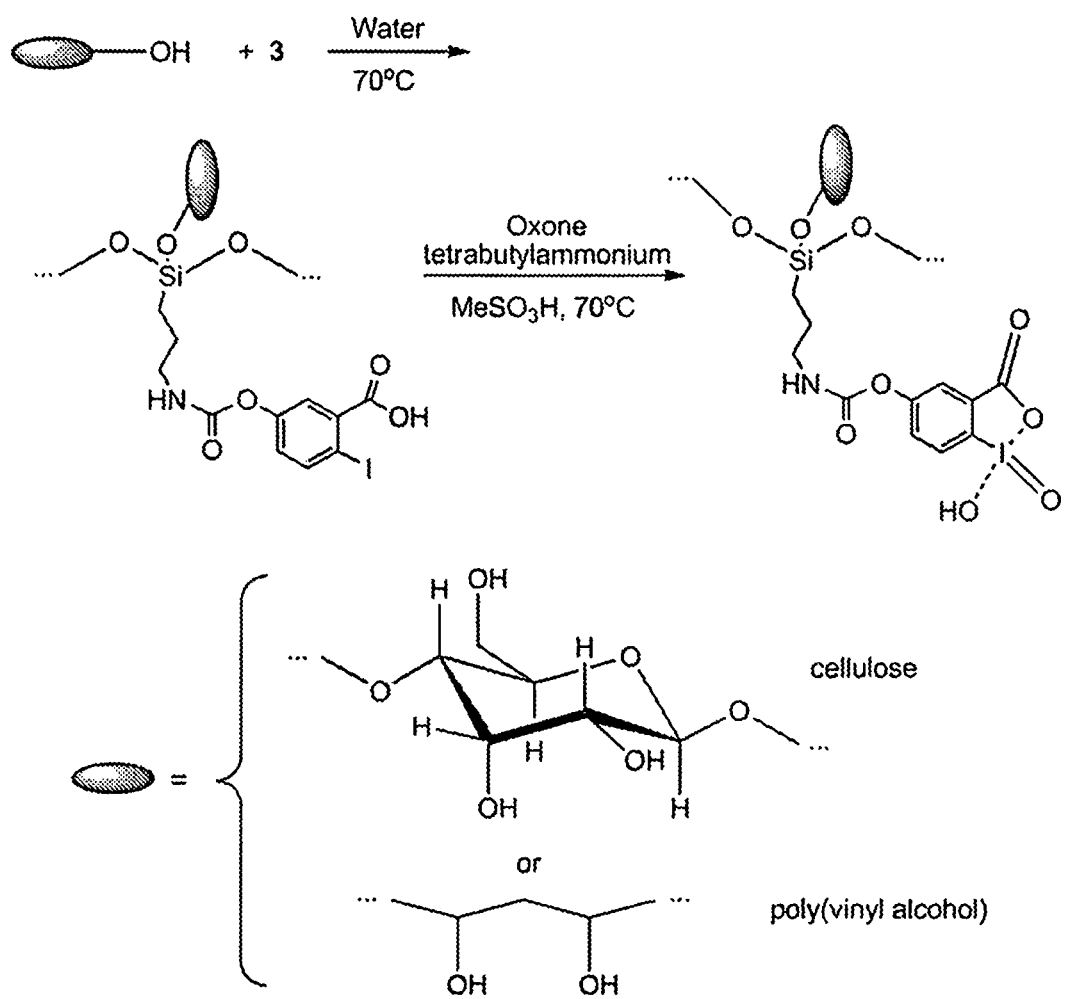
FIG. 18 depicts a synthesis of IBX-modified polymers.

Contrary to what is shown in Scheme 5, the sol-gel reaction resulted in formation of silica clusters (Scheme 6) conjugated with the polymers (FIG. 18). The silica formation resulted in the formation of PVA nanoparticles modified with IBX groups (IBX-PVA) with the weight-average diameter of 173±8 nm (n=10) assessed through the DLS measurements. Dynamic light scattering (DLS) experiments were performed with a Brookhaven B1-200SM light scattering system at a measurement angle of 90°. Weight-average particle size distributions were obtained using the built-in software and the reported particle hydrodynamic diameters are the average of ten measurements. The samples were filtered with a 0.45 μm syringe filter prior to the DLS tests.

Additionally, silica domains on the surface of the modified cellulose particles (average size, ~20 μm) could be seen on the SEM images. Cellulose particles, modified and unmodified, were visualized using a Jeol ISM-6060 Scanning Electron Microscope. Samples were mounted on double-sided tape on aluminum stubs and sputter-coated with gold, and micrographs were taken at appropriate magnification.

FTIR were recorded in KBr using a Nexus 870 spectrometer (Thermo Nicolet Corp., Madison, Wis.) in absorbance mode by accumulation of 256 scans with a resolution of 4 cm$^{-1}$. FIG. 12 depicts the FTIR spectra of IBX-Cellulose (top) and IBX-PVA (bottom) in relation to their unmodified counterparts.

accelerate the reduction of the 2-iodoxybenzoate to 2-iodoso- and 2-iodobenzoates. Frigerio, M.; Santagostino, M.; Sputore, S. *J. Org. Chem.,* 1999, 64(12), 4537-4538.

Figure 11:
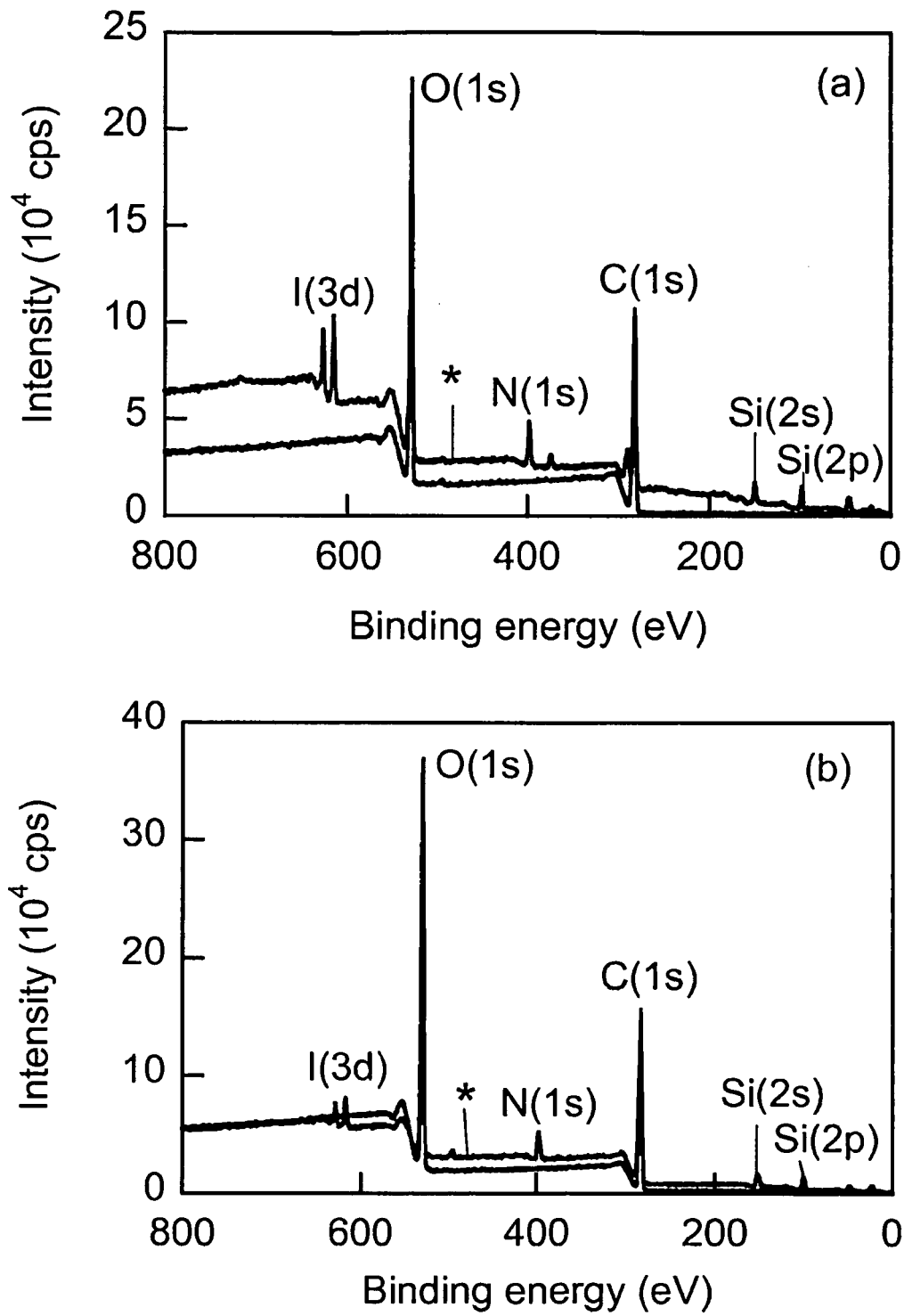
FIG. 11 depicts XPS spectra of dry particles of PVA and IBX-PVA (a) and cellulose and IBX-cellulose (b). Spectra of the IBX-modified species are marked by an asterisk (*).

The survey XPS scans of IBX-modified and unmodified PVA- and cellulose-based particles all showed major core signals of C(1s) and O(1s) centered at 282 and 529 eV, respectively (FIG. 11). In the IBX-modified particles, iodine I(3d) signals at 629 and 615 eV belonging to the iodoxy group were observed, along with the Si(2s) and Si(2p) signals at 150 and 98 eV, respectively, due to the presence of silica on the particle surface. The nitrogen signal, N(1s), at 398 eV, indicated the presence of the urethane group in the polymer-silicone linkage (Scheme 5). Interestingly, the relative iodine content in the IBX-modified particles found from the XPS iodine/carbon ratio was 1.4- to 5-fold smaller than the one obtained

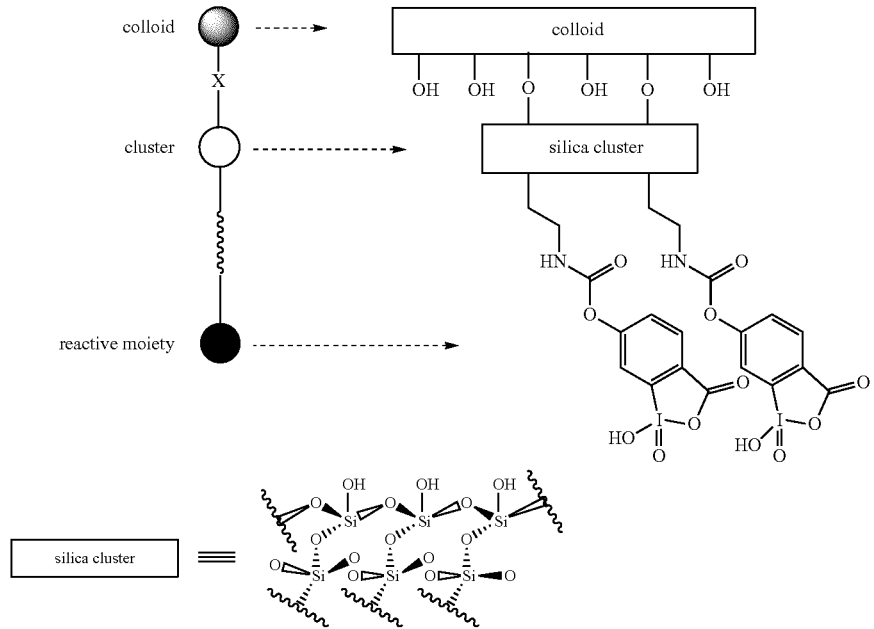

Scheme 6. Formation of polymer-silica hybrid substrates functionalized by IBX groups.

Particles of the IBX-modified cellulose and IBX-PVA were observed to possess ζ-potentials of −6.92±1.07 (n=20) and −9.12±0.98 (n=20) mV, respectively, in aqueous suspensions with pH above 3. The attached IBX groups (pK$_a$=2.40) contributed to the negative ζ-potential of these substrates. Gallen, M. J.; Goumont, R.; Clark, T.; Terrier, F.; Williams, C. M. *Angew. Chem. Int. Ed.,* 2006, 45(18), 2929-2934. The Oxone converts 2-iodo- and 2-iodosobenzoic acid into IBX, which in turn oxidizes alcohols into aldehydes and ketones, but the resulting 2-iodosobenzoic acid is then converted back into IBX by the excess Oxone. Schulze, A.; Giannis, A., *Synthesis,* 2006, No. 2, 257-260; Frigerio, M.; Santagostino, M.; Sputore, S. *J. Org. Chem.,* 1999, 64(12), 4537-4538; de Munari, S.; Frigerio, M.; Santagostino, M., *J. Org. Chem.,* 1996, 61, 9272-9279. That would explain the observed stability of the IBX groups on the modified polymers in 10% aqueous suspensions for at least 4 weeks when kept in contact with 1 wt % Oxone tetrabutylammonium salt at room temperature, as judged by the unchanged results of the isoniazid titration. Exposing IBX moieties in water to elevated temperatures above 60-70° C., in the absence of Oxone but in the presence of the hydroxyl groups on the polymer, would dramatically from elemental analysis, whereas the silicone/carbon ratio value obtained from XPS was approximately 4-fold larger than the one found from the elemental analysis. These data indicate that the surface of the particles was enriched by the silicone, which also lowered the relative surface content of the IBX groups.

Unless otherwise noted, XPS measurements were carried out on vacuum-dried particle samples with a Kratos Axis Ultra Imaging X-ray photoelectron spectrometer (Kratos Analytical Ltd., Manchester, UK) equipped with a monochromatized A1 Kα X-ray source operated at 150 W with a spot of 300×700 μM. The base pressure was better than 1×10$^{-9}$ Torr and the analysis pressure better than 2×10$^{-8}$ Torr. Survey spectra (0-1100 eV BE range) were collected at 90° take off angle (with respect to the sample surface) and pass energy of 160 eV.

Importantly, the IBX is insoluble in most organic solvents (except DMSO) at r.t., and thus its conjugation with water- and solvent-dispersible polymers is a potential means to create an efficient, "green" oxidation catalyst. Thottumkara, A. P.; Vinod, T. K. *Tetrahedron Lett.* 2002, 43(4), 569-572.

Almost all of the IBX groups present in the particles were accessible to titration, which yielded effective IBX concentrations of 0.7 and 1.2 meq/g for cellulose-IBX and PVA-IBX, respectively. These results corresponded well with those afforded by elemental analysis (0.77 and 1.31 meq/g for cellulose-IBX and PVA-IBX, respectively) and were comparable to the typical capacities of previously reported resin-supported IBX reagents. Sorg, G.; Mengel, A.; Jung, G.; Rademann, J., *Angew. Chem. Int. Ed.*, 2001, 40 (23) 4395-4397.

A simple strategy toward modification of polymer particles with surface hydroxyls or amino groups by the o-iodoxybenzoyl (IBX) groups, capable of both hydrolyzing electrophilic organophosphates and oxidizing thiophosphate groups in the presence of water, was described. The synthetic route involved first creating a "handle" having an iodobenzoic acid on one terminus and reactive alkoxysilanyl groups on the other. The "handle" was capable of incorporating the —OH groups on the polymer surface via sol-gel reaction in the presence of water, which in parallel created organic-inorganic particles because of the formation of silica conjugated to the polymer. In this example, the synthetic route involved modification of 5-hydroxy-2-iodo-benzoic acid with 3-isocyanatopropyltriethoxysilane in non-aqueous solvent followed by conjugation of the resulting triethoxysilanylpropylcarbamoyloxy-iodobenzoic acid with the —OH groups of the polymers via sol-gel reaction in the presence of water. The iodobenzoic groups on the particle surface were further oxidized by Oxone® tetrabutylammonium salt into IBX, a process that is likely to also oxidize available hydroxyl groups on the particle into carbonyls. The formation of silica conjugated to the polymer created organic-inorganic particles. No pre-treatment derivatization of the polymer or particle was required, which is an advantage of the developed synthetic route.

Example 2

Performance of Iodoxybenzoate (IBX)-modified Substrates in Decomposition of Diisopropylfluorophosphate (DFP), a Nerve Agent Stimulant

DFP

Kinetics of the DFP decomposition were measured at 25° C. with an Orion 96-09 combination fluoride electrode (Thermo Electron Corp., Waltham, Mass.) and a Model 45 Dual Display Multimeter (Fluke Corp., Everett, Wash.) connected to a PC with FlukeView Forms software for data processing. The electrode was immersed in a stirred 9-mL aqueous sample and the electrode potential-time output was recorded continuously. No significant changes in pH, set initially at 7.4, were observed in any of the runs. The electrode was calibrated in an independent series of experiments using aqueous solutions of sodium fluoride.

Hydrolysis of DFP, which is a close analog of the warfare OP agents sarin and soman, was studied by the monitoring of the appearance of the DFP decomposition product, fluoride ion, using an ion-selective electrode. Bromberg, L.; Hatton, T. A. *Ind. Eng. Chem. Res.;* 2007, 46(10), 3296-3303.

The hydrolysis of DFP in suspensions of IBX-containing particles in most cases was studied under conditions of excess of hydrolytic groups over the initial substrate concentration ($[IBX]_o > [DFP]_o$). Under these conditions and at pH maintained constant and neutral by the Tris buffer, the DFP hydrolysis is well-established to be a pseudo-first order reaction. Bromberg, L.; Hatton, T. A., *Ind. Eng. Chem. Res.;* 2005; 44(21), 7991-7998. The fluoride electrode potential was converted to the time-dependent fluoride concentration ($C_t$) readings using electrode calibration curves in sodium fluoride solutions. FIG. 1 shows time vs DFP conversion kinetics, which depended on the effective polymer concentration. The initial slope of the $C_t$ vs t kinetic curves gives the initial rate of the DFP hydrolysis ($v_o$), while the rate constants for the DFP hydrolysis ($k_{obs}$) were obtained from the experimental data using the equation:

$$-\ln(1 - C_t/[DFP]_o) = k_{obs} t \qquad (1)$$

where $[DFP]_o$ is the initial concentration of the substrate.

Figure 2:
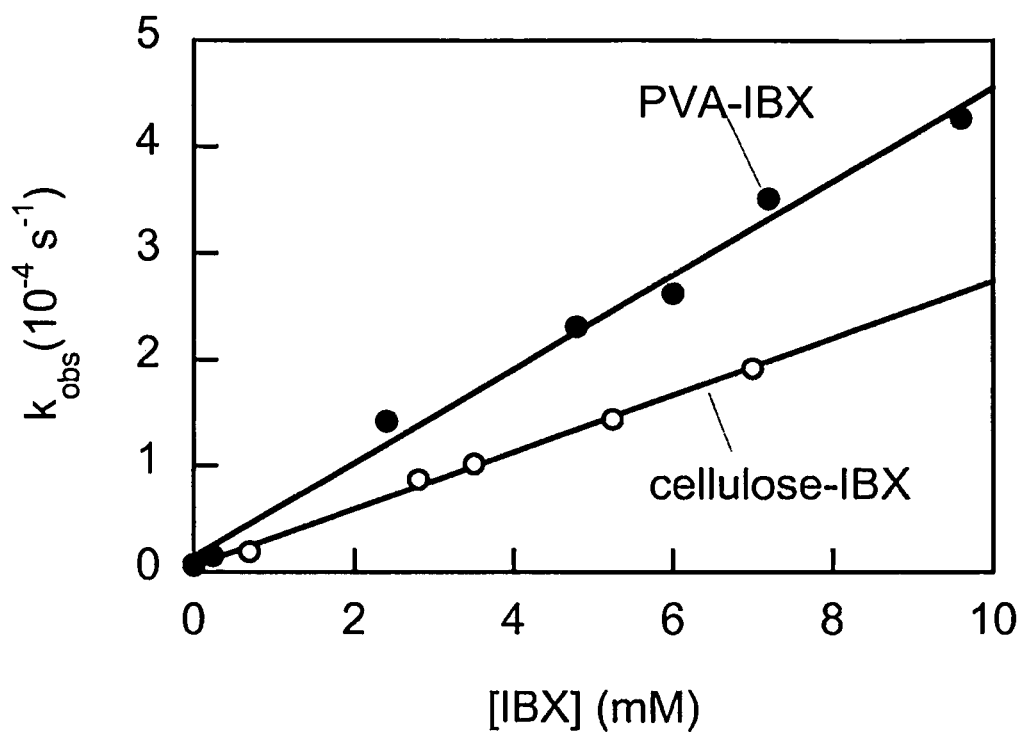
FIG. 2 depicts the observed kinetic constants of DFP hydrolysis ($k_{obs}$) versus effective concentration of iodoxybenzoate (IBX) groups in particle suspensions. [DFP]$_o$=6 mM, pH 7.4, 50 mM Tris buffer, T=25° C.

The observed rate constants for unmodified polymers devoid of IBX groups were measured to be $7.3 \times 10^{-6}$ and $6.0 \times 10^{-6}$ s$^{-1}$ for PVA and cellulose, respectively, which corresponded well with the previously reported values for spontaneous DFP hydrolysis at similar pH and temperature values. Bromberg, L.; Hatton, T. A., *Ind. Eng. Chem. Res.;* 2005; 44(21), 7991-7998. FIG. 2 shows the dependencies of the observed rate constant on the effective concentration of the IBX groups in the polymer suspensions under study.

The $k_{obs}$ vs $[IBX]_o$ plots were linear ($R^2 > 0.987$ in both cases), confirming the pseudo-first order kinetics. The slopes of the linear fits yielded the apparent second-order rate constants (k") for the nucleophilic hydrolysis of DFP to be $4.6 \times 10^{-2}$ and $2.7 \times 10^{-2}$ M$^{-1}$s$^{-1}$ for IBX-PVA and IBX-Cellulose, respectively. These rates show a significant hydrolytic activity.

In summary, the IBX-modified poly(vinyl alcohol) and microcrystalline cellulose were shown to be capable of hydrolyzing diisopropyl fluorophosphate (DFP), an analog of sarin and soman, at pH 7.4 with the apparent second-order rate constants (k") of $4.6 \times 10^{-2}$ and $2.7 \times 10^{-2}$ M$^{-1}$s$^{-1}$, respectively. These rates are more than 100-fold over those of spontaneous hydrolysis with unmodified colloids.

Although these rates indicate a significant hydrolytic activity, they were approximately an order of magnitude lower than those reported previously with pralidoxime-modified magnetite nanoparticles and were roughly equal to those with particles modified with polymers containing 4-vinylpyridine-N-phenacyloxime groups, which is in accord with the notion that IBX is a weaker nucleophile than the IBA and activated oximates. However, the ability of IBX to perform as both an oxidant and a nucleophile was yet to be explored. Thus, the effect of the IBX-modified particles on a phosphorothioate such as chlorpyrifos that could be partially oxidized was studied next.

Example 3

Performance of Iodoxybenzoate (IBX)-modified Colloids in Decomposition of Chlorpyrifos and Chlorpyrifos Oxon, Toxic Pesticides and Nerve Agent Stimulants The rate of CP hydrolysis was measured as follows. Macalady, D. L.; Wolfe, N. L. *J. Agric. Food Chem.*, 1983, 31, 1139-1147. A stock solution of CP or CPO in methanol (0.004 mg/mL, 1.0 mL total) was placed in a borosilicate screw-cap vial and was allowed to evaporate under a stream of nitrogen. Then a suspension of cellulose or IBX-cellulose, or a solution of IBX-PVA or PVA (2 mL total, polymer concentration, 1.0 mg/mL, pH 7.4) was added, the vial was sonicated for 5-6 s, and the hydrolysis experiment commenced. The effective concentration of CP measured in the aqueous sample corresponded to the reported solubility of the CP in water, 2 mg/L. Baskaran, S.; Kookana, R. S.; Naidu, R., *Pesticide Sci.* 1999, 55, 1222-1228.

The vials were shaken at 200 rpm at 25° C. and at a certain time interval, a vial was removed, contents quenched by acidification via adding 5 µL of 1 M HCl, and then 10 mL of 0.1 µM solution of TCB (internal reference) in isooctane were added. The mixture was vortexed for 30 s and placed in a refrigerator (4° C.) to allow components to separate before analysis. The isooctane layer was subsequently separated and subjected for analysis for the CP or CPO content. The isooctane extracts from the time course samples were analyzed, in duplicate, by GC, and the concentration of the substrate remaining at each time point was calculated from a standard plot of peak integration ratios vs concentration. The GC setup comprised a Perkin Elmer Clarus 500 GC (ECD, 300° C.) equipped with an Rxi™-5 ms column (30 m, 0.25 mm ID, 0.25 µM film thickness). Injection: 1.0 mL splitless; injector temperature: 220° C.; carrier gas: helium, constant flow; linear velocity, 40 cm/s, 100° C.; oven temperature: 100° C. (hold 1 min) to 295° C. at 25° C./min (hold 7 min).

Scheme 7. Main degradation pathways of chlorpyrifos in the presence of IBX-modified substrates. The 3,5,6-trichloro-2-pyridinol product is accompanied by phosphate products.

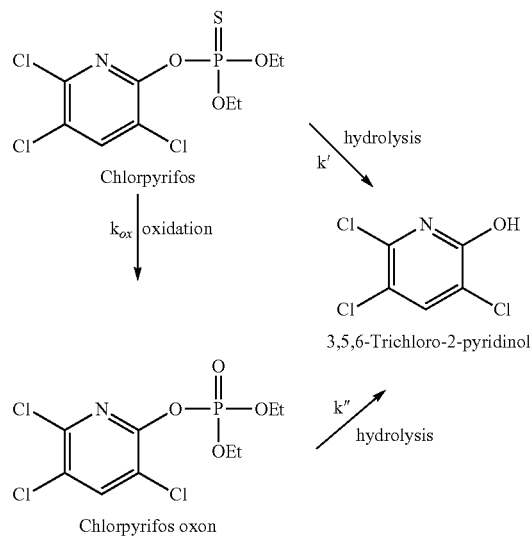

Chlorpyrifos is among the most widely utilized organophophosphorothioate pesticides. Primary degradation pathways of chlorpyrifos (CP) in aqueous milieu with pH close to neutral include both a direct CP hydrolysis into 3,5,6-trichloro-2-pyridinol (TCP) as well as an oxidation of the CP thiophosphate group (P=S) to its corresponding oxon (P=O) (Scheme 7). Freed, V. H.; Chiou, C. T.; Schmedding, D. W. *J. Agric. Food Chem.,* 1979; 27(4); 706-708; Racke, K. D.; Steele, K. P.; Yoder, R. N.; Dick, W. A.; Avidov, E. *J. Agric. Food Chem.,* 1996, 44(6), 1582-1592; Duirk, S. E.; Collette, T. W. *Environ. Sci. Technol.,* 2006, 40(2), 546-551; Seger, M. R.; Maciel, G. E., *Environ. Sci. Technol.,* 2006, 40(3), 791-796; Seger, M. R.; Maciel, G. E. *Environ. Sci. Technol.,* 2006, 40(3); 797-802. The contributions of the hydrolysis and oxidation processes in the chlorpyrifos degradation are greatly enhanced in the presence of hypochlorous acid and free chlorine. The chlorpyrifos oxon (CPO) is 1000-fold more toxic than CP, but its degradation is typically faster than the parent CP. Wu, J.; Laird, D. A. Environ. Toxicol. Chem., 2003, 22(2), 261-264.

Figure 3:
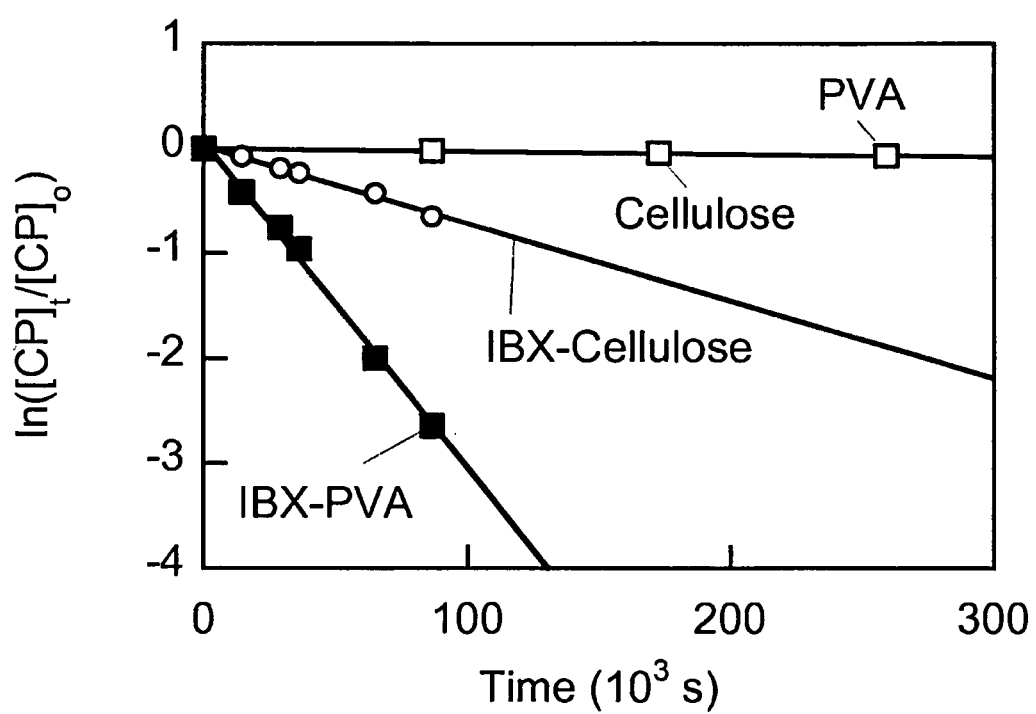
FIG. 3 depicts kinetic data from chlorpyrifos (CP) hydrolysis in 1 mg/mL aqueous suspensions of unmodified cellulose and PVA and modified IBX-PVA and IBX-Cellulose. [CP]$_o$=5.7 µM, pH 7.4, T=25° C.
Figure 4:
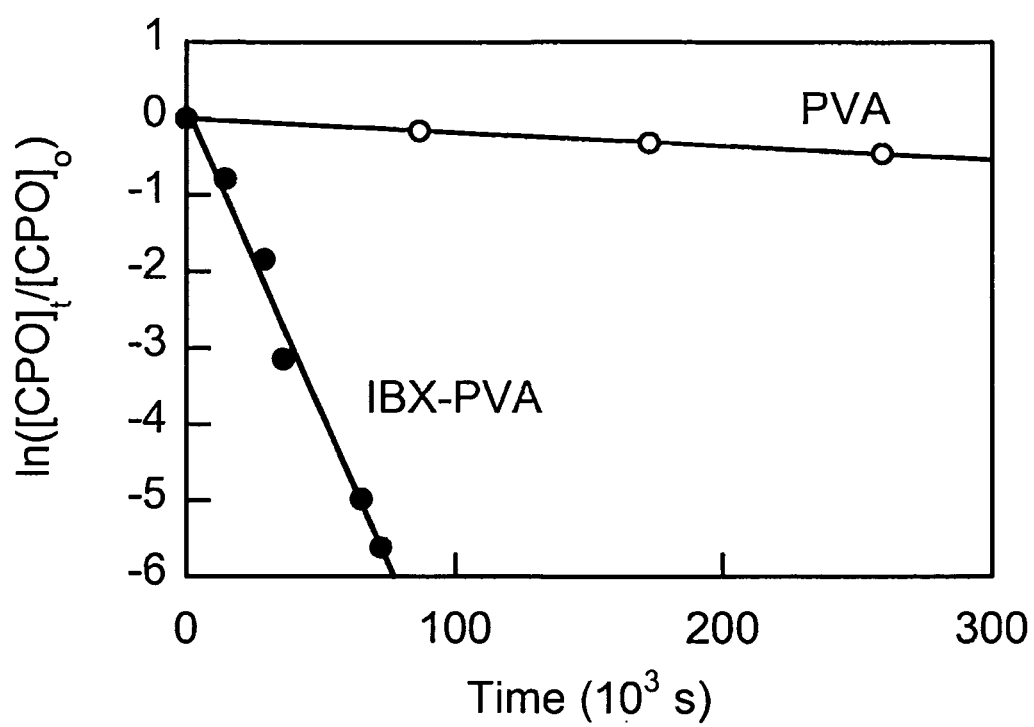
FIG. 4 depicts kinetic data from chlorpyrifos oxon (CPO) hydrolysis in 1 mg/mL aqueous suspensions of unmodified PVA and modified IBX-PVA. [CPO]$_o$=6.0 µM, pH 7.4, T=25° C.

Kinetics of the CP and CPO degradation in the presence of the IBX-modified particles and their unmodified counterparts under the pseudo-first-order condition of the initial IBX concentration exceeding that of CP or CPO are given in FIGS. 3 and 4. The observed loss of CP and CPO in the presence of IBX was observed to be first order with respect to the substrate concentration, as was evidenced from the linearity of the ln(remaining substrate fraction) vs time plots ($R^2 > 0.99$ in all experiments). The slopes of the linear fits in FIGS. 3 and 4 yielded the observed rate constants, $k_{obs}$ (compare eqn(2) below with eqn(1)):

$$\ln([CP]_t/[CP]_o) = -k_{obs} t \qquad (2)$$

Thus measured $k_{obs}$ enable estimate of the substrate half-lives ($t_{1/2} = 0.693/k_{obs}$) under different conditions, an important practical parameter often reported in the literature. The apparent second order rate constant, k", also often cited, is related to the $k_{obs}$ via the initial IBX concentration ($k'' = k_{obs}/[IBX]_o$).

For comparison, in FIG. 17 are collected the $t_{1/2}$ and k" values for CP and CPO degradation measured in the present work as well as literature data collected under varying conditions. Noblet, J. A.; Smith, L. A.; Suffet, I. H. *J. Agric. Food Chem.,* 1996; 44(11), 3685-3693; Brzak, K. A.; Harms, D. W.; Bartels, M. J.; Nolan, R. J. *J. Anal. Toxicol.,* 1998, 22(3), 203-210; Duirk, S. E.; Collette, T. W. *Environ. Sci. Technol.,* 2006, 40(2), 546-551; Baskaran, S.; Kookana, R. S.; Naidu, R., *Pesticide Sci.* 1999, 55, 1222-1228.

A 26- and 122-fold acceleration of the CP degradation was observed in the IBX-Cellulose and IBX-PVA suspensions compared to the corresponding unmodified cellulose and PVA suspensions, respectively. Likewise, an almost 43-fold acceleration of the CPO degradation was measured in the IBX-PVA suspensions compared to the corresponding PVA solutions. It is also noteworthy that the degradation of CPO was several-fold faster than that of CP. The observed effect of the colloid modification with the IBX groups, combined with the simplicity of the modification process and the environmentally friendly nature of the IBX make the IBX-modified colloids a viable route toward creating decontaminating surfaces.

Figure 13:
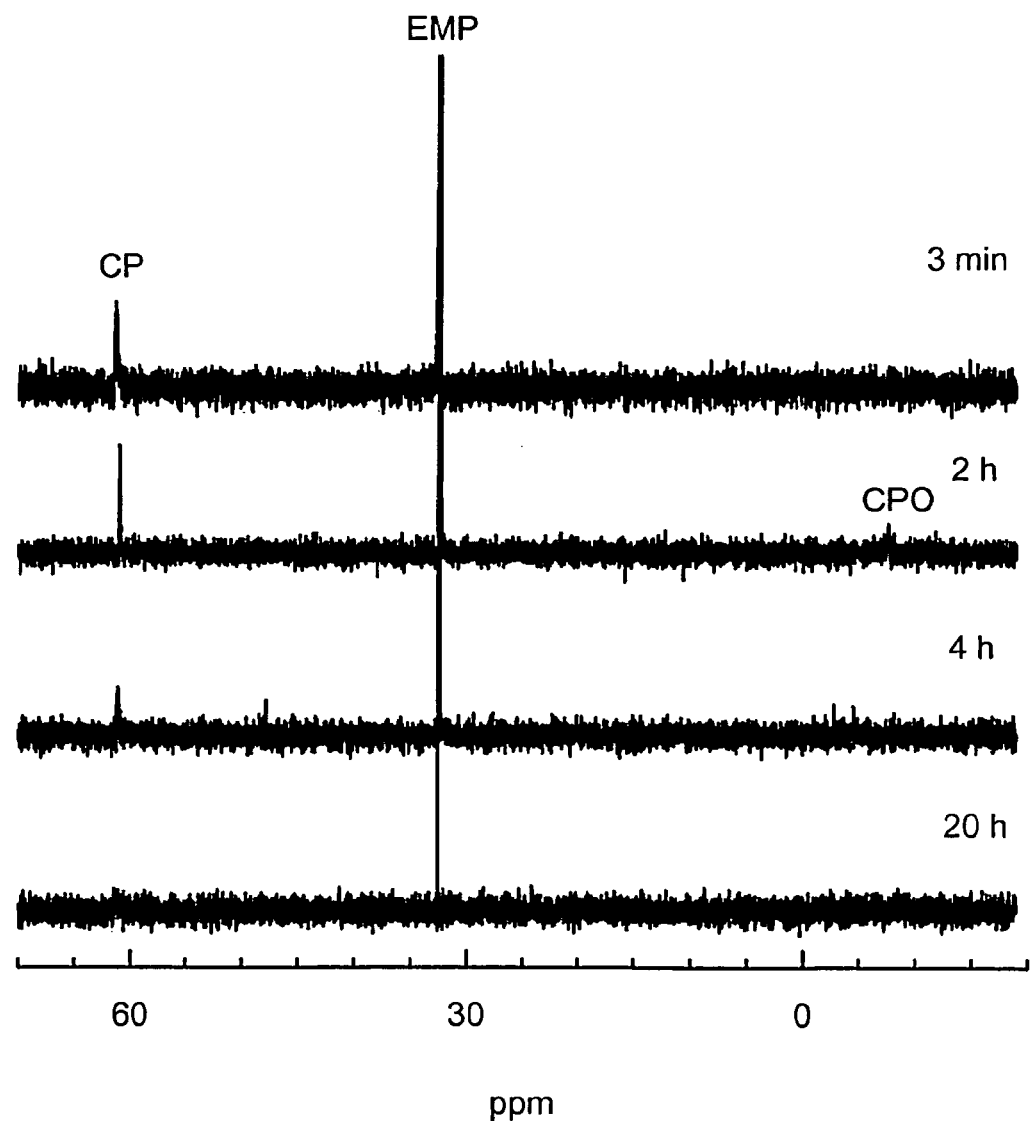
FIG. 13 depicts 161.98 MHz $^{31}$P NMR spectra of chlorpyrifos ([CP]$_o$=34 mM) in a 10 mg/mL IBX-PVA suspension in D$_2$O (pD 7.4, 25° C.) taken at various time intervals. EMP and CPO stand for ethylmethyl phosphonate (external probe) and chlorpyrifos oxon, respectively.
Figure 14:
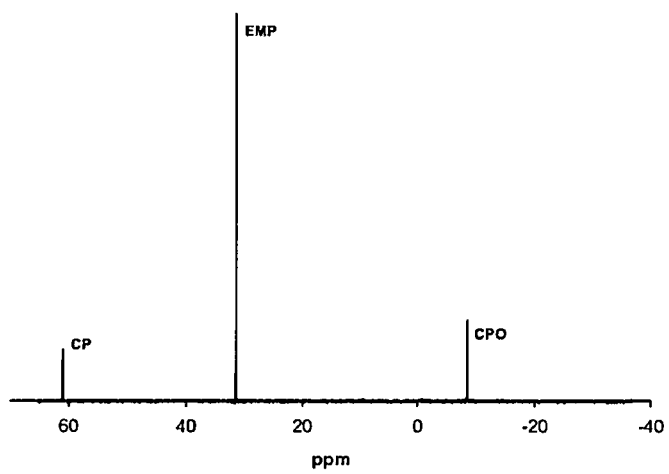
FIG. 14 depicts a 161.98 MHz $^{31}$P NMR spectrum of chlorpyrifos (CP) and chlorpyrifos (CPO) in CD$_3$OD. External probe, ethylmethyl phosphonate (EMP) solution in D$_2$O.
Figure 15:
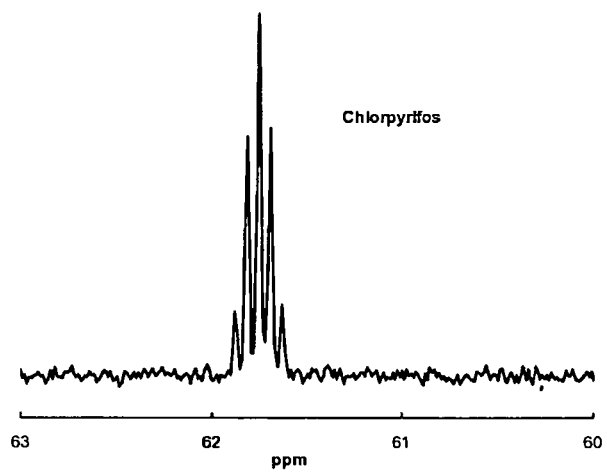
FIG. 15 depicts a detailed view of the $^{31}$P NMR peak of chlorpyrifos in CD$_3$OD.
Figure 16:
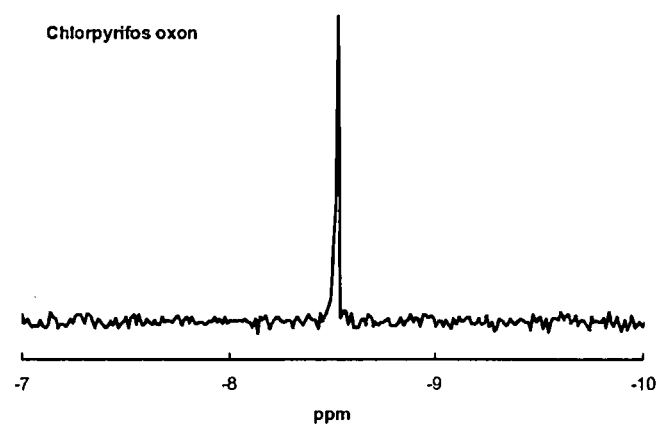
FIG. 16 depicts a detailed view of the $^{31}$P NMR peak of chlorpyrifos oxon in CD$_3$OD.

NMR experiments were conducted in order to reveal the hydrolytic and oxidizing capabilities of the IBX-modified polymers. Because of the presence of the substrate-adsorbing particles in the suspensions (which create field inhomogeneities in the sample), the experiments were limited to the use of relatively high initial concentrations of the CP and CPO substrates. Moreover, because of the need to observe the formation of the CPO, which is created by, the non-catalytic, stoichiometric reduction of IBX into IBA groups, a relatively high polymer concentration yielding an IBX concentration capable of producing a significant CPO concentration over the course of the CP oxidation was used. This, in turn, ruled out a study of cellulose suspensions with a large particle size of ~20 gm. However, the processes occurring in suspensions of the IBX-PVA particles (average diameter, 173 nm; see above) with initial effective CP and IBX concentrations of 34 and 12 mM, respectively, were examined. Typical $^{31}$P NMR spectra taken on such a system are shown in FIG. 13. More detailed $^{31}$P NMR spectra are depicted in FIGS. 14, 15, and 16.

The CP peak observed at 61.3-60.8 ppm diminished in the course of the CP degradation, giving rise to the CPO peak seen at −8.1 ppm (spectrum taken at 2 h). The CPO peak split into several small peaks (below 2×S/N) after 2.5 h and disappeared in the spectra taken after 4 h. Minor peaks belonging to products of the CP degradation such as O=P(OR)(OAr)(SH) and O=P(OH)$_3$ were observed at 47.3 and −3.3 ppm, respectively, after 4 h. Duirk, S. E.; Collette, T. W. *Environ. Sci. Technol.*, 2006, 40(2), 546-551. After about 20 h, all internal peaks disappeared indicating that the decomposition products containing phosphorus adsorbed on the particles, thus undergoing motional averaging.

In summary, the IBX-Cellulose and IBX-PVA suspensions accelerated chlorpyrifos degradation 26- and 122-fold compared to the corresponding unmodified cellulose and PVA suspensions, respectively. Approximately 43-fold acceleration of the chlorpyrifos oxon degradation was measured in the IBX-PVA suspensions compared to the corresponding PVA solutions. The IBX-modified particles were capable of oxidizing the thiophosphate (P=S) group to the corresponding oxon (P=O), a feature potentially useful in demilitarizing combat nerve agents such as VX. Because it involves a versatile and benign agent that can be applied to a wide variety of surfaces, the developed modification route is appropriate and feasible for a wide variety of chemical defense applications.

Example 4

Synthesis of Magnetic Colloids

Applications of magnetic particles in aqueous media require colloidal stability and recyclability of the particles. Particles can be stabilized colloidally by steric or electrostatic interactions or both. Small particles offer large surface areas and a resulting ability to present more functional groups than is possible with larger particles of the same total weight. However, individual magnetic particles with sizes less than 10 nm are not efficiently captured by HGMS because of the small magnetic force acting on the particles and the relatively strong diffusive forces resulting from the particle concentration gradient. However, it has been shown that magnetic nanoparticle clusters with a hydrodynamic diameter larger than 50 nm, can be effectively captured by HGMS.

Particle precipitation took place in the presence of a random copolymer of acrylic acid (AA), vinylsulfonic acid sodium salt (VSA), and 4-styrenesulfonic acid sodium salt hydrate (SSA) with the molar ratio of 2:1:1. The pKa is 4.25, 0.53, and 0.60 for AA, vinyl sulfonic acid, and 4-styrenesulfonic acid, respectively, based on titration measurement. The last two pKa values were calculated by SPARC online property calculator. The AA-VSA-SSA copolymer was prepared according to a published procedure. In brief, 1.05 g of AA, 3.79 g of VSA solution, and 1.5 g of SSA were mixed with 0.1 g of potassium persulfate as initiator and 0.4 g of sodium metabisulfite as chain transfer agent. The solution volume was adjusted to 22 mL by addition of water. Reaction was kept at 80° C. for 3 hr. The prepared polymer was characterized with GPC to measure the molecular weight. The prepared polymer solution was used directly for the particle synthesis without further purification.

Figure 5:
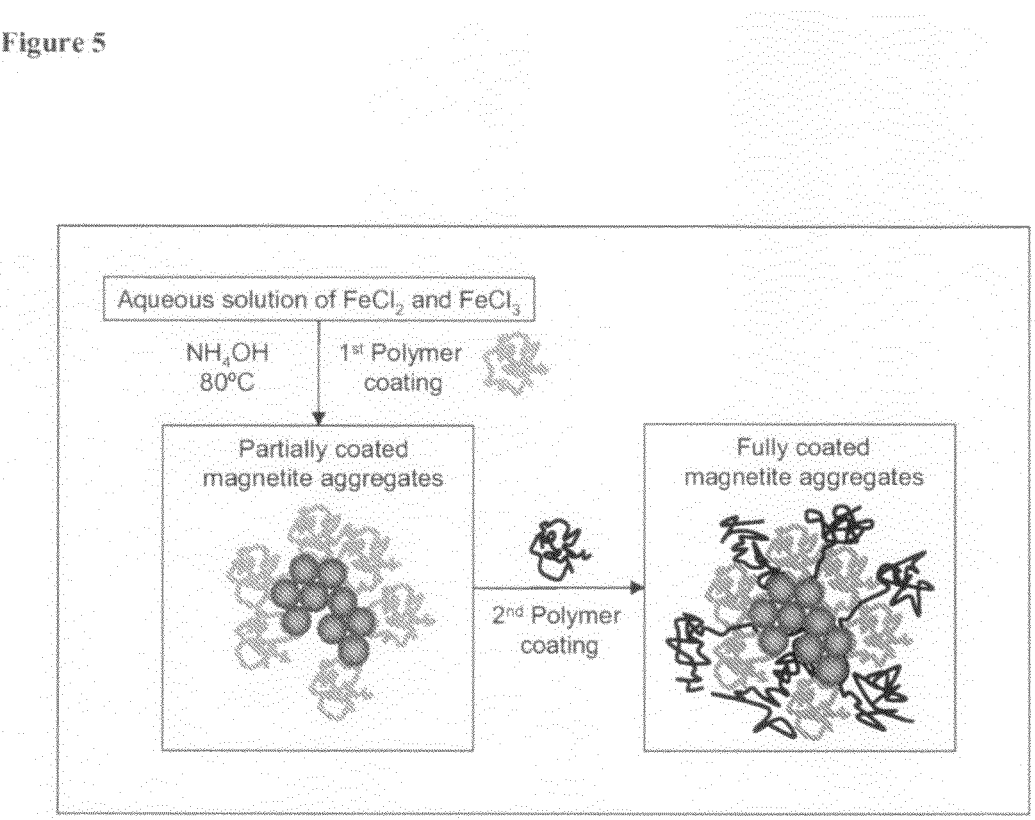
FIG. 5 depicts a synthesis of magnetic aggregates.

Magnetic nanoclusters of primary magnetite particles (~6 nm in diameter) were synthesized according to the published two-step procedure. In brief, 40 mL of water was added into three-neck flask and deaerated by nitrogen bubbling for 30 min. Then iron(II) chloride tetrahydrate (0.86 g, 4.3 mmol) and iron(III) chloride hexahydrate (2.36 g, 8.6 mmol) were dissolved into the deoxygenated water and the resulting solution was heated to 80° C. 2.5 mL of the previously prepared AA-VSA-SSA terpolymer solution was mixed with 6 mL of 28% aqueous ammonium hydroxide and the mixture was quickly added to the iron salt solution, at which point the solution immediately turned black due to the formation of magnetite particles. The dispersion was stirred for 15 min. Then 1 g of aqueous 50% poly(acrylic acid) solution was added to the magnetite dispersion as a secondary polymer and the resulting dispersion was kept at 80° C. with stirring for another 15 min. After cooling, the particle dispersion was mixed with 50 mL of acetone. The particles were removed from the supernatant by attracting them to an electromagnet and decanting the solution. The particles were then re-dispersed into 50 mL of water and decanted after mixing with 50 mL of acetone. This was repeated for a total of three times. The particles were finally dried under vacuum until a constant weight was attained. Then the particles were re-dispersed in 50 mL of deionized water and sonicated for 1 min using a Branson Sonifier Model 450 at 40% power output. The particle concentration was 20 mg/mL. These particles are referred as the "original particles" in the following discussion. Magnetic particle synthesis is shown in FIG. 5.

In summary, in this process, Fe(II) and Fe(III) salts are dissolved in water. Salt solution is purged with nitrogen for thirty minutes. When the solution is heated up to 80° C., certain amount of first polymer is added simultaneously with ammonium base into the solution to form the magnetite cores. However, added polymer is not enough to stabilize all individual magnetic cores, they will form aggregates after the initial formation of crystal centers. When the aggregates reach the desired size after 15 minutes, the secondary polymer is added into the solution to stabilize the aggregates by attaching on the uncoated surface or increasing the coating density.

The first polymer used is the random copolymer of acrylic acid (AA), vinylsulfonic acid sodium salt (technical, 25% in water, VSA), and 4-styrenesulfonic acid sodium salt hydrate (SSA). AA is used to provide the chelation groups with magnetite surface. VSA and SSA provide constant change over all pH conditions. SSA is used to provide hydrophobicity to enhance particle stability. Molar ratio among the monomers is 2:1:1 and this copolymer will be just referred based on this ratio. 0.1 g of potassium persulfate is used as the initiator and 0.4 g of sodium metabisulfite as the chain transfer agent. 2.5 mL of solution is used as the first polymer for particle synthesis. Then 1.0 g of 50% poly(acrylic acid) (MW=5,000) is used as the second polymer so that there are enough carboxyl groups for further modifications. In this coating copolymer, acrylic acid provided carboxyl groups to chelate with magnetite surface, while vinyl sulfonic acid (VSA) and styrenesulfonic acid (SSA) provided pH-independent negative charges over a broad range of pH, and SSA afforded hydrophobicity necessary to increase coating thickness and enhance particle stability. The prepared magnetic clusters were colloidally stabilized by electrostatic repulsion and withstand months in water without noticeable sedimentation even within 1 M sodium chloride solutions.

Colloidally stable magnetic nanoparticles with an average diameter of about 80 nm were prepared through co-precipitation of iron (II) and iron (III) chlorides in the presence of a random copolymer of acrylic, vinylsulfonic, and styrene sulfonic acids. After controlled aggregation of the nanoparticles to form aggregates with a diameter of about 80 nm, the exposed carboxyl groups were reacted with cyanoacetohydrazide to form a carbodiimide with a terminal nitrile group.

Example 5

Synthesis of Magnetic and Reactive Colloids Modified with Nucleophilic Oximate Groups In this Example, carboxyl groups on the particle surface were targeted for chemical modification. They were activated with N-(3-dimethylaminopropyl)-N'-ethylcarbodiimide (EDC) and then formed amide bonds with amine groups of the target molecule, which is carrying functional groups or precursors of functional groups. The amine group is most effective for this water-based reaction because it is a strong nucleophile.

Ferric chloride hexahydrate (97%), ferrous chloride tetrahydrate (99%), acrylic acid (99%), vinylsulfonic acid sodium salt (technical grade, 25% in water), 4-styrenesulfonic acid sodium salt hydrate, sodium metabisulfite, potassium persulfate (99%), poly(acrylic acid) (typical $M_w$ 5,000), N-(3-Dimethylaminopropyl)-N'-ethylcarbodiimide hydrochloride (EDC), cyanoacetohydrazide, 4-Morpholineethanesulfonic acid (MES), hydroxylamine hydrochloride, and p-nitrophenyl acetate (PNPA) were purchased from Sigma-Aldrich Chemical Company (Milwaukee, Wis.) and used as received. Methanol, ammonium hydroxide (30% in water), and sodium hydroxide were purchased from Mallinckrodt Baker Inc. (Phillipsburg, N.J.) and used as received. N'1, N'3-dihydroxy-propanediimidamide (tech) was purchased from Ryan Scientific (Mt. Pleasant, S.C.) and used as received. Water was generated by the Milli-Q water system.

In order to attach amidoxime groups, nitriles as precursor were firstly attached on the particles, as shown in Scheme 8.

Scheme 8. Attachment of a nitrile group through EDC chemistry.

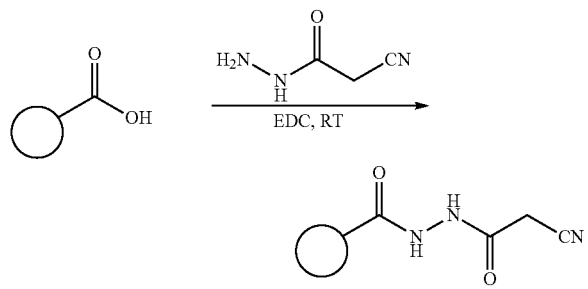

Figure 6:
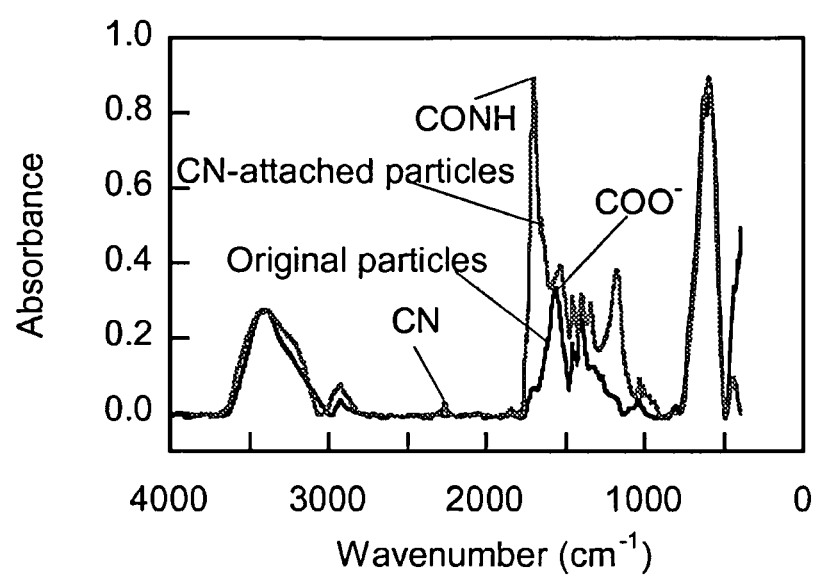
FIG. 6 depicts FTIR spectra of particles before (black) and after (red) nitrile modified particles.

The carboxyl groups on the particle surface were then functionalized by attaching nitrile groups. 0.49 g of MES was added to the above mixture to form particle dispersion in 50 mM MES buffer and the dispersion pH was adjusted to 5.3 by addition of 1 M hydrochloric acid. Activating agent EDC (0.6 g, 3.1 mmol) was then added to the particle dispersion. The particle/EDC dispersion was allowed to equilibrate for 5 min. Then 1 g of cyanoacetohydrazide was added and the reaction mixture was kept at room temperature overnight with stirring. Cyanoacetohydrazide was utilized because it provided both a hydrazide group for carbonyl hydrazide bond formation and a nitrile group that could be converted subsequently into a nucleophilic amidoxime group. The nitrile-modified particles were then washed by magnetic decantation with addition of 50 mL of acetone. After drying under vacuum overnight, particles were dispersed in 50 mL of methanol. Control experiments without addition of EDC were also performed to validate the nitrile attachment. The modified particles were tested for the presence of nitrile groups by FT-IR, as shown in FIG. 6. Major absorption bands were seen at 625, 1570, and 3440 $cm^{-1}$, corresponding to vibrational frequencies of magnetite, carboxyl groups, and surface hydroxyl groups from the surface FeOH and chemisorbed water on the magnetite, respectively. After the modification, two major absorption bands appeared at 1710 $cm^{-1}$ and 2250 $cm^{-1}$, corresponding to the NH—C=O and nitrile stretching, respectively. Analogous control procedures applied to the system without the activating agent (EDC) did not result in particles with any detectable presence of nitrile groups. This suggested that the above procedure successfully produce particles with nitrile groups chemically bonded to the particle surface.

Figure 7:
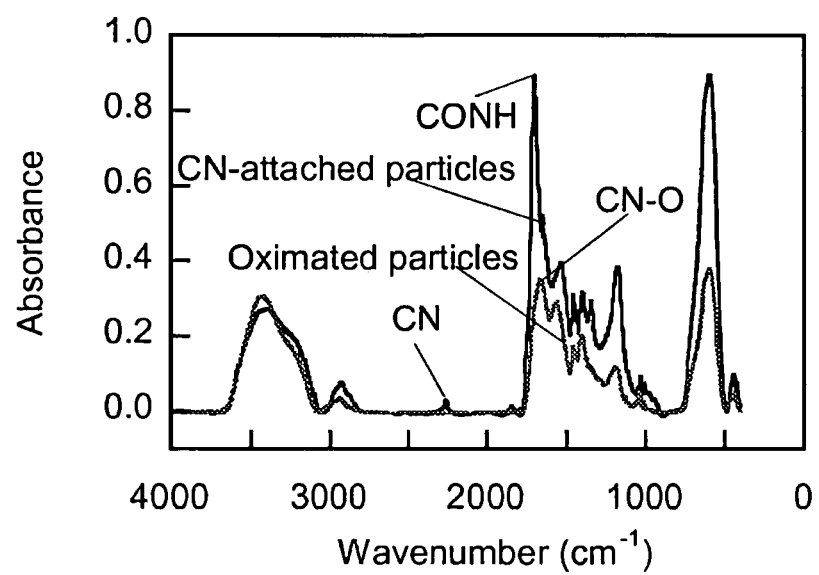
FIG. 7 depicts FTIR spectra of particles before (black) and after (red) oximation of the nitrile group.

The nitrile groups were then converted to amidoxime groups through the oximation reaction. Hydroxylamine hydrochloride (1.35 g, 1.94 mmol) and sodium hydroxide (0.78 g, 1.94 mmol) were added to the particle dispersion. The reaction mixture was refluxed at 65° C. overnight. Particles were then repeatedly washed by excess water and magnetic decantation and finally dried under vacuum until a constant weight was attained. These particles are referred as "modified particles" in the following discussion. FT-IR tests of the oximated particles are shown in FIG. 7. The appearance of an absorption peak at 1680 $cm^{-1}$, which corresponds to oxime groups, and the disappearance of nitrile groups suggest that the nitrile groups were successfully converted into amidoxime groups. It has been shown elsewhere that carboxyl groups can be transformed into hydroxamic acid groups by hydroxylamine. Control experiments were performed to check on the possibility by subjecting the original particles to the same conversion procedures as used for the modified particles. The control samples did not show any activity for PNPA hydrolysis, which suggests that carboxyl groups were not transformed into hydroxamic groups by this particular procedure.

The modified particles were characterized by various methods. The molecular weight of original 2:1:1 polymer was measured with gel permeation chromatography (GPC). The prepared 2:1:1 polymer was cleaned up with repeated wash with water and acetone. GPC studies were performed by injecting a 0.1% (mass) solution of the polymer dissolved in 10 mM of phosphate buffered saline (PBS) solution at pH 7.4 into a Ultrahydrogel Linear column (Waters Co., Milford, Mass.) with a Waters 2414 RI detector and 1×PBS solution as the eluent.

A Nexus-870 FT-IR spectrometer (Thermo Nicolet Corp., Madison, Wis.) was used in absorbance mode to determine the various chemical bonds present on the surface of the particles. All particle samples were ground, mixed with KBr, and then pressed to form pellets. The KBr background was subtracted from the sample spectrum.

Figure 25:
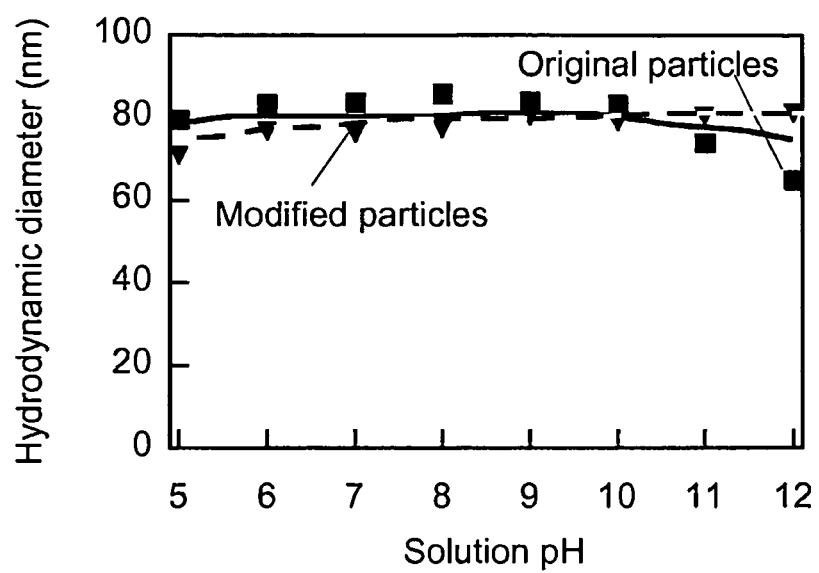
FIG. 25 depicts size comparison before and after modification reaction at various solution pHs. Original particles were from the two-step synthesis procedure, and modified particles were those after the nitrile-attachment and oximation reaction. Particle concentration was kept at 0.005 wt % for measurement. All samples were measured in 0.01 M buffer, citrate buffer for pH 4 to 6, phosphate buffer for pH 7 to 8, borate buffer for pH 9, carbonate buffer for pH 10 and 11, and phosphate buffer for pH 12.

Dynamic light scattering (DLS) was used to measure the hydrodynamic diameters of the particles before and after modification. DLS experiments were performed with the Brookhaven BI-200SM light scattering system at a measurement angle of 90°. Sample temperature was kept at 25° C. Particle dispersion was adjusted to 0.005% wt with 0.01 M buffer to keep the solution pH constant. The buffers used were citrate buffer for pH 4 to 6, phosphate buffer for pH 7 to 8, borate buffer for pH 9, carbonate buffer for pH 10 and 11, and phosphate buffer for pH 12. Particle diameter was extracted from the measured autocorrelation function by using the vendor-supplied software to fit an exponential model. Quoted particles sizes are based on intensity-averaged size distribution and the number average of four independent measurements. Hydrodynamic diameters of prepared particle were determined by dynamic light scattering (DLS). As shown in FIG. 25, particle size is very similar to that of the original particles over the pH range of 5 to 12. This indicated the absence of agglomeration and particle suitability for recovery by high gradient magnetic separation (HGMS) over the normal pH operational range. Particle size was very similar to that of the original particles, meaning that the magnetic aggregates are chemically stable enough to survive the modification process.

Figure 26:
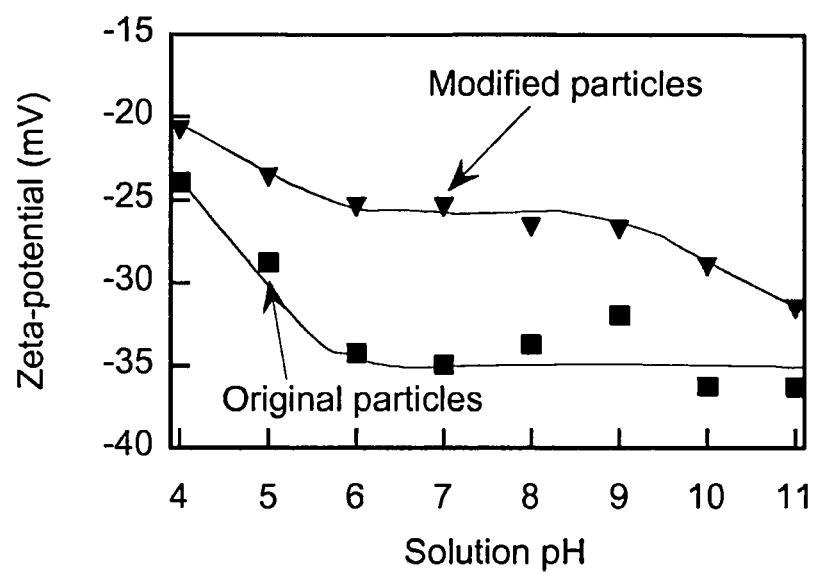
FIG. 26 depicts the zeta potential of particles before (square) and after (triangle) the modification procedure at various solution pHs. Particle concentration was kept at 0.005 wt % for measurement. All samples were measured in 0.01 M buffer and 0.1 M of NaCl, citrate buffer for pH 4 to 6, phosphate buffer for pH 7 to 8, borate buffer for pH 9, carbonate buffer for pH 10 and 11.

Zeta potential measurements were performed to analyze surface charges of the magnetic particles. Zeta potentials were measured on a Brookhaven ZetaPals Zeta Potential Analyzer. Particles were diluted to 0.005% wt $Fe_3O_4$ within 10 mM buffer solution and 0.1 M sodium chloride prior to measurement. Buffers used were the same ones used in DLS measurement. The zeta potential was converted from the electrophoretic mobility ($\mu_e$) of the particles measured over 25 cycles by fitting to the Smoluchowski equation, which requires that the particle size be much larger than the Debye length of the electrical double layer. The Debye lengths in 0.1 M of 1:1 and 2:1 electrolytes solution are 0.96 nm and 0.56 nm at 25° C. respectively. Since particles are larger than 70 nm, Smoluchowski equation is always applicable. The quoted zeta potentials are number averages of five measurements. Zeta potentials of particles at various pH values are shown in FIG. 26. The original particles were strongly negatively charged over the whole pH range studied because of the presence of sulfonic and carboxyl groups. Since they have a pKa value of 4.25, the carboxyl groups start to become protonated at around pH 5 and therefore the negative charge decreases with decreasing solution pH. After the modification, particles were still strongly negatively charged due to the presence of the sulfonic groups, which have pKa values less than 1. However, the electrokinetic potential of the modified particles was smaller than that of the original particles, which can be attributed to the fact that carboxyl groups reacted with amine groups and lost their negative charge. The amidoxime groups have a pKa value around 10.6 and this causes the gradual decrease of zeta potential in the high solution pH range. At relatively lower pH, the surface charges became similar in both cases, indicating that the sulfonic groups were playing a dominant role. Because of the strong surface charge, both particles were able to maintain excellent colloidal stability for months without observable sedimentation at neutral pH.

Transmission electron microscopy (TEM) analysis was performed on a JEOL 200CX microscope (200 kV) to analyze the cluster structures before and after the modification reaction. Samples were prepared by evaporating dilute particle solution on a carbon-coated film. TEM pictures of the particle clusters before and after the reaction are shown in FIG. 24. Very low particle concentrations were utilized in order to ensure that the results are depictions of clusters and not of artificial clustering of the particles during TEM preparation. As seen in FIG. 24, particles after nitrile attachment and oximation, reaction remained in the form of clusters. This indicated that the reactions did not change the particle morphology. However, this cluster didn't necessarily represent the typical cluster size.

Figure 27:
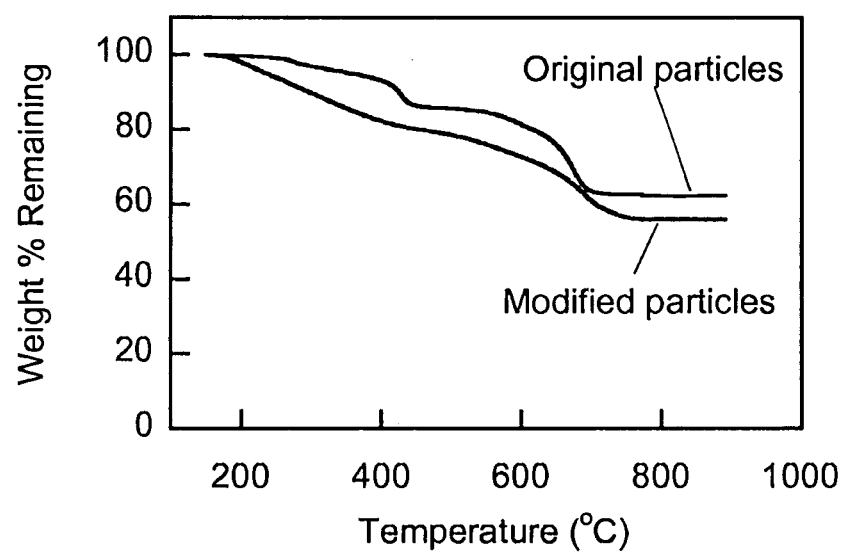
FIG. 27 depicts TGA analysis of magnetic particles before and after chemical modification. The initial faster weight loss and final weight percentage difference were from the attachment of nitrile group and the following oximation reaction.

Thermo gravimetric analyzer (TGA) was utilized to analyze the particle weight change with increasing temperature. The analysis was conducted on a TGA Q50 instrument (TA Instruments). Approximately 15 mg of dried magnetic particles was loaded into the sample pan and the sample pan was then inserted into the furnace purged with nitrogen to prevent oxidation. The heating profile in the TGA was as follows: heat to 150° C. at 5° C./min; hold at 150° C. for 30 min; heat to 900° C. at 5° C./min. The sample weight was then recorded as a function of temperature. The magnetic particles before and after the chemical modification were analyzed with thermo gravimetric analyzer (TGA) to determine the amount of chemically bound material on the particles after being cleaned up and dried. The TGA results are shown in FIG. 27, in which the residual mass percentage is plotted as a function of temperature. For the original particles, the attached polymer was decomposed in two separate phases. The first phase was probably from the side chains of the attached polymer. The second phase started at around 550° C. and the chemically bound groups on magnetite surface started to decompose. The modified particles started the second phase started around the same temperature as the first phase was finished. In the modified particles, the initial weight loss was much more than the original particles, indicating the attached functional groups were decomposed at this stage in addition to the previously mentioned polymer side chains. The residual magnetite weight percentage was used to compute the bound-polymer/magnetite mass ratios, which were found to be 0.60 and 0.78 before and after the chemical modification. The polymer/magnetite ratio was also measured through iron titration test to be around 0.70 and 0.85 respectively, consistent with the TGA measurements.

Elemental analysis for nitrogen was performed at Atlantic Microlab, Inc. to quantify the functional groups present after the particle modification. The amidoxime-presenting magnetic nanoparticles were colloidally stable over a broad pH range presumably because of the strong surface charge and the resulting electrostatic repulsion. Elemental analysis showed that the nitrogen content of the particles was 3.32 wt %. Based on the chemical transformation reaction, one nitrogen atom brought twice the weight of nitrogen onto the particles. This result is consistent with the TGA measurement. This nitrogen weight content was converted into an average molar concentration by assuming that all EDC-activated carboxyl groups reacted with cyanoacetohydrazide and that all nitrile groups were completely converted into amidoxime groups. Based on the fact that one functional group contains four nitrogen atoms, 1 mg/mL particle solution corresponded to 0.59 mM functional amidoxime groups assuming that the functional groups are homogenously distributed in the solution.

Example 6

Synthesis of Magnetic and Reactive Colloids Modified with Nucleophilic Imidazole Groups Imidazole groups are attached on the particle surface using the same chemistry as described above. Carboxyl groups are activated with EDC and then the amine groups react with the activated group to form amide bond. 1-(3-Aminopropyl)imidazole is used as the target molecule to provide both amine and imidazole groups. The reaction is shown in Scheme 9. Solution pH is kept at 5.3, EDC:COO⁻ ratio is 1:1, and 5 times of 1-(3-aminopropyl) imidazole is used.

Scheme 9. Attachment of imidazole group through EDC chemistry.

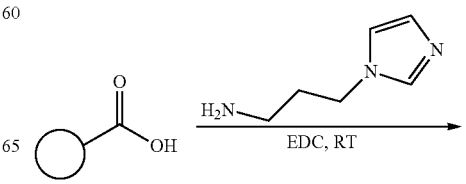

-continued

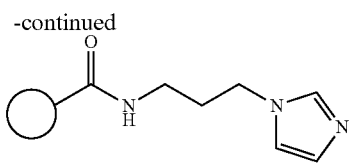

Example 7

Synthesis of Magnetic and Reactive Colloids Modified with Bactericidal Drug Chlorhexidine Magnetic particles were then used to carry other types of functionalities. Chlorhexidine was chosen for its antibacterial properties. Carboxyl groups on particle surface were activated by EDC with 1:1 molar ratio in 50 mM of 2-(N-morpholino)ethanesulfonic acid (MES) buffer while keeping the solution pH at 5.3. Five minutes after EDC was mixed into particle solution, 2 times of chlorhexidine digluconate solution (20% weight percentage) was added into the solution. Amine groups are plentiful in this molecule, so this reaction proceeded fairly quickly and easily. Reaction was kept overnight. The modified particles were then collected by electromagnet and washed with acetone. After being dried under vacuum overnight, these particles were tested with infrared spectroscopy. The result showed a strong absorbance between 1400 and 1600 $cm^{-1}$, indicating the presence of chlorhexidine. Elemental analysis confirmed that the concentration corresponding to 1 mg/mL particle solution is 1.02 mM and the total weight of chlorhexidine comprises around 51% of that of overall modified particles.

Example 8

Bactericidal Properties of Magnetic and Reactive Colloids Modified with Chlorhexidine; Antibacterial Action of Chlorhexidine-Modified Particles

*Enterococcus faecalis* is a Gram-positive, facultatively anaerobic, cocci that is a normal inhabitant of the intestinal tract and female genital tract. The microorganism is a leading cause of bacterial infection among hospital patients. This bacterium lives peacefully in the human gut, but it also thrives on wounds and burns.

Pure cultures of *Enterococcus faecalis* (ATCC12399, American Type Culture Collection, Rockville, Md.) grown on trypticase soy agar with defibrinated sheep blood at 37° C. were suspended in sterile 0.85% NaCl solution. The bacterial suspension concentration was adjusted spectrophotometrically to match the turbidity of a McFarland 0.5 scale (~1.3×$10^8$ colony-forming unit, or cfu/mL). Testing of $Fe_3O_4$ particles modified with poly(acrylic acid) (PAA) (termed M-PAA) and chlorhexidine gluconate (CHD) (termed M-PAA-CHD) was accomplished as follows. The particles were suspended in deionized water at predetermined concentrations using 1-min sonication and the resulting suspensions (1 mL, pH 5.1) were placed on the bottom of 3.2-mL wells of 24-well Corning® Costar® cell culture plates (Sigma-Aldrich Chemical Co.). Sterile saline and chlorhexidine gluconate were used as controls. Six wells were used for each time and concentration datapoints. Two mL of the bacterial suspension were placed into corresponding wells and each well was vigorously stirred for 2-3 s using a sterile pipette tip. The plates were shaken at 200 rev./min using a KS10 orbital shaker (BEA-Enprotech Corp., Hyde Park, Mass.) in an environmental chamber at 37° C. At a given time point, the magnetite particles were held at the bottom of the wells by a permanent horseshoe magnet, while 1 mL from each well of the bacterial suspension thus separated from the particles was transferred to tubes containing 2 mL of Brain Heart Infusion agar (Becton, Dickinson & Co.) with 0.5% Tween 80 and 0.07% lecithin. Gomes B P, Ferraz C C, Vianna M E, Berber V B, Teixeira F B, Souza-Filho F J. "In vitro antimicrobial activity of several concentrations of sodium hypochlorite and chlorhexidine gluconate in the elimination of *Enterococcus faecalis*," *Int Endod J.* 2001, 34(6),424-428. Timepoints used were 1, 5, 30 min, 1, 2, and 8 h. All tubes were incubated at 37° C. for 7 days. The tubes considered to have positive bacterial growth were those with medium turbidity matching the turbidity of a McFarland 4 scale (about 12×$10^8$ cfu/mL) during the incubation period. The positive cultures were identified via the use of an identification kit (BBL Crystal Kit, Becton Dickinson).

TABLE 1

Time required to induce negative cultures (100% inhibition growth) of *E. faecalis*.

| Species | Contact time |
| --- | --- |
| 0.2 wt % chlorhexidine gluconate solution | 1 min |
| 0.1 wt % M-PAA-CHD | 8 h |
| 0.2 wt % M-PAA-CHD | 2 h |
| 1.0 wt % M-PAA-CHD | 30 min |
| 2.0 wt % M-PAA-CHD | 5 min |
| 2.0 wt % M-PAA | >8 h* |

*100% inhibition was not observed within the given experimental time

The observed results are collected in Table 1, which confirms antibacterial action of the chlorhexidine-modified magnetite particles. Unmodified M-PAA particles did not exhibit antibacterial action within the timeframe of the experiment.

*Pseudomonas aeruginosa* is a Gram-negative, aerobic organism that is a common inhabitant of soil and water. *P. aeruginosa* is an opportunistic pathogen exploiting some break in the defenses of the host to initiate an infection. It causes urinary tract infections, respiratory system infections, dermatitis, soft tissue infections, bacteremia, bone and joint infections, gastrointestinal infections and a variety of systemic infections, particularly in patients with severe burns and in cancer and AIDS patients who are immunosuppressed. *P. aeruginosa* infection is a serious problem in patients hospitalized with cancer, cystic fibrosis, and burns. The case fatality rate in these patients is 50 percent.

Inhibition of the growth of *Pseudomonas aeruginosa* (ATCC strain 15152) by the modified particles was studied as follows. To prepare the inoculum, freshly grown microorganisms were prepared to a 0.5 McFarland standard (approximately 1.3×$10^8$ cfu/mL) and then diluted in Mueller-Hinton broth (MHB, Becton Dickinson) and by the particle suspension.

The particles were suspended in deionized water at 3 wt % concentrations using 1-min sonication and the resulting suspensions (1 mL, pH 5.1) were placed on the bottom of 3.2-mL wells of 24-well Corning® Costar® cell culture plates (Sigma-Aldrich Chemical Co.). Six wells were used for each particle species, and 0.2 wt % (final concentration) of chlorhexidine gluconate was used as a positive control, while deionized water without any nanoparticles was used as a negative control. Two mL of the bacterial suspension in MHB were placed into corresponding wells (final bacterial concentration, ~1.5 cfu/mL) and each well was vigorously stirred for 2-3 s using sterile pipette tips. The plates were shaken for 10 min at 200 rev./min using a KS10 orbital shaker (BEA-Enprotech Corp., Hyde Park, Mass.) in an environmental chamber at 37° C. Then the magnetite particles were held at the bottom of the wells by a permanent magnet, while 1 mL from each well of the bacterial suspension thus separated from the particles was gently pipetted out and sprayed onto a glass slide in a fume hood. The glass slides used were 18×18 mm$^2$ microscope glass slides derivatized with aminopropyltrimethoxysilane. The glass slide was dried by a flow of air for several minutes, placed in a Petri dish, and immediately covered by a layer of Trypticase soy agar with 5% sheep blood. The Petri dish was sealed and incubated at 37° C. for 16 h. The grown microbial colonies were then counted. The results were expressed in percent of bacterial count on a treated glass slide relative to that on the untreated glass slide and were collected in Table 2. Lin, J., Qui, S., Lewis, K., Klibanov, A. M., "Bactericidal properties of flat surfaces and nanoparticles derivatized with alkylated polyethyleneimines," *Biotechnol. Prog.* 2002, 18, 1082-1086.

TABLE 2

Bactericidal activity of magnetic particles against *Pseudomonas aeruginosa*.

| Sample | Bacterial colonies (cfu/cm$^2$) | Bactericidal activity (%)* |
| --- | --- | --- |
| Water on glass slide | 80 ± 7 | 0 |
| 0.2 wt % chlorhexidine | Not detected | 100 |
| M-PAA | 72 ± 18 | 10 |
| M-PAA-CHD | 15 ± 12 | 80 |

*The data is rounded to the nearest tens place.

Example 9

Catalytic Reactivity of Magnetic Colloids—Hydrolysis by Imidazole- and Amidoxime-Modified Magnetic Particles This Example shows decontamination capability of the modified colloids of the present invention toward organic esters.

Nucleophilic catalysts function by attacking the O—P bond in organophosphorus compounds. Paraoxon (see later Examples) and fenitrothion are used as the representative OPE compounds. However, these compounds are very toxic and very hard to work with to examine the kinetics. Therefore, a model compound, p-nitrophenol acetate, was used for the initial tests because of its chemical similarity with target compounds, low toxicity, easy analysis of hydrolyzed products, and similar hydrolysis mechanism (breaking up the ester bond). The hydrolysis reaction is shown in Scheme 10. The modified magnetic aggregates were tested to catalyze this reaction.

Scheme 10. Hydrolysis of p-nitrophenol acetate in water

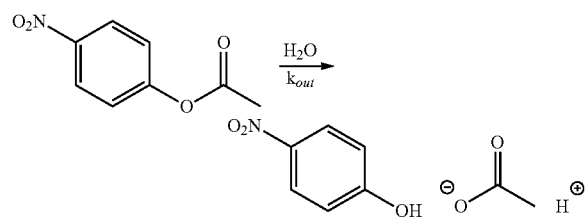

The hydrolysis product, p-nitrophenol, is in equilibrium with its ionic form, shown in Scheme 11a. Both forms can be detected with UV/Vis spectrophotometer. However, it is much easier to detect the ionic form because of much stronger absorption. Furthermore, the hydrolysis reaction produces protons, therefore changing system pH, and solution pH has a significant effect on the hydrolysis. Therefore, 50 mM Tris buffer was used during the measurement to prevent the effects of pH change and the pH was maintained at 8 to keep most hydrolyzed product in ionic form.

Scheme 11a. Acid-base equilibrium of p-nitrophenol in water

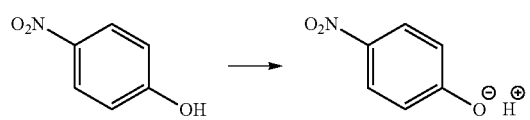

Hydrolysis of p-nitrophenyl acetate was followed by using a Hewlett-Packard 8453 UV/Vis spectrophotometer. The hydrolysis product, p-nitrophenol ion, has a strong absorbance at 404 nm. Samples were measured at 25° C. and solution pH was kept at 8 in 50 mM Tris buffer to prevent pH change during the hydrolysis. Reaction systems comprised of magnetic particles with concentrations of 1 to 4 mg/mL, 0.25 mM p-nitrophenyl acetate (PNPA) substrate, 0.2 M NaCl, 50 mM Tris buffer, and 20% vol ethanol in water solution. The presence of ethanol was to facilitate PNPA solubilization and these concentrations were overall concentrations in the final reaction mixture. Samples (0.5 mL) of the reaction mixture were withdrawn at selected intervals and the magnetic particles were removed by a high gradient magnetic separation (HGMS) device and a 50 mM Tris buffer (2 mL, pH=8) at the same pH was used to wash out of the column any possibly trapped hydrolysis product. The HGMS device was an L-1CN Frantz canister separator supplied by S. G. Frantz Co., Inc. (Trenton, N.J.). The system consisted of a cylindrical plastic column packed with type 430 fine-grade stainless steel wool (40-66 μm diameter) also supplied by S. G. Frantz Co., Inc. The packing fraction was 12% vol. A magnetic field was generated by an electromagnet with an intensity of 1.3 T between the two plates, as measured by a handheld magnetometer. The flow rate through the column was 1 mL/min. The liquid flow was controlled by a peristaltic pump. Recycling of the magnetic particles was performed by passing the previous reaction mixture through the column. The electromagnet was then turned off and the particles were fully washed out of the column with 20 mL of deionized water. Particles were collected through magnetic decantation with addition of 20 mL of acetone and dried at 50° C. in oven until constant weight. Particles were then dispersed into water to form a solution with the same particle concentration as that before the recycle. The particle solution was then subjected to the same reaction procedure as discussed above.

PNPA hydrolysis catalyzed by free N'1, N'3-dihydroxypropanediimidamide, which has two amidoxime groups, was also performed with 1 to 4 mM of amidoxime, 0.05 mM p-nitrophenyl acetate substrate, 0.2 M NaCl, and 50 mM Tris buffer in the final reaction mixture. The kinetic parameters from this homogenous system were compared with those from the particle system.

During the experiments, p-nitrophenol was dissolved in ethanol first. Appropriate amounts of particle solution and Tris buffer solution were then added into the solution. The reaction mixture was taken out at certain time intervals and HGMS was used to remove the magnetic aggregates. The particles were readily recovered from the aqueous milieu by HGMS and reused with no loss of reactivity. Tris buffer was used to wash out anything absorbed on the particle surfaces.

0.2 M NaCl solution was used to keep the ionic environment constant and to make particle removal by HGMS easier. The collected solution will be analyzed with UV/Vis spectrometry to detect the 4-nitrophenol ion concentration at the absorption wavelength of 405 nm. This procedure has been shown to be effective with standard substrate solutions. Since around 70% product is in ionic form at pH=8, total concentration of hydrolyzed product is calculated based on the measurements.

Hydrolysis of p-nitrophenyl acetate has been studied extensively under a wide range of conditions with addition of various homogenous catalysts. In these systems, the advantages of both homogenous and heterogeneous systems are combined. Because the particle size was very small and functional groups were located on the particle surface, mass transfer resistance was minimal and the particles functioned much like homogenous 30, catalysts. However, the functional groups were carried on magnetic particles, which made recycling and reuse of the catalyst by HGMS fairly straightforward.

In the presence of amidoxime groups, PNPA is hydrolyzed both spontaneously and by nucleophilic substitution as shown in Scheme 11b. The amidoxime groups on the particle surface attack the ester group, forming an intermediate complex and releasing p-nitrophenol. It has been shown that the substitution is a second order reaction. The complex is then deacetylated by hydroxide ions and the original amidoxime groups are regenerated for further catalytic reaction.

Three types of hydrolysis reactions are exhibited by the colloids of the present invention; namely, spontaneous hydrolysis, hydrolysis by OH groups, and hydrolysis by the catalytic particles. The first one is much slower than the second and third one, especially under high pH conditions. Since the $pK_a$ of p-nitrophenol is 7.2 and the reaction solution was kept at pH 8, the hydrolyzed product was in the form of both p-nitrophenol as well as p-nitrophenol ions, with the proportion depending on system pH. The total amount of hydrolyzed product was calculated from the measured concentration of p-nitrophenol ions through Equation 3 and the correction factor is 1.16 at the system pH 8.

$$[PNP]_{total} = [PNP^-]_{measure}(1 + 1/10^{pH-pK_a}) = 1.16 [PNP^-]_{measure} \quad (3)$$

Because the dissociation of p-nitrophenol releases protons and changes hydrolysis rate, 50 mM Tris buffer was used to keep pH constant at 8.

Figure 30:
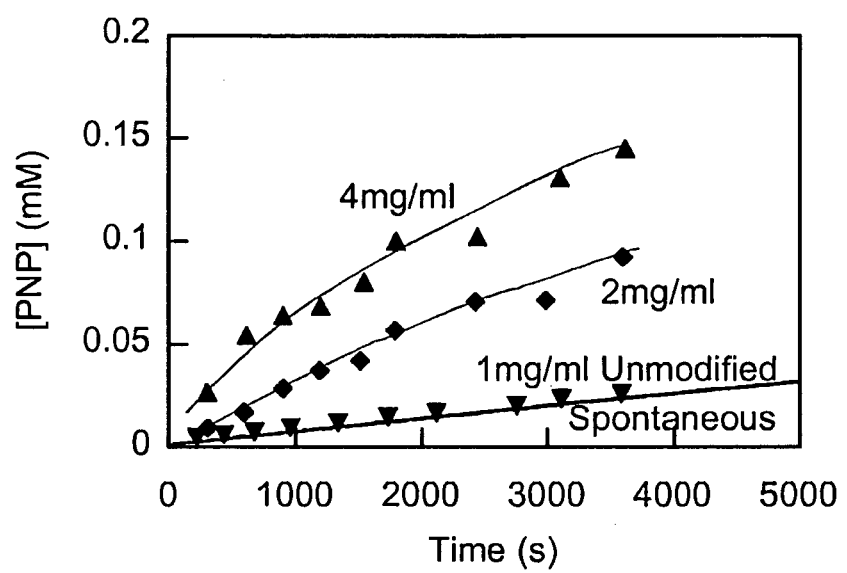
FIG. 30 depicts the concentration change of hydrolyzed product with addition of various particles. Spontaneous hydrolysis (black line), hydrolysis with 1 mg/mL of unmodified particles, and with 2 mg/mL and 4 mg/mL of functionalized particles. Solution pH was kept at 8 with 50 mM Tris buffer and 25° C. [PNPA]$_0$=0.25 mM.

FIG. 30 shows the concentration change of the hydrolyzed product with time progression when adding different amounts of amidoxime modified particles. With unmodified particles, overall hydrolysis was no different than spontaneous hydrolysis, indicating that the original particles had negligible effect. In the presence of modified particles, generation of hydrolyzed product was much faster, indicating that hydrolysis was clearly accelerated. As the particle concentration increased, the reaction rate also increased.

In the hydrolysis system, the hydrolysis product was generated by the spontaneous reaction, hydrolysis by hydroxyl ions and hydrolysis by the added nucleophiles. The reaction rate can be described by Equation 4a.

$$r = \frac{d[NP]}{dt} = (k_{spon} + k_{OH}[OH^-] + k_{cat}[NOH^-])[PNPA] = r_{spon} + r_{cat} \quad (4a)$$

During the initial stage of the hydrolysis reaction, the majority of nucleophiles remained in active form and concentration of nucleophiles was roughly constant. Since system pH was kept constant, the second term in the parenthesis is constant. During the initial stage of the reaction, the third term does not change significantly. Thus, this equation is simplified into displaying pseudo-first order kinetics. The integrated form of this kinetic equation is given in Equation 4b:

$$\ln(1 - [PNP]_t/[PNPA]_0) = k_{obs}t \quad (4b)$$

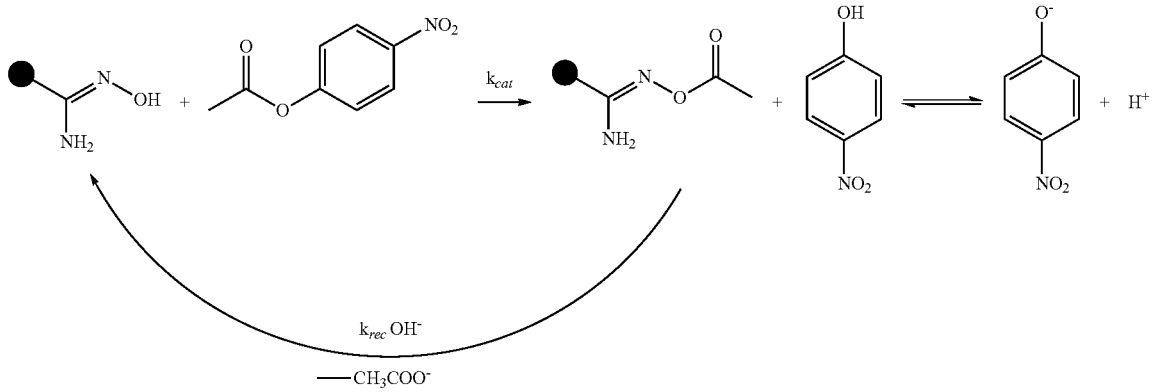

Scheme 11b. Catalytic hydrolysis of PNPA by amidoxime groups on the particle surface.

The $k_{obs}$ is the observed hydrolysis rate constant, including all three processes:

$$k_{obs} = k_{spon} + k_{OH}[OH^-] + k_{cat}[NOH^-] \quad (4c).$$

Figure 8:
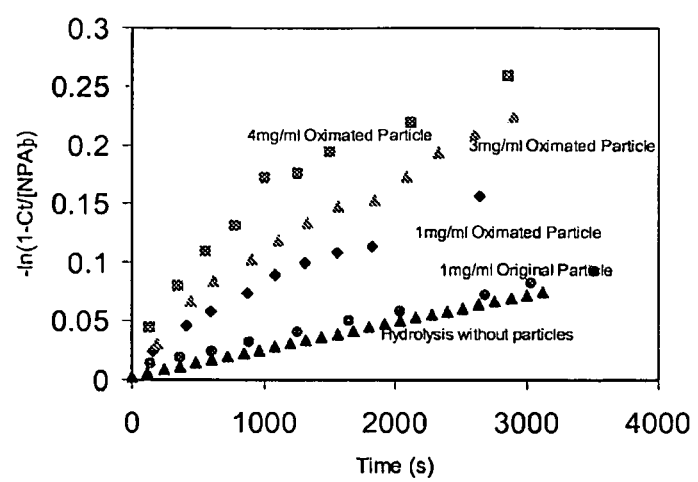
FIG. 8 depicts decomposition kinetic data with aldoxime-modified particles.
Figure 31:
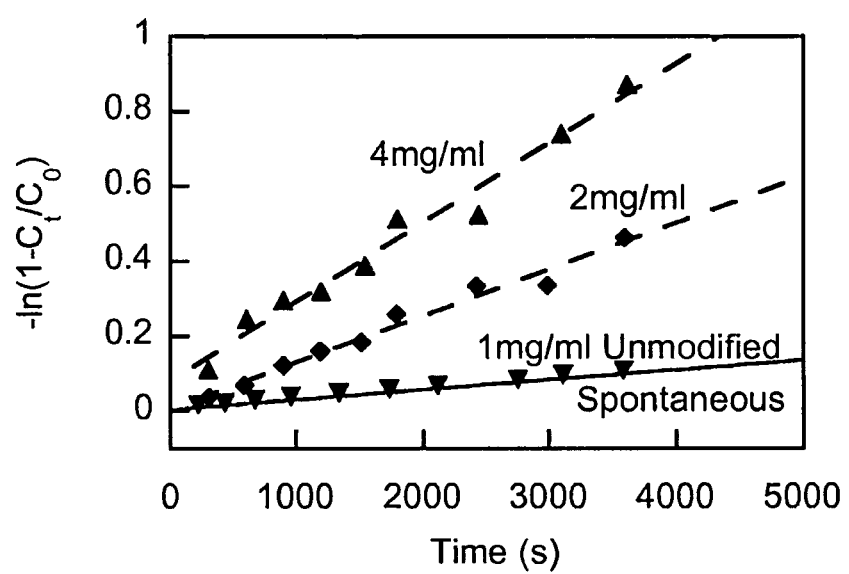
FIG. 31 depicts the pseudo-first order hydrolysis kinetics of PNPA with addition of various particle concentrations from spontaneous hydrolysis, hydrolysis with 1 mg/mL unmodified particles, and that with 2 mg/mL and 4 mg/mL functionalized particles. Solution pH was kept at 8 with 50 mM Tris buffer and 25° C. [PNPA]$_0$=0.25 mM.

Raw kinetic data were transformed according to the above equation and plotted against time so that the slope of the plot equaled $k_{obs}$. The obtained kinetic data are shown in FIG. 8 and FIG. 31. As is seen, kinetics with original particles are overlapping with the data from experiments without particles, meaning that the original particle has negligible effect on the decomposition. In the presence of functionalized particles, hydrolysis was clearly accelerated, especially during the initial stage.

Figure 32:
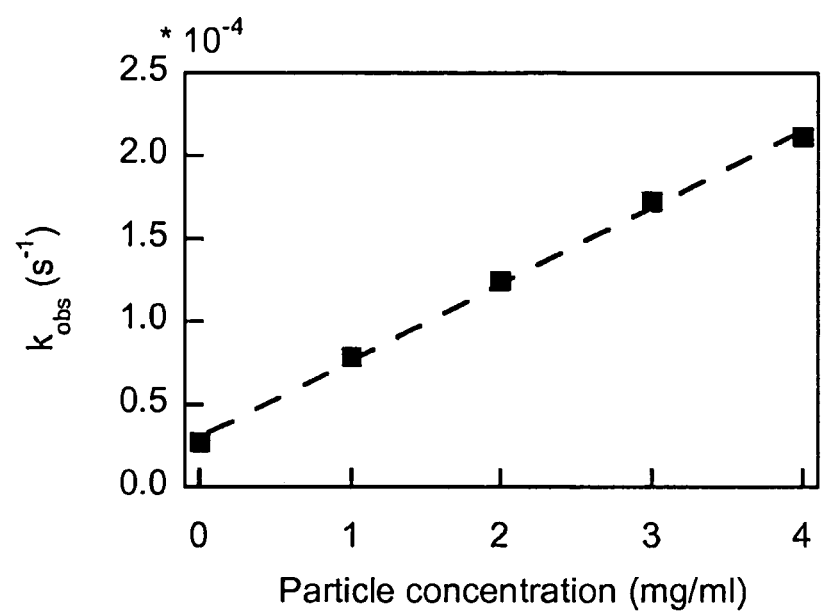
FIG. 32 depicts the dependence of observed hydrolysis kinetics constants on particle concentration. Slope of the linear fitting was second order with kinetic constant: $k_{cat}=4.6\times10^{-5}$(mg/mL)$^{-1}$s$^{-1}$ for particle dispersion.

The observed kinetics constants were measured for a series of particle concentrations and the initial hydrolysis rates obtained from the above procedure were plotted with regard to particle concentrations, as shown in FIG. 32. Spontaneous hydrolysis and hydrolysis by hydroxide ions were measured separately. The kinetic constant of $k_{cat}$ was then calculated by fitting the data points with a linear function from the plot of $k_{obs}$ versus amidoxime concentration. The second order kinetic constant is $4.6 \times 10^{-5} (mg/mL)^{-1} s^{-1}$ based on the particle weight and $7.9 \times 10-5 (mM)^{-1} s^{-1}$ based on the molar concentration of the amidoxime groups. As the particle concentration was increased, the reaction rate increased. Hydrolysis rate slows down with time increase because the consumption of catalyst is faster than catalyst turnover so that catalyst concentration is decreasing.

Figure 9:
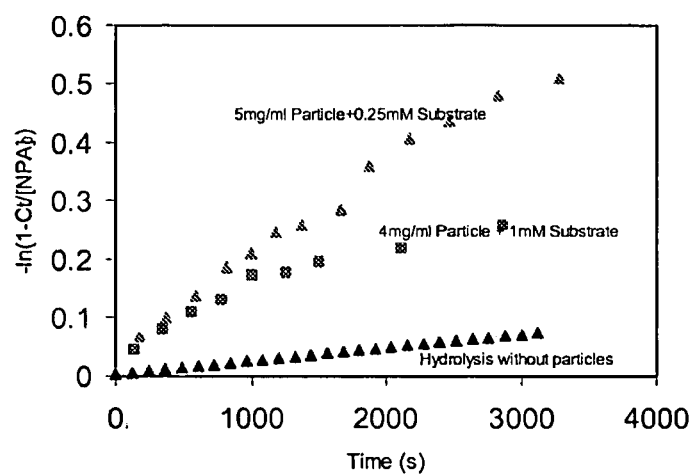
FIG. 9 depicts decomposition kinetic data with different particle/substrate ratios.

As shown in FIG. 9, leveling off of higher particle/substrate ratio appears much later than that of the lower one. This partially proves that catalyst consumption is faster than catalyst turnover thus causing slowdown of hydrolysis rate.

Figure 10:
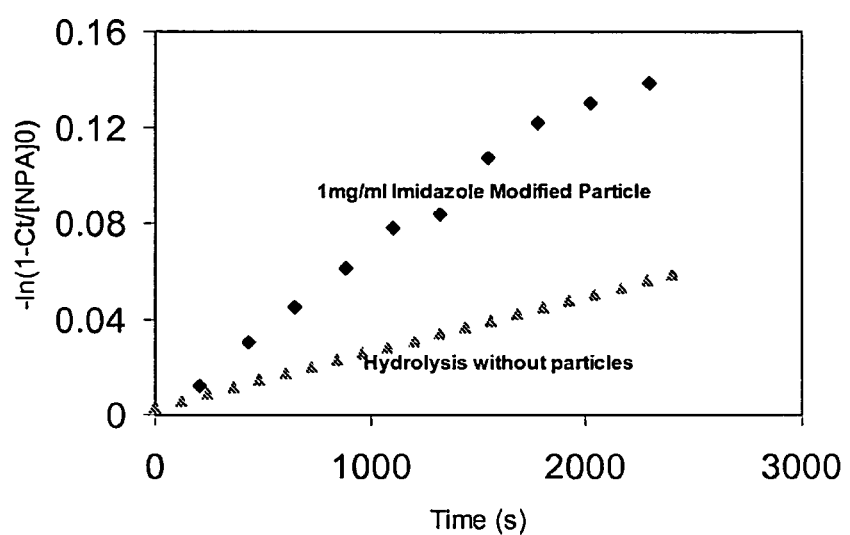
FIG. 10 depicts decomposition kinetic data for imidazole-modified particles.

Imidazole attached particles were tested with the hydrolysis reaction following the previous procedure. It is shown in FIG. 10 that this type of particle displayed similar behavior as the amidoxime-modified one. In the presence of 1 mg/mL particles, the initial hydrolysis rate doubled. The catalytic capability of the imidazole-modified particles is similar to that of the amidoxime-modified particles.

Example 10

Modification of Textiles with Catalytic and Basic Functionalities

Polyester Polartec® fabric (Polartec LLC, Lawrence, Mass.; Style, 7502; color, 6495) was pre-treated by impregnation in 1 M NaOH overnight at 80° C. This operation produced hydroxyl functionalities on the fabric surface (Scheme 12).

Scheme 12. Partial basic hydrolysis of polyester fabric resulting in —OH functionalities on the surface of the fabric.

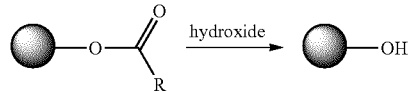

The pre-treated fabric was washed by deionized water extensively, by soaking in excess water for 5 days, and then the fabric was dried at 70° C. and 1 g of the fabric was impregnated with a suspension containing 5 g of Tyzor T E, 13 g of xylene, and 6 g of finely ground particles of polyacrylamidoxime. The impregnated fabric was kept at 80° C. in an oven overnight. The dried, treated fabric weighed 1.65 g.

The resulting fabric was grafted with a functional polymer, polyacrylamidoxime, as presented schematically in Scheme 13.

Scheme 13. Polyester fabric treated with polyacrylamidoxime.

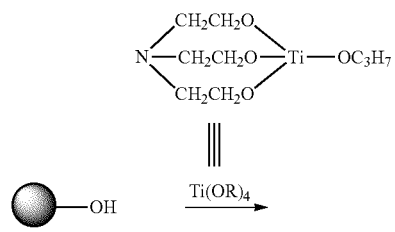

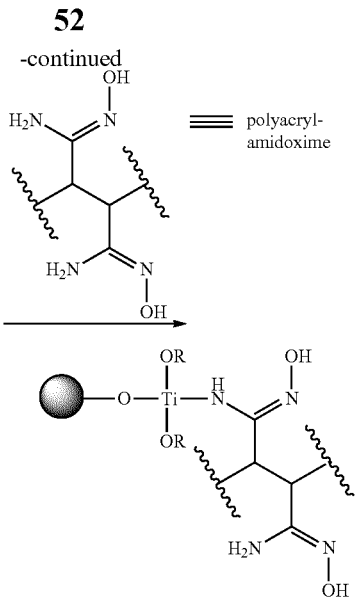

The fabric was tested for its ability to decompose diisopropyl fluorophosphate (DFP) using a published procedure. L. Bromberg, T. A. Hatton, Nerve agent destruction by recyclable catalytic magnetic nanoparticles, Ind. Eng. Chem. Res., 44(21) (2005) 7991-7998. Namely, a weighed amount of the fabric was placed in a vial containing 9 mL of 10 mM Tris buffer (pH 7.0, ethanol content, 50 v %). At t=0, a precisely measured amount (10 μL) of DFP was injected into the sample suspension and the output of an ion-selective electrode was measured as a function of time under stirring. The electrode measures concentration of a product of the DFP decomposition, fluoride ion. The presence of polyacrylamidoxime in the fabric resulted in the appearance and accumulation of the fluoride ions. The presence of the untreated fabric did not alter the response of the electrode, which remained at <10 mV/h positive drift level, which is inherent to that electrode under the experimental conditions of the present study. The kinetics of the DFP decomposition was quantified via $k_{obs}$, the observed pseudo-first-order rate constant. The $k_{obs}$ was found from the experimental data using the equation:

$$-\ln(1-C_f/[DFP]_o) = k_{obs} t$$

Thus $k_{obs}$ values found in 3 measurements were equal to $(2-4) \times 10^{-4}$ s$^{-1}$ and were 2 to 3 orders of magnitude larger than in the control measurements with unmodified Polartec® fabric. These measurements confirmed reactivity of the treated fabric.

Example 11

General Experimental Techniques for Examples 1-10

NMR experiments were performed at 25±0.5° C. using a Bruker DRX 401 NMR spectrometer. $^1H$, $^{13}C$, and $^{31}P$ NMR resonance frequencies were 400.13, 100.61, and 161.98 MHz, respectively. Proton decoupling was applied in all carbon and phosphorus NMR measurements. Kinetic experiments monitored by NMR were performed using WILMAD®coaxial inserts (reference capacity, 60 μL) along with thin-wall NMR tubes (sample capacity, 530 μl). A 0.105 M solution of ethylmethyl phosphonate (EMP) in $D_2O$ was applied as an internal reference throughout. A sample tube was filled with a 0.5-mL solution, of a given concentration, of chlorpyrifos and/or chlorpyrifos oxon in deuterated methanol and the solvent was gently evaporated by a stream of nitrogen.

Then a given amount (not exceeding 0.6 mL) of a 10 mg/mL PVA solution of IBX-PVA suspension in $D_2O$ (pD 7.4) was added to the sample tube, the external probe inserted, and the NMR tube assembly was sonicated for 3-4 s, wiped off, and the measurement commenced. The time interval from the contact between the OP substrate and the polymer suspension and the onset of the NMR measurement was approximately 1 min. Each $^{31}P$ NMR spectrum was acquired with 16 scans, which took 2.0 min, and the spectra were taken intermittently. To obtain the substrate concentration vs time plots, calibration plots using substrate/reference integration ratios vs known concentrations were measured with the same external probe that was utilized in all other measurements. Representative spectra of stable solutions of CP, CPO, and their mixture in $CD_3OD$ are shown in FIGS. 14, 15, and 16.

Kinetics measured with an ion-selective electrode utilized an electrode that measures concentration of a product of the DFP decomposition, fluoride ion.

FTIR were recorded in KBr using a Nexus 870 spectrometer (Thermo Nicolet Corp., Madison, Wis.) in absorbance mode by accumulation of 256 scans with a resolution of 4 $cm^{-1}$.

Dynamic light scattering (DLS) experiments were performed with a Brookhaven BI-200SM light scattering system at a measurement angle of 90°. Weight-average particle size distributions were obtained using the built-in software and the reported particle hydrodynamic diameters are the average of ten measurements. The samples were filtered with a 0.45 μm syringe filter prior to the DLS tests.

Example 12

PNPA Solubilization of Particle Surface

The hydrophobic absorption of p-nitrophenyl acetate on the surfaces of the modified magnetic particles was determined as follows. 2 mL of 5% wt of the amidoxime modified particle dispersion within 0.25 M of sodium chloride was mixed with 0.5 mL of 0.4 mM PNPA ethanol solution and kept at pH 7 to minimize hydrolysis. This mixture was similar to the one tested for kinetic measurement. The dispersion mixture was put into Centriprep® YM-50 centrifugal filter unit and centrifuged at 1500 g for 5 minutes. Then 1 mL of the obtained pure liquid was mixed with 1 mL of 1 M sodium hydroxide solution and the mixture was kept at room temperature for one hour to let PNPA fully hydrolyze. The p-nitrophenol ion concentration in final mixture was then measured with UV/Vis spectrophotometer at the absorbance of 404 nm. The above procedure was carried out again without addition of any particles to get the reference concentration under the same conditions. The difference of p-nitrophenol ion concentration was used to calculate the absorption of PNPA by the particles.

Example 13

Synthesis of Hydroxamic Acid-Modified Magnetic Nanoparticles

A new strategy to attach stronger nucleophilic groups to the nanoparticles is described in this example.

Ferric chloride hexahydrate (97%), ferrous chloride tetrahydrate (99%), acrylic acid (99%), vinylsulfonic acid sodium salt (technical grade, 25% in water), 4-styrenesulfonic acid sodium salt hydrate, 10-undecenoic acid, sodium metabisulfite, potassium persulfate (99%), acrylamide (≥99%), hydroxylamine hydrochloride, and p-nitrophenyl acetate (PNPA), polyacrylamide solution (50%, MW=10,000), were purchased from Sigma-Aldrich Chemical Company (Milwaukee, Wis.) and used as received. Ammonium hydroxide (30% in water), acetone, and sodium hydroxide were purchased from Mallinckrodt Baker Inc. (Phillipsburg, N.J.) and used as received.

The original particles were synthesized as in Example 4 until the addition of the 28% aqueous ammonium hydroxide solution and the formation of the magnetite particles. Subsequent to that addition, the following procedure was followed: Then 0.5 g of 10-undecenoic acid was added into the magnetite dispersion as the secondary coating material and the resulting dispersion was kept at 80° C. for another 15 min. The resulting magnetic particles were mixed with 50 mL of acetone, decanted by using an electro-magnet, re-dispersed into 50 mL of water and decanted after mixing with 50 mL of acetone three more times, and finally dried under vacuum until constant weight. The dry particles were re-dispersed in 50 mL of deionized water and sonicated for 1 min using a Branson Sonifier Model 450 at an output of 40% to form uniform dispersion. The particle weight concentration was 20 mg/mL. These particles were referred to as original particles.

The original particles were then copolymerized with acrylamide monomers to attach amide groups on the particles with the procedure described as follows. 0.6 g of acrylamide was added into 25 mL of previously prepared particle solution and the solution pH was adjusted to 3.2 by gradually adding 1 M of hydrochloric acid. The solution was purged with nitrogen under vigorous stirring. Then 0.1 g of potassium persulfate was added to the reaction mixture as the polymerization initiator and the reaction mixture was kept at 60° C. for 2 hours under continuous stirring. After the reaction was finished, 25 mL of acetone was added to the reaction mixture to precipitate the magnetite particles coated with newly formed copolymer. The particles were re-dispersed into 25 mL of water and decanted by an electro-magnet after mixing with 25 mL of acetone for three times to remove the unreacted monomers and other impurities. Finally, the purified particles were dispersed into 25 mL of water.

The attached amide groups were then transformed into hydroxamic acid groups through the following procedure. 1.05 g of hydroxylamine hydrochloride (15.1 mmol) and 4 mL of 5 M sodium hydroxide solution were added into 25 mL of acrylamide modified particle solution and the reaction mixture was kept at room temperature for 72 hrs under stirring. The reaction mixture was then cleaned up with the HGMS separation to remove any reacted raw materials as well as other impurities. HGMS was performed with an L-1CN Frantz canister separator supplied by S. G. Frantz Co., Inc. (Trenton, N.J.). The HGMS system consisted of a cylindrical column with the diameter of 1 cm packed with type 430 fine-grade stainless steel wool (40-66 μm diameter) also supplied by S. G. Frantz Co., Inc. The packing fraction was 12% vol. An electromagnet was used to generate a magnetic field with the intensity of 1.3 Tesla between the two plates. The particle solution passed the column at a flow rate of 4 mL/min with the magnet on to capture the particles. The liquid flow was controlled by a peristaltic pump. Then 20 mL of water passed the column to wash out any captured material except for the particles. The electromagnet was then turned off and the particles were fully washed out of the column with 20 mL of deionized water. Particles were collected through magnetic decantation with addition of 20 mL of acetone and dried under vacuum until constant weight.

Poly-hydroxamic acid (PHA) was also prepared with the same procedure as the particle transformation. Poly-acrylamide with the molecular weight of 10,000 was utilized for the preparation. After the transformation procedure, the polymer mixture solution was exhaustively dialyzed (membrane MW cutoff (MWCO), 3500) against DI water. The purified sample solution was then lyophilized and the dry polymer sample was stored dry at 2-8° C. until further use.

The particles were characterized by FTIR, DLS, TGA, and Elemental Analysis as outlined in Example 5. Similarly, the Zeta potential of the particles was analyzed as in Example 5. XPS measurements were taken according to the procedure outlined in Example 1. The molecular weight of original 2:1:1 polymer was measured with gel permeation chromatography (GPC). 5 mL of prepared polymer solution was mixed with 5 mL of acetone to precipitate the polymer while keeping the un-reacted monomers as well as other small molecules in solution. The polymer precipitate was dissolved in 5 mL of water and 5 mL of acetone was added to precipitate the polymer again. This was repeated for three times to fully clean up the polymer and finally it is dried in vacuum oven until constant weight. GPC studies were performed by injecting a 0.1% (mass) solution of the polymer dissolved in 10 mM of phosphate buffered saline (PBS) solution at pH 7.4 into a Ultrahydrogel Linear column (Waters Co., Milford, Mass.) with a Waters 2414 RI detector and 1×PBS solution as the eluent.

The molecular weight of surface coating polymer from the modification was analyzed as follows. After the particle preparation and cleaning-up by HGMS, 0.5 mL of hydrochloric acid (37%) was added to 2.5 mL of the magnetic fluid to dissolve the iron oxide core. The solution pH was then adjusted to 7.4 with 1 M of sodium hydroxide solution. The formed solid material was filtered out by a syringe filter with the pore size of 0.2 μm. The obtained solution was measured with GPC following the same procedure as above.

As discussed in the discussions regarding other functionalized magnetic particles, particle size and colloidal stability are the two most important factors for the applications of magnetic particles. Effective capture by HGMS requires preparation of the magnetic clusters of multiple individual magnetite particles with the hydrodynamic diameter larger than 50 nm other than individual magnetic particles with the size less than 10 nm. The prepared clusters need to be stabilized by steric and/or electrostatic interactions under the solution conditions of interest for effective re-dispersion after HGMS capture and stable operations.

In summary, original magnetic clusters were synthesized through a two-step procedure. In the first step, the magnetite cores were formed and then aggregated to form the magnetic clusters because of the instability generated by insufficient first coating material. In the first coating terpolymer, carboxyl groups chelated with magnetite surface, vinyl sulfonic acid and styrenesulfonic acid provided pH-independent negative charges over a broad range of pH, and SSA increased coating thickness and enhanced particle stability. The second coating material was 10-undecenoic acid, which provided the carboxyl groups to complex the particle surface and the carbon-carbon double bond to polymerize with other monomers.

Attachment of the precursor amide groups was accomplished through free radical copolymerization between the double bond of 10-undecenoic acid and that of acrylamide molecules. The reaction is depicted in Scheme 14.

Scheme 14. Attachment of amide groups through copolymerization

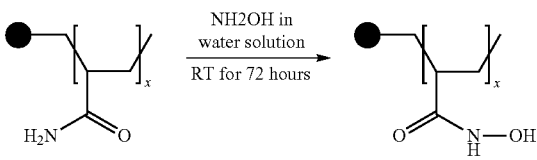

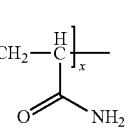

Acrylamide was employed because it provided the carbon-carbon double group for the copolymerization and amide groups that would be converted into targeted hydroxamic acid groups. The solution pH was controlled at 3.2 so that the reactivity of acrylamide would be lowered from the protonation of amide groups and then would be more comparable with the reactivity of 10-undecenoic acid. As a result, the acrylamide monomers formed copolymer with the 10-undecenoic acid on the particle surface instead of forming polyacrylamide homopolymer in the solution. Furthermore, the particles were still in the form of uniform dispersion at this solution pH so that the crosslink among magnetic clusters would be reduced.

During the conversion reaction step, the amide groups reacted with hydroxylamine to form the intermediates through nucleophilic substitution on the nitrogen atom of the amide groups and then yielded the hydroxamic acid groups through the release of ammonia. As a result, the reaction mixture released gas bubble continuously and the solution pH was decreased from 12 at the start of the reaction to 9.8 at the end. The reaction underwent through Scheme 15.

Figure 19:
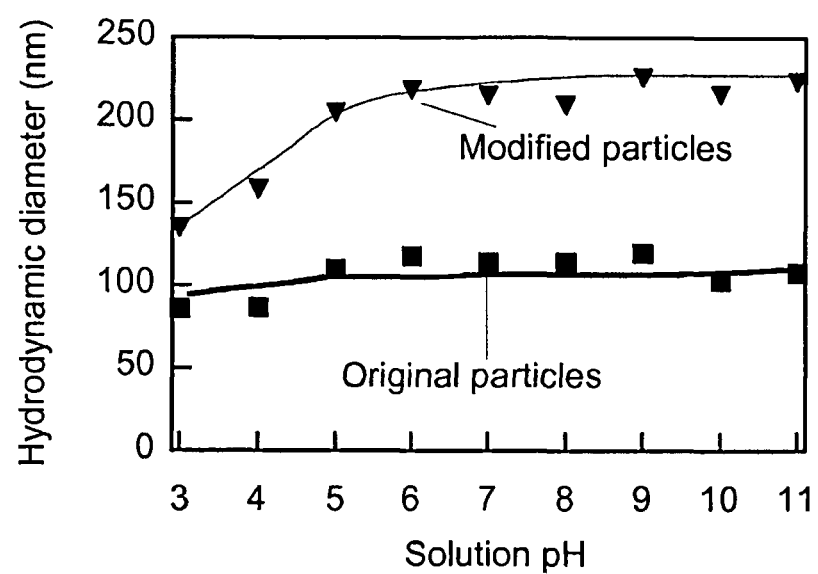
FIG. 19 depicts hydrodynamic diameters of particles before and after the modification reaction at various solution pH. Original particles were particles from the two-step preparation procedure and modified particles were those after the hydroxamic acid modification procedure. Particle concentration was kept at 0.005 wt % for measurement. All samples were measured in 0.01 M buffer, citrate buffer for pH 3 to 6, phosphate buffer for pH 7 to 8, borate buffer for pH 9, carbonate buffer for pH 10 and 11.
Figure 20:
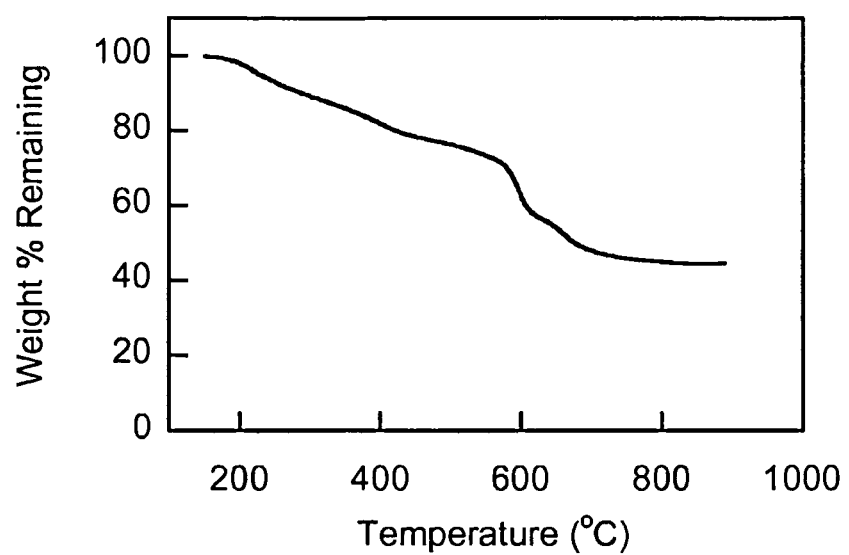
FIG. 20 depicts TGA analysis of hydroxamic acid modified magnetic particles after chemical modification.

Scheme 15. Transformation of amide groups into hydroxamic acid groups through the reaction with hydroxylamine at room temperature Hydrodynamic diameters of the particle before and after the modification procedure were measured with dynamic light scattering. As shown in FIG. 19, the average particle size was increased significantly from around 60 nm to around 180 nm by the modification procedure. The copolymerization procedure resulted in crosslinking between the original magnetic clusters because of the multiple copolymerization centers attached on the particle surface. The particles were functioning similarly to crosslink agents. This significant increase of particle size also suggested that the particles would be captured by HGMS even more efficiently than the original magnetic clusters due to the much larger size.

Thermo gravimetric analyzer (TGA) was used to determine the amount of chemically bound material on the particles. The TGA results are shown below in which the residual mass percentage is plotted as a function of temperature. In the first phase of the decomposition, the side chains of the attached polymer were gradually decomposed. In the second phase, the groups chemically bound with magnetite surface were decomposed. The residual magnetite weight percentage was used to compute the bound-polymer/magnetite mass ratio, which was 1.2 after the chemical modification. This is consistent with the result obtained through iron titration test.

Elemental analysis showed that the nitrogen content of the particles was 3.8% wt. In the particles only the copolymerized acrylamide and therefore the resulted hydroxamic acid were carrying nitrogen element. Therefore, the nitrogen content was converted into the molar concentration of nitrogen element and 1 mg/mL particle solution corresponded to 2.7 mM of amide groups and hydroxamic acid groups combined, indicating that the copolymerization procedure was highly efficient to attach a large amount of amide groups on the particle surface. Attempt to differentiate between amide groups and hydroxamic acid groups through XPS failed probably because the possible interaction with particle surface iron element rendered the two groups indistinguishable by XPS. However, pure polyhydroxamic acid was tested by XPS and provided clear distinction between these two groups. It was shown that molar ratio between amide group and hydroxamic acid group was 1:1.

The above 3.8% wt nitrogen element corresponded with 24% wt of polyacrylamide and polyhydroxamic acid, assuming 50% transformation efficiency. Based on the TGA analysis, the total coating on the modified particles was 55% of the total dry weight of the particles. Therefore, there was 30% weight coming from the initially coated polymer and 10-undecenoic acid during the initial particle preparation. This indicated that the added coating from the copolymerization and transformation was almost identical to the total coating during the initial particle preparation first coating.

Example 14

Hydrolysis of p-Nitrophenol Acetate by Hydroxamic Acid-Modified Particles

As discussed above, a significant number of hydroxamic acid groups can be functionalized to the surface of magnetic particles, therefore combining the advantages of both homogenous and heterogeneous systems. With the small size of the prepared particles and the functional groups being located on the particle surfaces, there is no significant mass transfer resistance. Since the hydroxamic acid groups were attached on superparamagnetic particles, the particles could be easily captured by HGMS and re-dispersed into water and the functional groups could be reused again for the targeted applications after regeneration. In this particular application, nucleophilic properties of the functional particles were studied with regard to the hydrolysis of model carboxyl esters, p-nitrophenyl acetate.

PNPA hydrolysis catalyzed by hydroxamic acid groups was shown to proceed mainly via the formation and the subsequent decomposition of the acetyl hydroxamate intermediate in addition to the spontaneous hydrolysis. The reaction mechanism is shown in Scheme 16. The acetylation reaction of hydroxamic acid was shown to be first order with respect to the PNPA substrate and the hydroxamic acid groups.

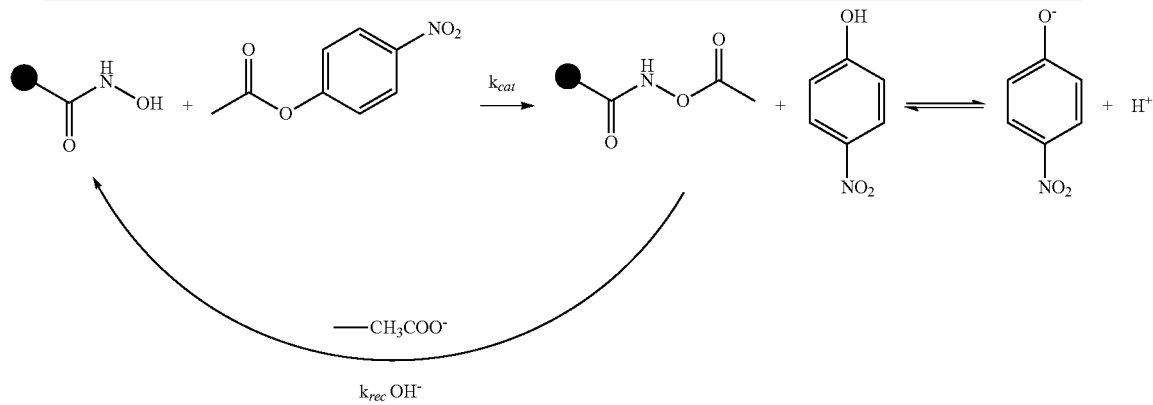

Scheme 16. Acetylation reaction of hydroxamic acid groups by PNPA and deacetylation reaction by hydroxide ions on the particle surface The above reaction is releasing protons and therefore affects the solution pH. Since solution pH also affects the reaction rate, the solution was kept at constant pH 8 with 50 mM Tris buffer. The released p-nitrophenol was in equilibrium with the p-nitrophenol ions and the overall concentration of the hydrolyzed product was calculated with the same procedure as shown in Example 9.

Figure 21:
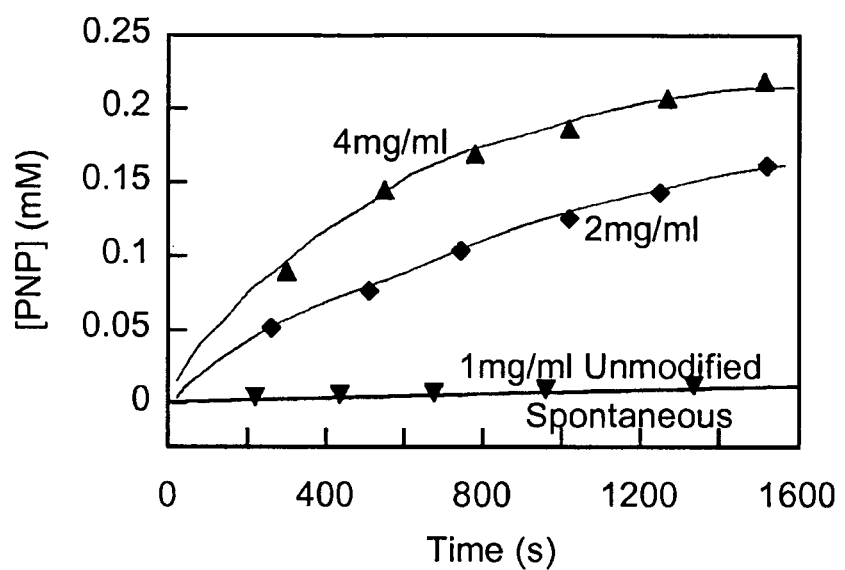
FIG. 21 depicts the concentration change of hydrolyzed product with addition of various particles. Spontaneous hydrolysis (black line), hydrolysis with 1 mg/mL unmodified particles, with 1 mg/mL, 2 mg/mL, and 4 mg/mL functionalized particles. Solution pH was kept at 8 with 50 mM Tris buffer and 25° C. [PNPA]$_0$=0.25 mM.

The concentration change of hydrolyzed product with time is shown in FIG. 21. The line was from the spontaneous hydrolysis under the same solution conditions. As shown in the figure, the hydrolysis with the addition of the original particles produced almost the same concentration change with time as the spontaneous hydrolysis. This suggests that the original particles not play any significant role for the PNPA hydrolysis. However, the product concentration increased much more quickly with the addition of hydroxamic acid modified particles than that from spontaneous hydrolysis, indicating the acetylation reaction of hydroxamic acid groups was much faster than the spontaneous hydrolysis.

PNPA hydrolysis by hydroxamic acid groups is first order with respect to the PNPA substrate and the hydroxamic acid groups. The PNPA was also undergoing the spontaneous hydrolysis by hydroxyl ions in the reaction mixture. The reaction rate of yielding the p-nitrophenol product is described in Equation 5.

$$r = \frac{d[NP]}{dt} = (k_{spon} + k_{OH}[OH^-] + k_{cat}[NOH^-])[PNPA] = r_{spon} + r_{cat} \quad (5)$$

Since solution pH was kept constant at 8 with Tris buffer, the first two terms in the parenthesis are constant. The majority of catalyst remained as active form and catalyst concentration was almost constant during the initial reaction stage. Thus this equation is essentially turned into a first order type of kinetics. The equation is then integrated into Equation 6

$$-\ln(1-[PNP]/[PNPA]_0) = k_{obs} t \quad (6)$$

in which $$k_{obs} = k_{spon} + k_{OH}[OH^-] + k_{cat}[NOH^-] \quad (7)$$

Figure 22:
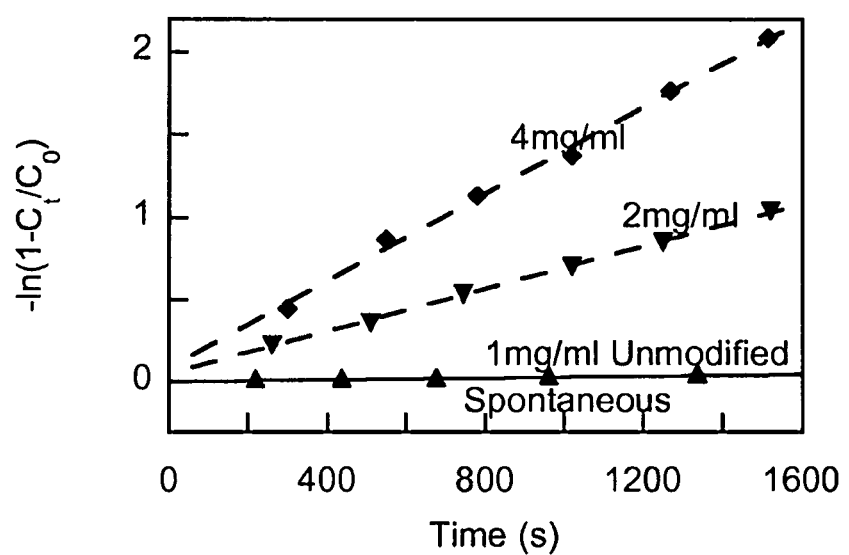
FIG. 22 depicts the pseudo-first order hydrolysis kinetics of PNPA with addition of various particles from spontaneous hydrolysis, hydrolysis with 1 mg/mL unmodified particles, with 1 mg/mL, 2 mg/mL, and 4 mg/mL hydroxamic acid modified particles. Solution pH was kept at 8 with 50 mM Tris buffer and 25° C. [PNPA]$_0$=0.25 mM.

The data were then transformed through the pseudo-first order kinetics and the results were plotted in FIG. 22, slope of the plot equals to $k_{obs}$.

Figure 23:
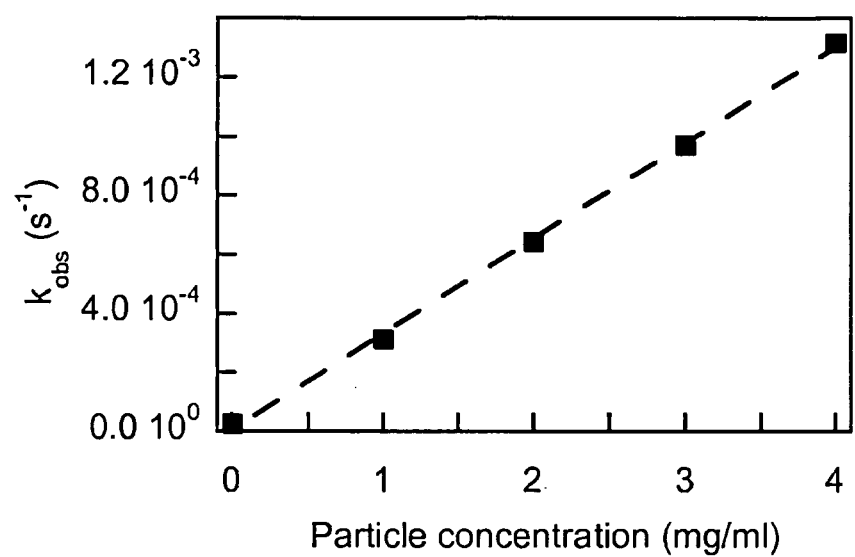
FIG. 23 depicts the dependence of observed hydrolysis kinetics constants on the concentration of the added particles. The second order kinetic constant based on particle weight concentration was $k_{cat}$=3.2×10$^{-4}$ (mg/mL)$^{-1}$s$^{-1}$.

The observed kinetics constants were measured with adding a series of concentrations of particle solutions and spontaneous hydrolysis was measured separately. These kinetic constants were plotted with regard to particle concentrations, as shown in FIG. 23. Data points were fitted with a linear function, slope of which was $k_{cat}$.

As shown in FIG. 23, kinetic constant from the hydrolysis reaction with addition of 4 mg/mL is 40 times to that from the spontaneous hydrolysis, indicating the strong nucleophilic properties of the hydroxamic acid groups and the significant amount of hydroxamic acid groups present on the particle surfaces. The linear relationship between the pseudo-first order kinetic constants suggests that particles were functioning as individual catalytic centers and there was no significant inter-particle interaction to affect the catalytic capability of the hydroxamic acid in the particle concentration range that we studied.

The PNPA hydrolysis catalyzed by polyhydroxamic acid was also studied under the same solution conditions. The kinetic constant under the pseudo-first order conditions with addition of 1 mM PHA (based on monomer basis and 50% is hydroxamic acid groups) was obtained to be $6.0 \times 10^{-4}$ $s^{-1}$ through the above mathematical procedure, whereas the same kinetic constant with addition of 1 mM acetohydroxamic acid was shown to be $2.0 \times 10^{-3}$ $s^{-1}$. Both monomeric and polymeric hydroxamic acid groups were able to react with PNPA much faster than spontaneous hydrolysis, reflecting the strong reactivity of hydroxamic acid groups. The hydroxamic acid groups in the polymeric form were less reactive than the corresponding monomeric compounds for the acetylation reaction by PNPA due to the steric hindrance by the polymer chains, consistent with the literature findings. By comparing the catalytic capability of modified particles and the of polyhydroxamic acid, 2 mg/mL of particles gave the same pseudo-first order kinetic constant as 1 mM of polyhydroxamic acid. However, 2 mg/mL of particle solution corresponded with 5.4 mM of nitrogen element. The large difference could be attributed to the following possible factors. First of all, presence of the negative surface charge decreased the ability of the hydroxylamine to approach the amide groups and therefore reduced the reaction efficiency during the transformation reaction. Secondly, amide groups buried inside the clusters were not available for the transformation reaction and therefore the reaction was not as effective as in the homogenous polymer system. Thirdly, hydroxamic acid groups on the particle surface were most easily approachable by the PNPA substrate and those inside the clusters were not very accessible. This would result in much lower activity of those functional groups inside the polymer coating layer. If we assume the amide groups on the particle with the diameter of 180 nm are fully packed, then the overall concentration of amide groups on the particle surface will be around 0.5 mM corresponding with 1 mg/mL particle dispersion. Therefore, 2 mg/mL particle solution has 1 mM amide groups and the following transformation will generate similar amount of hydroxamic acid groups for the particles as that of the homogeneous polymer solution. This explains why 2 mg/mL particle solution has similar pseudo-first kinetic constant as 1 mM polyhydroxamic acid.

Example 15

Recyclability of Amidoxime-Modified Magnetic Particles

Figure 29:
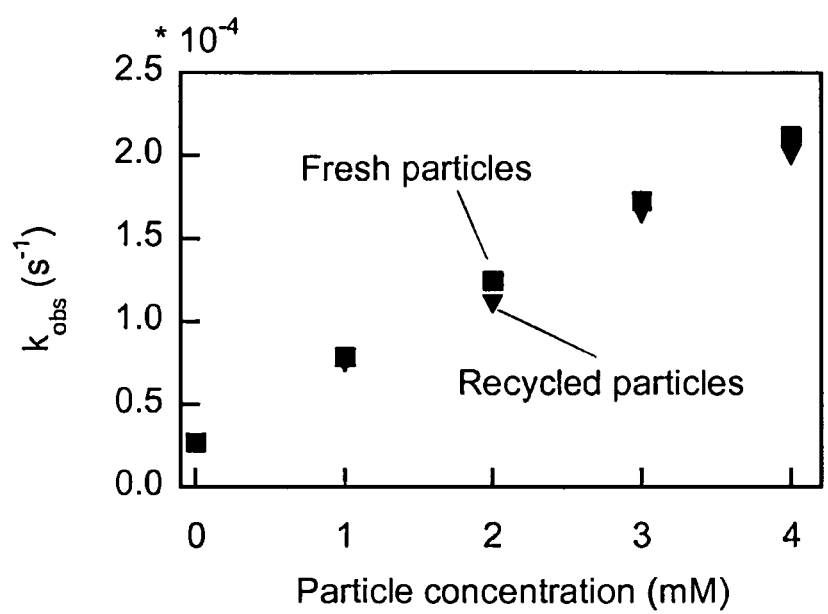
FIG. 29 depicts observed hydrolysis kinetic constants of fresh particles (square) and recycled particles (triangle) at various particle concentrations. Solutions were kept at pH 8 with 50 mM Tris buffer and 25° C. [PNPA]$_0$=0.25 mM.

Because of superparamagnetic property of the magnetic clusters, particles were fully recovered from the column after the first batch of reaction with the substrate. Kinetic constants of PNPA hydrolysis by the recycled particles were obtained with the same experimental procedure as discussed above (Example 9). As shown in FIG. 29, the recycled particles had very similar reactivity as the original ones.

Example 16

Comparison of Hydrolysis with Amidoxime-Modified Particles: Homogeneous Catalysis Versus Two-Phase Model In order to understand the role played by the particles in addition to providing functional groups, PNPA hydrolysis by functionalized particles was compared with that by an amidoxime compound, malonohydroxamamide, the structure of which is shown in Scheme 17.

Scheme 17. Structure of malonohydroxamamide

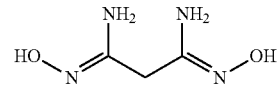

Figure 28:
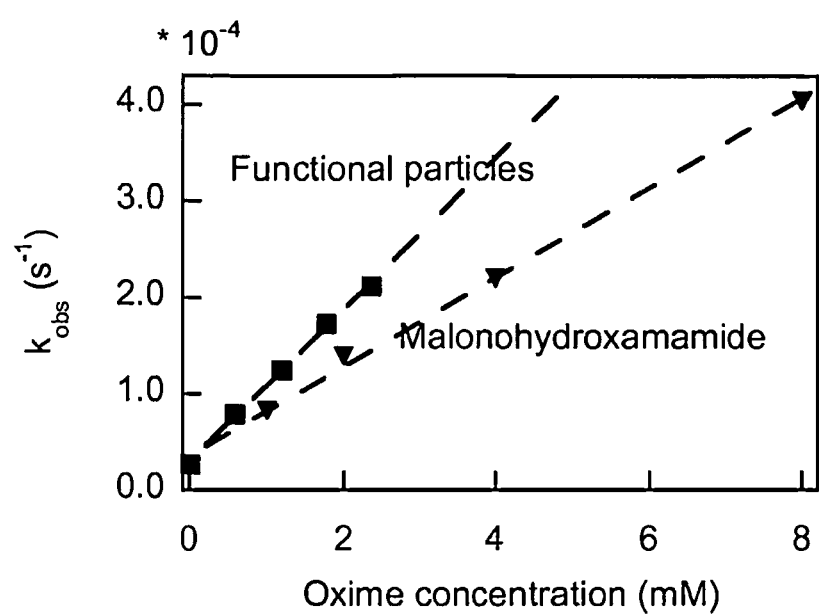
FIG. 28 depicts a comparison of observed hydrolytic kinetic constants catalyzed by malonohydroxamamide (square) and functionalized particles (triangle). Second-order kinetic constants were $k_{cat}$=4.6*10$^{-2}$ M$^{-1}$s$^{-1}$ for malonohydroxamamide and $k_{cat}$=7.9*10$^{-2}$ M$^{-1}$s$^{-1}$ for particle solution. Solution pH was kept at 8 with 50 mM Tris buffer and 25° C. [PNPA]$_0$=0.25 mM for particle system and [PNPA]$_0$=0.05 mM for malonohydroxamamide system.

Hydrolysis kinetics were measured under same conditions as those for the particle system (see Example 9), including 50 mM Tris buffer to keep system pH at 8, 0.2 M of sodium chloride to maintain constant ionic strength, and various amount of amidoxime. Because the amount of amidoxime added to the system was in the mili-molar range and much larger than the substrate concentration 0.05 mM, hydrolytic kinetics also showed pseudo-first order nature. The kinetic constants, $k_{obs}$, for homogenous amidoxime were obtained the same way as those from particle system. The comparison between particle and homogeneous systems is shown in FIG. 28. Second-order kinetic constants were $4.6 \times 10^{-2}$ $M^{-1}s^{-1}$ for malonohydroxamamide and $7.9 \times 10^{-2}$ $M^{-1}s^{-1}$ for particle solution. The kinetic constants for the particle system were the same as those in FIG. 32, with the particle weight concentration converted into amidoxime concentration according to the elemental analysis results.

Two-phase model, also called the pseudo-phase model, was invoked to explain why the particle system exhibits a larger second-order kinetic constant than does the homogenous amidoxime system, as represented in Scheme 18. The two phase model has been used extensively to describe the catalytic behavior of micellar systems.

Scheme 18. Pseudo two-phase mechanism
for the PNPA hydrolysis with the
presence of amidoxime modified magnetic particles.

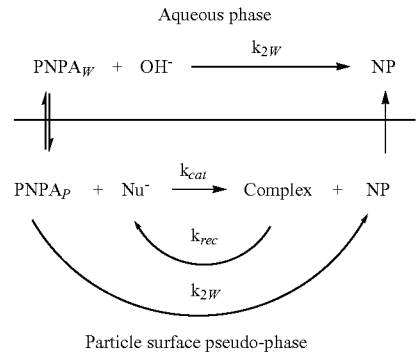

In the aqueous phase, PNPA undergoes spontaneous hydrolysis as described by Equation 8.

$$r_{bulk} = (k_{spon} + k_{OH}[OH^-]_{bulk})[PNPA]_{bulk} \quad (8)$$

Bulk concentrations refer to those in the aqueous phase. Given the certain degree of hydrophobic nature on the particle surface, PNPA substrate tended to distribute favorably on particle surface, enabling higher substrate concentration on particle surface than that in aqueous phase. Similar phenomena have been observed in absorption of hydrophobic proteins onto similar particles. PNPA was also observed to be favorably distributed into organic phase within the water/organic solvent mixture. On the particle surface where the functional groups were located, PNPA substrate underwent both the spontaneous hydrolysis and catalytic hydrolysis by amidoxime groups through the mechanism shown in Scheme 16. The decomposition reaction on the particle surface was therefore described by Equation 9.

$$r_{local} = (k_{spon} + k_{OH}[OH^-]_{local} + k_{cat}[NOH]_{local})[PNPA]_{local} \quad (9)$$

All concentrations in Equation 9 referred to those in the particle surface pseudo-phase. The overall concentration of hydrolyzed product, p-nitrophenol, was described by Equation 10.

$$\frac{d[PNP]_{overall}}{dt} = r_{bulk}\left(1 - \frac{V_{local}}{V_{total}}\right) + r_{local}\frac{V_{local}}{V_{total}} \quad (10)$$

in which $V_{local}$ is the volume of the particle phase and $V_{total}$ is the total volume, including both the aqueous phase and the particle phase. The following equations were to describe the relationship between concentrations in the bulk phase and those in the particle phase. As discussed above, PNPA was favorably distributed on the particle surface through Equation 11.

$$[PNPA]_{local} = K_S[PNPA]_{bulk} \quad (12)$$

in which $K_s$ is the distribution coefficient of PNPA between the two phases.

The averaged concentration of PNPA based on the overall system is defined according to Equation 12.)

$$(V_{total} - V_{local})[PNPA]_{bulk} + V_{local}[PNPA]_{local} = [PNPA]_{overall}V_{total} \quad (12)$$

Because the particle volume fraction was small, estimated to be 0.3% vol for 1 mg/mL particle dispersion, $V_{local}$ was neglected from the first term and Equation 12 was simplified to Equation 13.

$$[PNPA]_{bulk} = [PNPA]_{overall}/1 + K_S\beta \quad (13)$$

in which $$\beta = \frac{V_{local}}{V_{total}}$$

is the volume fraction of the particle phase. Furthermore, concentration relationship of hydroxide ions and catalytic groups were shown in Equation 14 and Equation 15 respectively.

$$[OH^-]_{local} = [OH^-]_{bulk} \quad (14)$$

$$[NOH]_{local} = \frac{V_{total}}{V_{local}}[NOH]_{overall} = 1/\beta[NOH]_{overall} \quad (15)$$

These concentration relationships were substituted into Equation 10 and further simplified to Equation 16.

$$\frac{d[PNP]_{overall}}{dt} = \left(k_{spon} + k_{OH}[OH^-] + \frac{k_{cat}[NOH]_{local}K_S\beta}{1 + K_S\beta}\right)[PNPA]_{overall} \quad (16)$$

For the particle concentration (less than 5 mg/mL) studied previously, particle volume fraction was less 1.5 percent. The distribution coefficient of PNPA between cumene and water is 100. Because hydrophobicity on the particle surface was much weaker than that of pure cumene, $K_s$ was much less than 100. As a result, $K_S\beta=1$. This enables further simplification of Equation 16 to Equation 17.

$$\frac{d[PNP]_{overall}}{dt} = (k_{spon} + k_{OH}[OH^-] + K_Sk_{cat}[NOH]_{average})[PNPA]_{overall} \quad (17)$$

The whole term in the parenthesis represents the observed kinetic constant of the PNPA hydrolysis catalyzed by amidoxime modified particles.

$$k_{obs} = k_{spon} + k_{OH}[OH^-] + K_Sk_{cat}[NOH]_{average} \quad (18)$$

Comparison with the hydrolysis catalyzed by homogenous amidoxime molecules shown in Equation 7 indicated a clear difference between the two systems. Slope of linear fitting of $k_{obs}$ plot against amidoxime concentration is $K_Sk_{cat}$ for the particle system and $k_{cat}$ for the homogenous system. The slope difference in FIG. 28 was the result of concentration effect of the substrate on the particle surface combined with the fact that functional groups were only located on the particle surface. This combined concentration effects resulted in the enhancement of reactivity in the particle system versus that in the homogenous system. If the substrate was further assumed to undergo the same reaction mechanism with the same second order kinetic constants in both cases, it is concluded that the surface concentration of PNPA substrate was about twice as that in the bulk solution. The absorption measurement has shown that presence of 5% wt particle solution reduced the bulk concentration of PNPA by about 10 percent. This supported the above model of preferred solubilization of PNPA on the particle surface.

Based on the analysis with a two-phase model, it is hypothesized that the enhancement is due to solubilization of the p-nitrophenol acetate within the polymeric coating of the particles.

Example 17

General Procedures for Examples 18-23

Having established the success of the modified particles in hydrolysis reactions of p-nitrophenol acetate as a model compound, in this example, the hydrolysis reaction of organophosphate compounds, such as diisopropyl fluorophosphate (DFP) and methyl- and ethyl-paraoxon, accelerated by α-nucleophiles, such as hydroxamic acid and pyridine-2-aldoxime methochloride (2-PAM), was measured in homogenous systems to understand the reaction mechanism. Effects on the reaction mechanism and reaction rates of the solution conditions, substrate properties, and the properties of nucleophiles were discussed. Secondly, the OP hydrolysis reaction by hydroxamic acid modified particles was investigated for their reactivity and recovery properties and potential applications were then discussed in such systems.

Diisopropyl fluorophosphates (DFP), ethyl-paraoxon, methyl-paraoxon, 3-(Cyclohexylamino)-1-propanesulfonic acid (CAPS), tris(hydroxymethyl)aminomethane (Trizma base), pyridine-2-aldoxime methochloride (2-PAM) and acetohydroxamic acid (98%) (AHA), and polyacrylamide (50% wt in water, Mw=10,000) were purchased from Sigma-Aldrich Chemical Company (Milwaukee, Wis.) and used as received. Dimethyl phosphate and diethyl phosphate (75% wt, balanced with phosphoric acid) were purchased from Acros Organics (Geel, Belgium). Sodium hydroxide was purchased from Mallinckrodt Baker Inc. (Phillipsburg, N.J.) and used as received. Water was obtained from the Milli-Q water system.

All organophosphate compounds are extremely toxic. Particular care was taken when handling these chemicals. Buffers at pH 8 and 9 were prepared with tris (hydroxymethyl) aminomethane (Trizma base). Buffer at pH 9.6 and 10.6 were prepared with CAPS. Polyhydroxamic acid (PHA) was prepared from polyacrylamide as described in the previous examples.

The hydrolysis mechanism of the organophosphate compounds was measured by phosphorus 31 nuclear magnetic resonance ($^{31}$P NMR). This technique can differentiate various phosphorus-containing species in the system and detect their concentration change to measure the hydrolysis kinetics. Solution mixtures consisted of nucleophilic compounds, 50 mM of buffer to keep solution pH constant, 5 mM of organophosphate compounds, and 20% vol of deuterium oxide serving as signal lock. The $^{31}$P NMR test was performed on a Varian 501 spectrometer (202 MHz for phosphorus). Longitudinal relaxation times, T1, of all organophosphate compounds were first determined to be less than 4 seconds under the same solution conditions as those in kinetic measurements. The delay time, d1, was therefore set to be 20 seconds to allow full relaxation of the phosphorus nuclei after the magnetic pulse for quantitative measurement of various phosphorus-containing species. Sixteen scans were collected to produce high-quality signal. The middle point of the collection time period was considered as the time point when the measurement was conducted. The acquired data then underwent Fourier transformation, phase correction, and baseline correction to obtain the final NMR spectra. Individual peaks in the spectra were integrated to calculate the relative concentrations of each phosphorus-containing component in the system and then analyze the hydrolysis mechanism and hydrolytic kinetics.

Example 18

Spontaneous Hydrolysis of OP Compounds

Spontaneous hydrolysis of methyl-paraoxon and ethyl-paraoxon were followed by both UV/Vis and $^{31}$P NMR. UV/Vis is technique measured only the reaction pathway of releasing p-nitrophenol, whereas $^{31}$P NMR analyzed all hydrolysis products.

Figure 33:
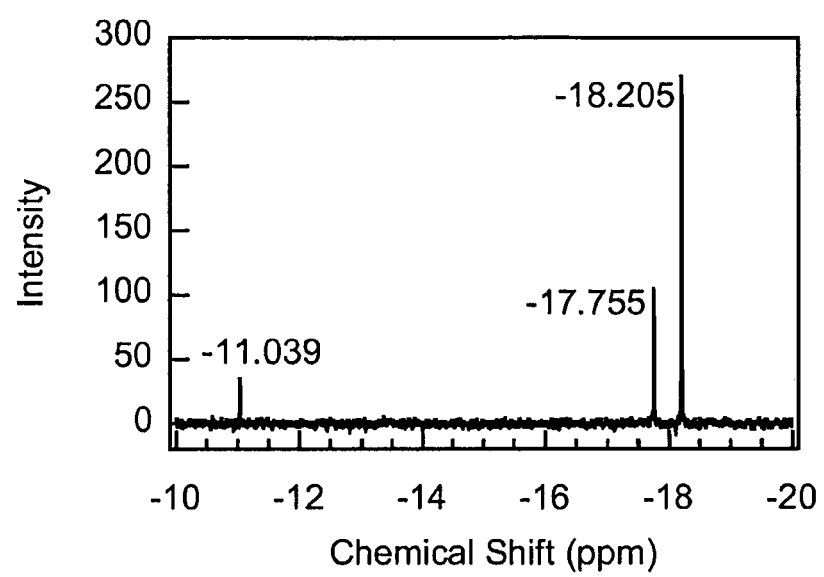
FIG. 33 depicts the NMR spectrum of hydrolytic system of 5 mM of methyl-paraoxon in 50 mM Tris buffer at pH 8 with 20% deuterium oxide as signal lock after 8670 min.

Methyl-paraoxon and ethyl-paraoxon underwent similar spontaneous hydrolysis. There were two types of hydrolysis products shown in the NMR spectrum for each substrate. The NMR spectrum of methyl-paraoxon system in 50 mM Tris buffer at pH 8 after 8670 min is shown in FIG. 33, in which chemical shift at −18.205 ppm was from methyl-paraoxon. Peak areas at the chemical shifts of −17.756 ppm and −11.040 ppm increased over time while the substrate peak gradually shrunk, indicating the presence of two hydrolytic products. NMR comparison with commercially available dimethyl phosphate under the same solution conditions suggested that the chemical shift at −11.040 ppm was from the product when hydroxyl groups substituted the p-nitrophenyl groups. It was then reasonably postulated that the chemical shift at −17.756 ppm was from the product when hydroxyl groups substitute the methoxide groups.

Figure 34:
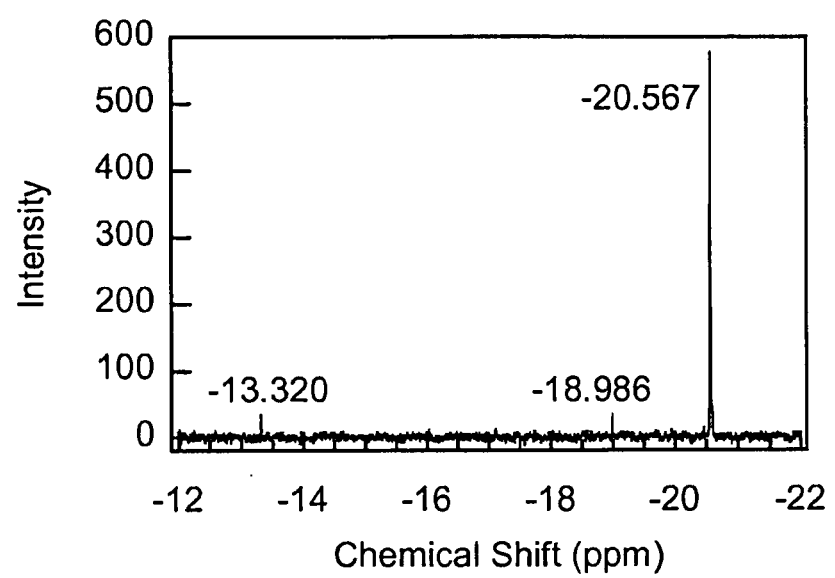
FIG. 34 depicts the NMR spectrum of hydrolytic system of paraoxon in 50 mM Tris buffer at pH 8 with 20% deuterium oxide as signal lock after 23 days.

Ethyl-paraoxon behaved similarly to methyl-paraoxon. As shown in FIG. 34, chemical shift at −20.534 ppm was from the original substrate whereas chemical shifts at −13.299 ppm and −18.985 ppm were from the two hydrolytic products when hydroxyl groups substitute the p-nitrophenol and ethoxide groups respectively in 50 mM Tris buffer at pH 8 after 23 days. Even after this long time, the majority of ethyl-paraoxon substrate still remained intact, indicating the environmental persistence of such substrates.

Nucleophiles can attack both the phosphorus and alkyl carbon atom of the organophosphate esters during the hydrolysis or ethanolysis reactions. The importance of these pathways depends on the properties of the substrate, nucleophiles and the solution conditions. The cleavage of the P—O bond of a chiral thiophosphonate substrate by phosphotriesterase (PTE) was shown to proceed through an $SN_2$-like single displacement reaction with a net inversion of the configuration at the phosphorus center. Fenitrothion was mainly subjected to $SN_2$ attack on phosphorus in alkaline systems.

Similarly, hydroxyl ions attacked both the methyl or ethyl groups and p-nitrophenol groups during the spontaneous hydrolysis of methyl-paraoxon and ethyl-paraoxon. In 50 mM Tris buffer solution at pH 8, the reaction on methyl groups was almost three times faster than that on p-nitrophenol groups for methyl-paraoxon, while the reaction on ethyl groups proceeded at the same rate as that on p-nitrophenol groups.

Measurement by UV/Vis is followed only the reaction mechanism releasing p-nitrophenol. The spontaneous hydrolysis of OP compounds within buffer solution is described in Equation 19, in which the total reaction rate included the substitution reaction on both phosphorus and carbon atoms.

$$r_{total} = (k_{spon} + k_{OH}[OH^-])[OP] = r_P + r_C \qquad (19)$$

Since the solution pH was kept constant with buffer, the hydroxyl concentration was constant and the hydrolysis was following pseudo first order kinetics. The hydrolysis kinetics of releasing p-nitrophenol was then integrated into Equation 20. The measured concentration change was then simplified based on this equation and the observed kinetic constants were obtained through the linear fitting of logarithmic term versus time plot for both mechanisms.

$$-\ln(1 - [PNP]/[OP]_0) = k_{obs}t \qquad (20)$$

Figure 35:
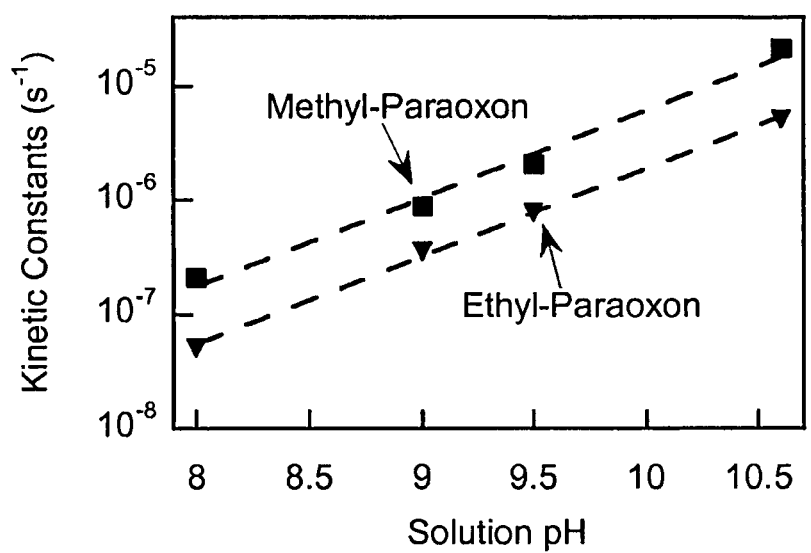
FIG. 35 depicts the dependence on solution pH of kinetic constants from spontaneous hydrolysis of methyl- and ethyl-paraoxon. 50 mM Tris buffer was used to keep solution pH at 8 and 9, and 50 mM CAPS buffer to keep solution pH at 9.5 and 10.6, respectively.

The kinetic constants are plotted against solution pH in FIG. 35 of the hydrolysis of methyl- and ethyl-paraoxon releasing p-nitrophenol. Hydrolysis of methyl-paraoxon was two to three times faster than that of ethyl-paraoxon at each solution pH, reflecting that the steric hindrance from the two ethoxide groups was much larger than that of the two methoxide groups during the second order nucleophilic substitution of hydroxyl on phosphorus. The kinetic constants were linearly dependent on solution pH with a slope of 0.8 on logarithmic scale. This suggested that the reaction is first order with respect to both hydroxyl ions and OP substrate. This is consistent with the claims in the literature that organophosphate triesters were hydrolyzed through the associative mechanism, in which the nucleophiles approached the substrates and formed a pentacoordinated transition state or transient intermediate prior to expelling leaving group. Reactions of nucleophiles with neutral OP species could proceed either through a two-step pathway involving a pentacoordinate intermediate or through a concerted one-step pathway when the pKa value of the leaving group was very small. During the measurement, we were not able to detect the presence of either the pentacoordinate intermediate or transition state in the NMR spectrum, indicating that the formation of intermediate or transition state was the rate-limiting and it was readily decomposed if it ever formed.

The NMR measurement was also used to calculate the kinetic constants. The peaks in the acquired NMR spectra were integrated and the relative percentage of each peak was calculated. The kinetic constants were obtained through the same procedure as that used in the UV/Vis is measurement. In Table 3 are shown the kinetic constants of the two mechanisms at different solution pH when methyl-paraoxon is hydrolyzed by hydroxyl ions. The kinetic constant of reaction on the p-nitrophenol groups increases almost 85 times with the increase of solution pH from 8 to 10.6. However, the kinetic constant of reaction of reaction on the methoxide groups only increases slightly at the same time. This indicates the reaction on the methoxide groups is first order and therefore following dissociative mechanism, where as the reaction on the p-nitrophenol groups is second order and following associative mechanism.

TABLE 3

Kinetic constants of methyl-paraoxon hydrolysis on the nitrophenol and alkyl groups respectively. 50 mM Tris buffer to keep solution pH at 8 and 50 mM CAPS buffer to keep solution pH at 10.

|  | Reaction on p-nitrophenol | Reaction on methoxide |
| --- | --- | --- |
| pH = 8 | $1.1 \times 10^{-7}\,s^{-1}$ | $4.2 \times 10^{-7}\,s^{-1}$ |
| pH = 10.6 | $9.3 \times 10^{-6}\,s^{-1}$ | $1.4 \times 10^{-6}\,s^{-1}$ |

Figure 36:
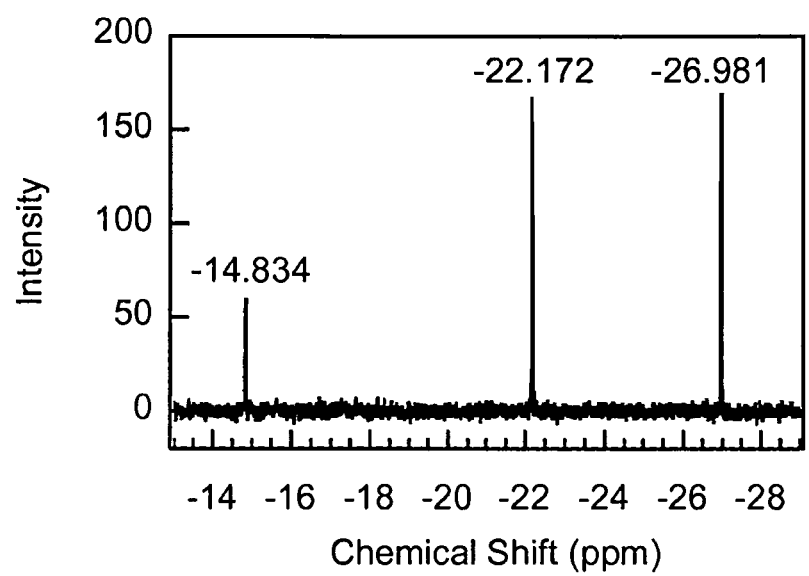
FIG. 36 depicts an NMR spectrum establishing the spontaneous hydrolysis of DFP in 50 mM Tris buffer at pH 8 after 292 min. 20% vol of deuterium oxide was added to lock the NMR signal.

The NMR spectrum of the diisopropyl fluorophosphate (DFP) hydrolysis system is shown in FIG. 36. The doublet occurring at −22.172 ppm and −26.981 ppm was from DFP substrate. There was only one product peak at −14.834 ppm. It was proposed in the literature that DFP forms a pentacoordinate intermediate with the attacking nucleophiles and the intermediate decomposes through fluoride ion leaving. The formation step was always rate-determining during hydrolysis in aqueous solution based on experimental results as well as ab initio molecular orbital calculations. The fact there was only one product peak throughout the process indicated that the pentacoordinate intermediate decomposed very fast and as a result the concentration of the intermediate was too low to be detected by $^{31}$P NMR. The strong dependence of hydrolysis rate on solution pH and pseudo-first order reaction kinetics at each constant pH kept constant suggested that the reaction is first order with regard to the substrate and hydroxyl ions. This is consistent with the pentacoordinate intermediate formation mechanism.

Hydrolysis rate of DFP was much faster that of the triesters under the same solution conditions. This is because the presence of fluoride pulls the electronic density away from the phosphorus atom and enables the phosphorus center to carry more positive charge characters and therefore more electrophilic. As a result, the substrate is more susceptible to the nucleophilic attack. Furthermore, fluoride ion is a much stronger leaving group than p-nitrophenol because of much smaller pKa. Therefore, the fluoride carrying substrates are more easily decomposed by attacking nucleophiles.

Example 19

Catalyst Turnover Test of 2-PAM and Acetohydroxamic Acid

Catalyst turnover is critical for the hydrolysis of organophosphate compounds when adding α-nucleophiles into the hydrolysis system. The turnover of α-nucleophiles, 2-PAM and acetohydroxamic acid (AHA) was investigated for the DFP hydrolysis with $^{31}$P NMR. The solution mixture consisted of 5 mM of DFP, 1 mM of 2-PAM or AHA, and 50 mM Tris buffer at pH 8. The mixture solution has 20% vol of deuterium oxide as signal lock. The solution mixture was then transferred into NMR tube and Varian 501 spectrometer was utilized to follow the hydrolytic kinetics. After following the initial decomposition of 20-30% of original DFP, the original OP compounds were allowed to be fully decomposed under the same conditions and the solution was kept at room temperature for another ten days to ensure any intermediates fully decomposed. Then another batch of pure DFP was added into the solution mixture to make the DFP concentration at 5 mM. The hydrolytic kinetics of DFP was measured again by NMR spectrometer. The kinetic constants acquired from the second NMR measurement were compared with those from the first to understand the catalyst turnover.

Example 20

Reaction of Methyl-Paraoxon, Paraoxon, and DFP with Oximes

Hydrolysis of the OP substrates by α-nucleophiles was also studied with the $^{31}$P NMR and UV/Vis is.

Figure 37:
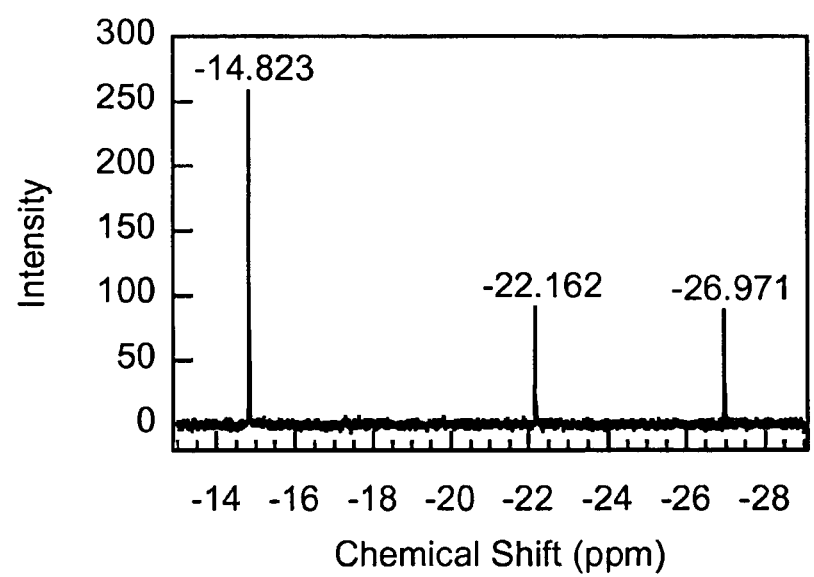
FIG. 37 depicts the NMR spectrum of DFP hydrolysis by 3 mM of 2-pyridinealdoxime methyl chloride (2-PAM) at 79 min in 50 mM Tris buffer at pH 8.

The NMR spectrum of the reaction mixture consisting of 5 mM of DFP and 3 mM of 2-PAM is shown in FIG. 37. There was only one product peak in addition to the doublet from DFP substrate. It was located at −14.823 ppm, the same position as that from the spontaneous hydrolysis.

The turnover of added nucleophiles after the first batch of reaction was studied in the case of DFP hydrolysis by 2-PAM. As described in Example 19, the recovered 2-PAM reacted with another batch of DFP substrate and the concentration change obtained through $^{31}$P NMR. The DFP hydrolysis by 2-PAM is described in Equation 21, $$r = \frac{d[DFP]}{dt} = -(k_{spon} + k_{OH}[\text{OH}^-] + k_{cat}[\text{NOH}^-])[DFP] \quad (21)$$

in which DFP is hydrolyzed through the spontaneous hydrolysis as well as hydrolysis by 2-PAM. The concentration change of the added 2-PAM is described in Equation 22.

$$\frac{d[\text{NOH}^-]}{dt} = -k_{cat}[\text{NOH}^-][\text{DFP}] + k_{rec}[\text{OH}^-][\text{Complex}] \quad (22)$$

in which the added 2-PAM was consumed by the reaction with DFP and recovered from the presumably formed complex. The above equation may not reflect the true reaction mechanism; rather it was used to test if 2-PAM can regenerate from the formed complex in the reaction mixture.

Figure 38:
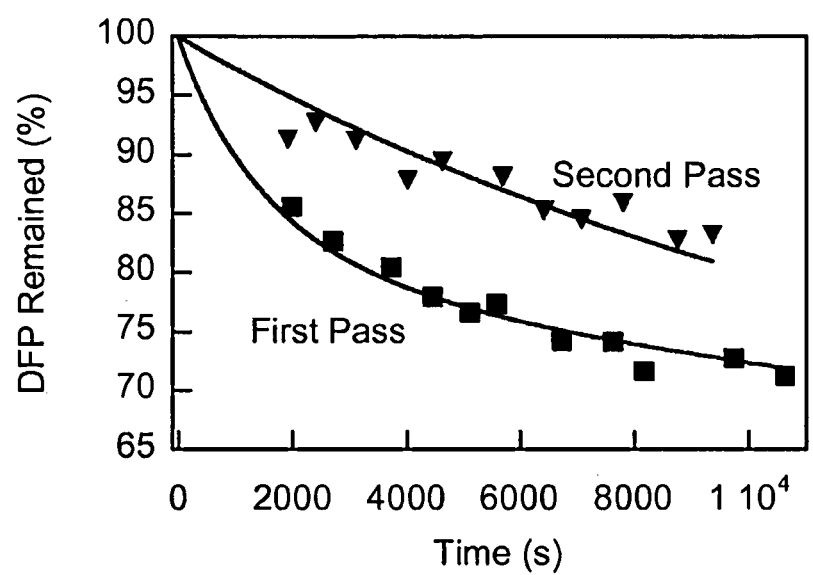
FIG. 38 depicts the DFP concentration change with pyridine-2-aldoxime methochloride (2-PAM) added. The first pass refers to the DFP hydrolysis with fresh 2-PAM and the second pass refers to another 5 mM of DFP added after the system has been fully hydrolyzed in 10 days. The lines were from the non-linear least square with the kinetic equations.

The spontaneous hydrolysis was measured separately under the same experimental conditions without the addition of 2-PAM to provide $k_{spon}+k_{OH}[\text{OH}^-]$ to be $9.8 \times 10^{-6} s^{-1}$. The turnover rate was further assumed to be slow and turnover term in Equation 22 was neglected. The second order kinetic constant $k_{cat}$ was then obtained through non-linear least square fitting through MATLAB calculation with the concentration change of DFP measured from $^{31}$P NMR. The experimental data and the fitting results are shown in FIG. 38.

The $k_{cat}$ obtained in the first pass was $0.13 M^{-1}s^{-1}$, reflecting the strong reactivity of 2-PAM toward the DFP hydrolysis. However, the $k_{cat}$ obtained through the same procedure was only $0.018 M^{-1}s^{-1}$ when DFP was again hydrolyzed in the system after the hydrolysis of excessive amount of DFP in the first pass. This indicates that either only a small amount of 2-PAM was recovered after reaction with excessive amount of DFP or the system accelerated DFP hydrolysis a little bit without any 2-PAM recovered. Either of these two scenarios suggests that 2-PAM was functioning more like a reactant than a catalyst for the DFP hydrolysis system.

Figure 39:
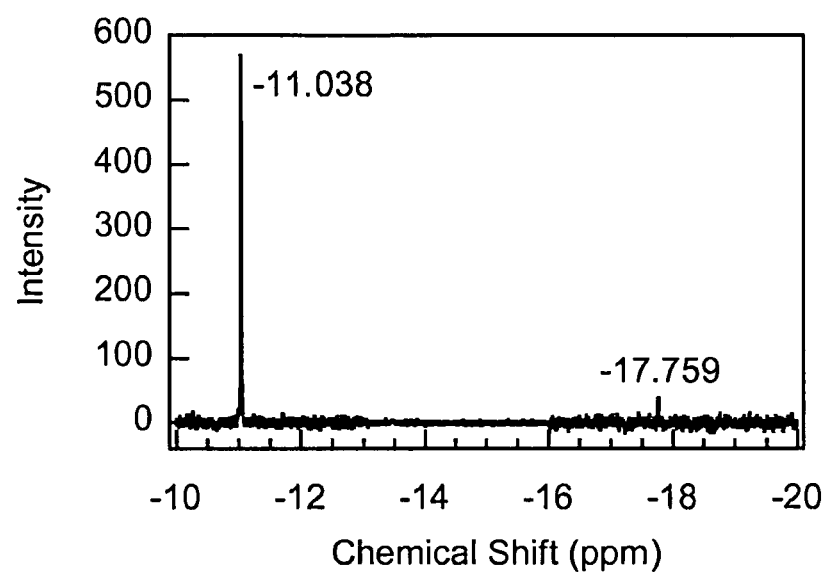
FIG. 39 depicts an NMR spectrum establishing methyl-paraoxon hydrolysis with 10 mM PAM-Cl in 50 mM Tris buffer at pH 8 after 3240 min.
Figure 40:
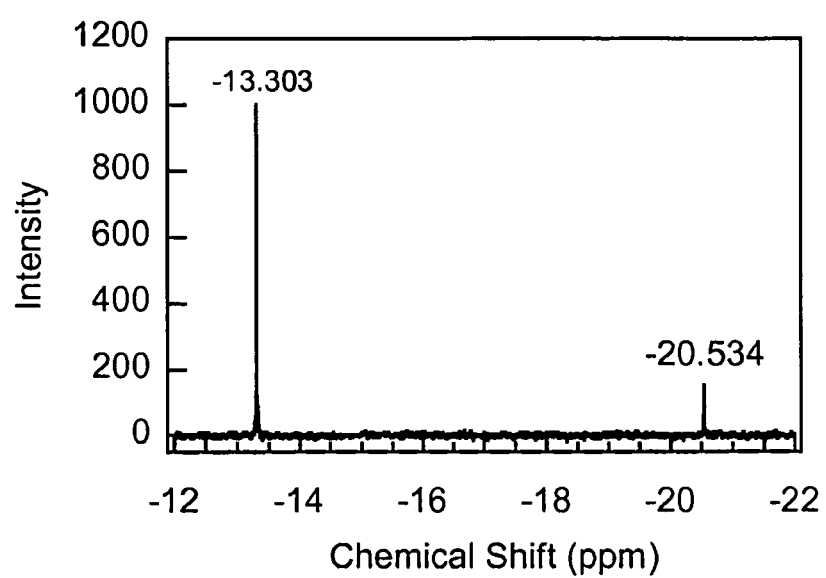
FIG. 40 depicts an NMR spectrum establishing paraoxon hydrolysis in 10 mM PAM-Cl in 50 mM Tris buffer at pH 8 after 3840 min.

Methyl-paraoxon and ethyl-paraoxon hydrolyzed by 2-PAM generated the products with the same chemical shifts as those from the spontaneous hydrolysis under the same solution conditions, as shown in FIG. 39 and FIG. 40, respectively.

During DFP hydrolysis, 2-PAM substituted the fluoride ions. For hydrolysis of methyl-paraoxon and ethyl-paraoxon, 2-PAM substituted the p-nitrophenol groups. It has been determined in the literature that oximes and OP compounds formed phosphoryl oxime intermediates, also strong inhibitors of AChEs. Therefore, dimethyl-, diethyl-, and diisopropyl-phosphoryl oxime were formed between OP substrates and 2-PAM as a result. The reaction is first order with regard to both the substrate and 2-PAM.

The diethyl-phosphoryl 2-PAM (DEP-2PAM) was prepared in organic solvent and tested to have a half-life of only 10 seconds in 10 mM Tris buffer (pH 7.8) at 29° C. The instability of phosphoryl 2-PAM was echoed in other literature findings. Therefore, the formed dimethyl-, diethyl, and diisopropyl-phosphoryl oximes from 2-PAM and methyl-paraoxon, ethyl-paraoxon, and DFP would be also very unstable because of the structural similarity with those in the literatures.

Furthermore, it was shown that the phosphonyl oxime intermediates formed between pyridinium oximes, obidoxime chloride (LuH6) and trimedoxime bromide (TMB4), had significantly different chemical shifts from the final organophosphoric acid measured by $^{31}$P NMR. The product formed during hydrolysis of the three organophosphates, however, had the same chemical shifts as the products from the spontaneous hydrolysis. Therefore, the generated products from the 2-PAM reactions were the same organophosphoric acids as those from the spontaneous hydrolysis. The phosphoryl oximes were not detected by $^{31}$P NMR if ever formed during the hydrolysis reaction due to the instability.

It has been shown that the phosphoryl oxime intermediates underwent two parallel decomposition pathways: Beckmann elimination pathway to form organophosphoric acid and transform the oxime groups into nitrile groups and $SN_2P$ substitution by hydroxide ions to yield organophosphoric acid and recovered oximes. The stability and decomposition pathway of the phosphoryl oximes are determined by the characteristics of the substitute groups on the phosphorus center, the structure of the oxime groups, and the solution conditions. When the other two substitute groups on the phosphorus center were alkoxide groups in the phosphoryl pyridinealdoximes, the elimination mechanism was dominant. When the two substitute groups were alkyl groups, the substitution mechanism was dominant and oxime groups were almost fully regenerated. When the two substitute groups consisted of one alkyl group and one alkoxide group, both mechanisms were functioning and the parent oxime was partially regenerated. O-isopropyl methylfluorophosphonyl 2-PAM formed by sarin and 2-PAM in water underwent the elimination reaction catalyzed by hydroxide ions and oximate ions, producing as end product 2-cyano-1-methylpyridinium cation. Dimethylphosphoryl-, diethylphosphoryl-, and diisopropylphosphoryl-obidoxime conjugates were decomposed by hydroxyl ions to yield obidoxime mononitrile confirmed by mass spectrometry.

The reaction mechanism of the organophosphate decomposition by 2-PAM is summarized in Scheme 19.

Figure 41:
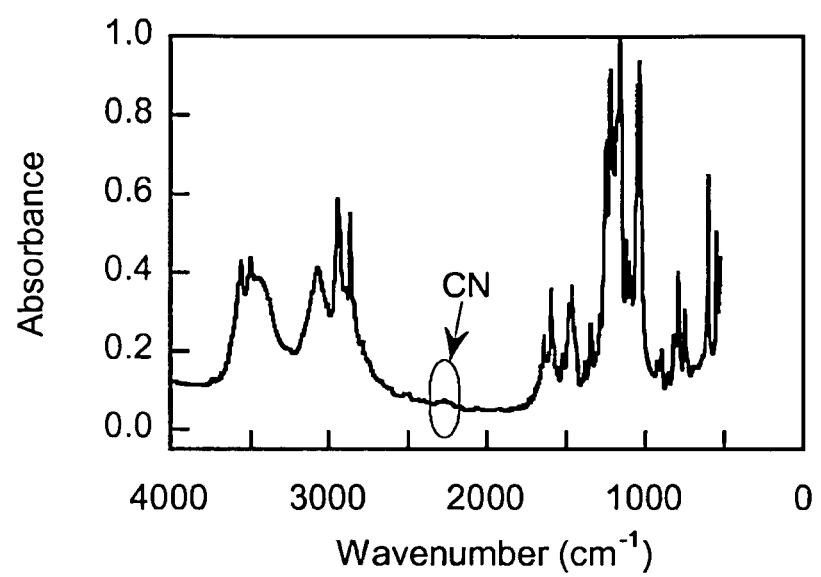
FIG. 41 depicts an FTIR spectrum of reaction mixture of 5 mM methyl-paraoxon at pH=10 after lypholization. Peak at 2267 cm$^{-1}$ indicated the presence of nitrile groups.

The final mixture of methyl-paraoxon hydrolyzed by 2-PAM was dried under vacuum and then analyzed by FT-IR to detect change of chemical bonds. As shown in FIG. 41, the reaction mixture from 2-PAM hydrolyzed methyl-paraoxon has a clear absorption peak at $2267 cm^{-1}$, a characteristic peak of nitrile groups. This indicated that phosphoryl 2-PAM was converted into the corresponding nitrile.

Scheme 19. Organophosphate decomposition of methyl-paraoxon by 2-PAM to form unstable intermediate dimethyl phosphoryl oxime and then the fast rearrangement to yield the final products.

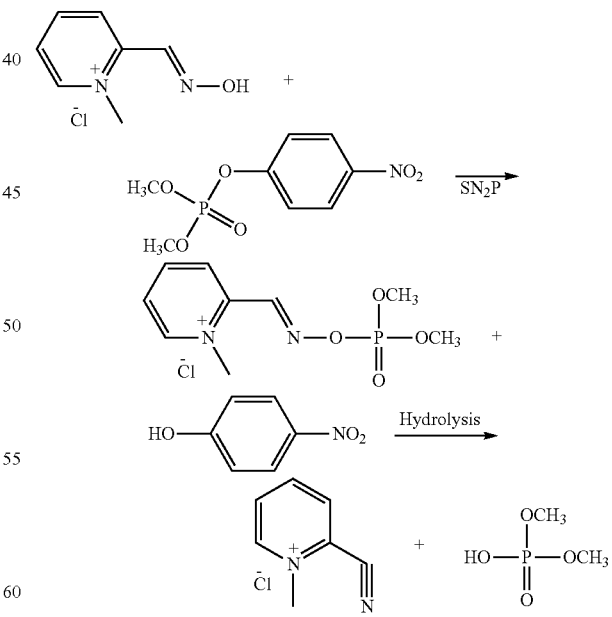

As the reaction mechanism and the recovery experiment suggested, 2-PAM added into the system was not functioning as a real catalyst. It was consumed stoichiometrically during the hydrolysis reaction to yield the nitrile product irreversibly. This also suggests that the fluoride ions from the first pass rather than the regenerated 2-PAM caused the faster DFP hydrolysis in the second pass of the recovery experiment than the spontaneous hydrolysis.

Example 21

Organophosphate Hydrolysis by Hydroxamic Acid

Figure 42:
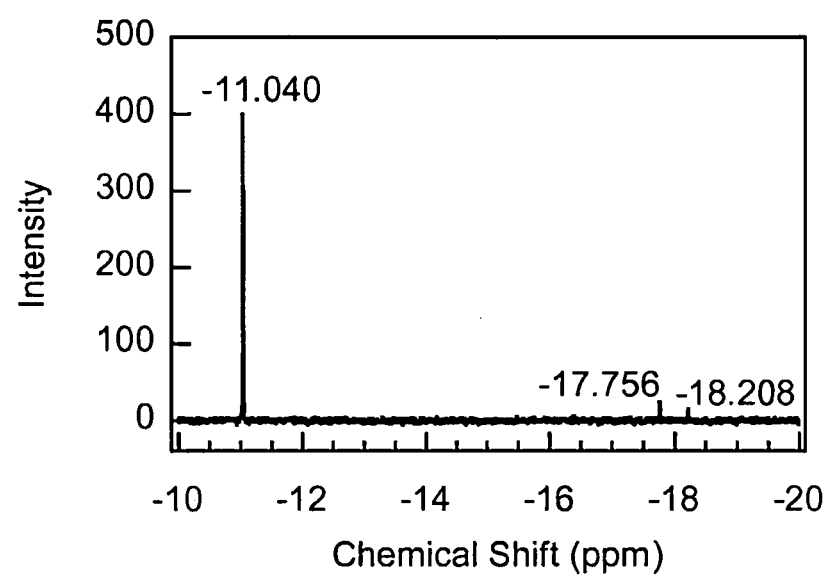
FIG. 42 depicts an NMR spectrum establishing methyl-paraoxon hydrolysis in 20 mM acetohydroxamic acid in 50 mM Iris buffer at pH 8 after 4115 min.
Figure 43:
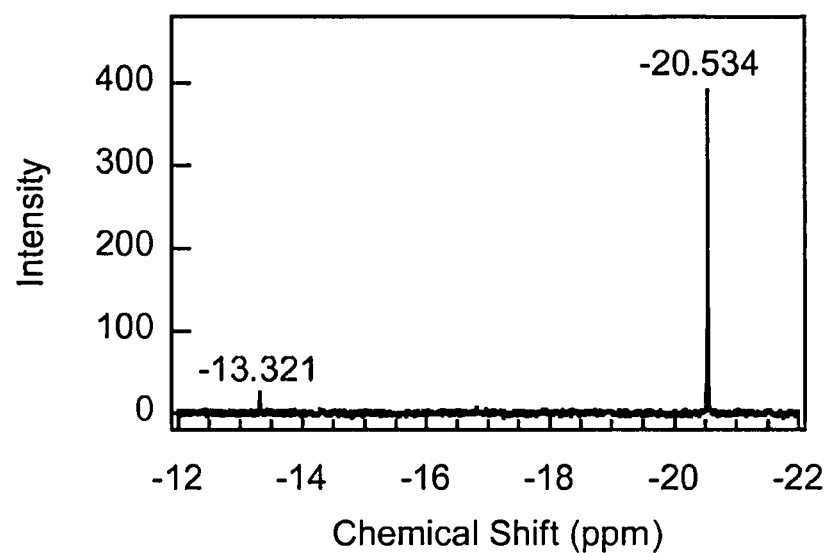
FIG. 43 depicts an NMR spectrum establishing paraoxon hydrolysis with 1 mM acetohydroxamic acid in 50 mM CAPS buffer at pH 9.5 after 182 min.

Decomposition of methyl-paraoxon and ethyl-paraoxon by acetohydroxamic acid yielded products with the same chemical shifts as those from the spontaneous hydrolysis under the same solution conditions, as shown in FIG. 42 and FIG. 43 respectively. Similar to 2-PAM, peaks at −11.040 ppm and −13.321 ppm grew much faster than those in spontaneous hydrolysis for methyl-paraoxon and ethyl-paraoxon respectively. These were products when the hydroxamic acid groups attacked the p-nitrophenol groups through nucleophilic substitution.

Figure 44:
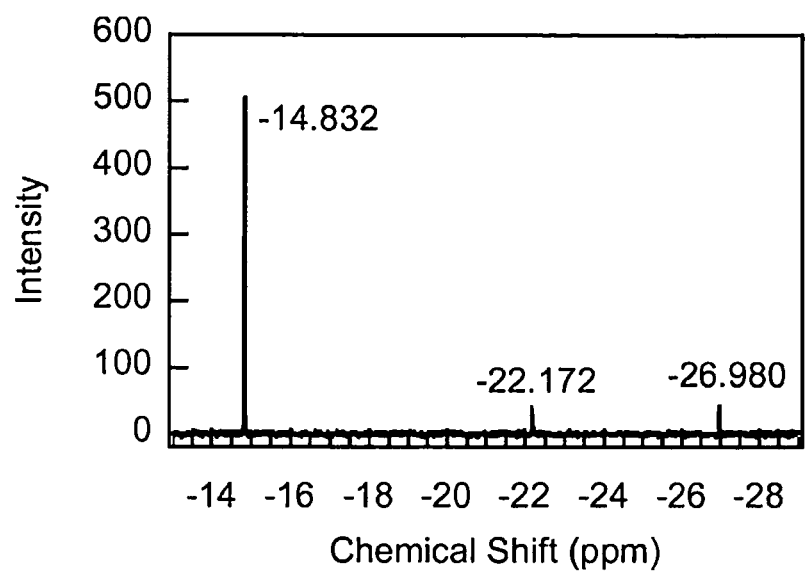
FIG. 44 depicts the NMR spectrum of 5 mM of DFP hydrolyzed by 20 mM acetohydroxamic acid at 140 min in 50 mM Tris buffer at pH 8.

The NMR spectrum of the reaction mixtures consisting of 5 mM of DFP and 20 mM acetohydroxamic acid in 50 mM Tris buffer at pH 8 is shown in FIG. 44. The only product also has the same chemical shift as that from the spontaneous hydrolysis.

Methyl-paraoxon and paraoxon hydrolyzed by hydroxamic acid nucleophiles were proposed to form phosphoryl hydroxamic acid intermediates through substituting the p-nitrophenol groups, as shown in Scheme 20.

Scheme 20. Proposed mechanism of paraoxon hydrolysis by hydroxamic acid groups to yield the phosphoryl hydroxamic acid and p-nitrophenol.

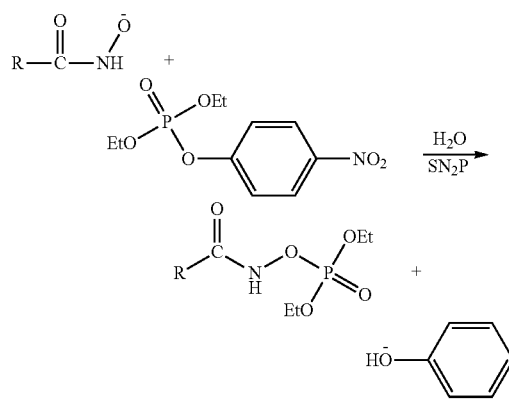

DFP hydrolyzed by hydroxamic acid nucleophiles was proposed to form the phosphoryl hydroxamic acid through nucleophilic substitution, as shown in Scheme 21.

Scheme 21. Proposed mechanism of DFP hydrolysis by hydroxamic acid groups to yield the hydrolyzed product and the phosphoryl hydroxamic acid intermediate

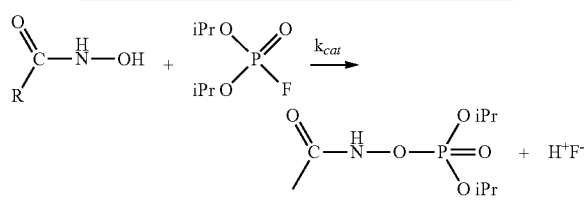

However, presence of these intermediates was not detected with $^{31}$P NMR during the hydrolysis of methyl-paraoxon, ethyl-paraoxon, and DFP by acetohydroxamic acid as well as poly-hydroxamic acid. The only products generated from the hydrolysis systems were dimethyl, diethyl, and diisopropyl phosphoric acid, the same ones from the spontaneous hydrolysis. This indicates that the phosphoryl hydroxamic acid intermediates were very unstable and they degenerated into the organophosphoric acid.

When hydroxamic acids were mixed with organophosphates at neutral solution conditions, such as diisopropyl fluorophosphate (DFP) and O-isopropyl methylfluorophosphonate (Sarin), hydroxamic acids were quickly phosphorylated to form highly unstable phosphoryl hydroxamic acid intermediate. Addition of more than thirty types of hydroxamic acid significantly accelerated Sarin and DFP hydrolysis. The strong electron-withdrawing capability of the phosphoryl groups from the P—O double bond increased the tendency of positive charge on nitrogen and therefore facilitated the migration of the alkyl group to undergo Lossen rearrangement. Therefore, phosphoryl hydroxamic acids rearranged extremely rapidly in a basic milieu and cannot be isolated. The rearrangement was also facilitated as the electron-releasing power of the substitute group on hydroxamic acid increased. This intermediate underwent the Lossen rearrangement to give the organophosphoric acid and isocyanate. The isocyanate group then reacted with the hydroxamic acid to yield the stable final product, O-alkylcarbamoyl alkylhydroxamate.

The rearrangement mechanism of diisopropylphosphoryl hydroxamic acid intermediate is summarized in Scheme 22. This mechanism also applies to the hydrolysis of methyl-paraoxon and ethyl-paraoxon by hydroxamic acid due to the similar chemical structures.

Scheme 22. Rearrangement mechanism of the phosphoryl hydroxamic acid

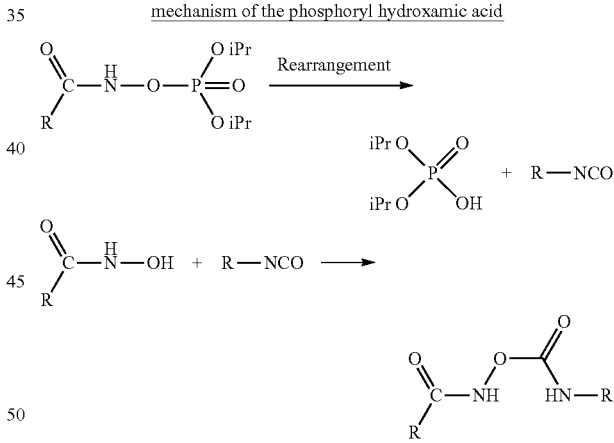

Example 22

Organophosphate Decomposition by Hydroxamic Acid Modified Magnetic Nanoparticles Hydrolytic kinetics of methyl-paraoxon and ethyl-paraoxon by the hydroxamic acid modified particles was measured by following the concentration change of hydrolyzed product, p-nitrophenol ion. The reaction mixture consisted of magnetic particles, 50 mM Tris buffer to keep solution pH at 9, 0.2 M sodium chloride to keep the ionic strength constant, and 0.25 mM of organophosphate compounds. At certain time intervals, 0.5 mL of the reaction mixture was drawn out and passed through HGMS column to remove the particles. The HGMS procedure was the same as that in earlier examples. Hewlett-Packard 8453 UV/Vis is spectrophotometer was utilized to measure the absorbance of the collected solution. Absorbance at 404 nm was from the p-nitrophenol ion and used to calculate the concentration of hydrolyzed product and then the hydrolysis rate. Spontaneous hydrolysis was also measured with UV/Vis is for methyl-paraoxon and ethyl-paraoxon at the same solution conditions with 0.05 mM substrate.

Hydroxamic acid modified magnetic particles were prepared through the procedure described in chapter 3 and they were much more effective against the hydrolysis of p-nitrophenyl acetate than amidoxime modified particles based on the same particle weight.

The particles were tested against the hydrolysis of methyl-paraoxon and ethyl-paraoxon. As previously discussed, nucleophilic groups attack the p-nitrophenol groups and yield dimethyl- and diethyl phosphate. The reaction kinetics was followed by UV/Vis is to measure the hydrolyzed product, p-nitrophenol ion, at the absorbance of 404 nm. The nucleophilic substitution reaction is first order with respect to the organophosphate substrate and the nucleophiles. The overall hydrolysis reaction including the spontaneous hydrolysis and hydrolysis by hydroxyl ions is described in Equation 23.

$$r = \frac{d[NP]}{dt} = (k_{spon} + k_{OH}[OH^-] + k_{cat}[NOH^-])[OP] = r_{spon} + r_{cat} \quad (23)$$

Since the substrates added into the system were 0.5 mM and effective amount of hydroxamic acid groups added was 1 mM, the concentration of nucleophiles remained roughly constant during the initial stage of the hydrolysis reaction. The solution pH was kept constant at 9 with 50 mM Tris buffer and the first two terms remained constant over the whole hydrolysis process. Therefore, the initial stage of the reaction follows pseudo-first order reaction kinetics and the above equation can be integrated into Equation 24.

$$-\ln(1-[PNP]/[OP]_0) = k_{obs}t \quad (24)$$

in which the observed kinetic constant included both spontaneous hydrolysis and hydrolysis by added nucleophiles, as shown in Equation 25.

$$k_{obs} = k_{spon} + k_{OH}[OH^-] + k_{cat}[NOH^-] \quad (25)$$

Figure 45:
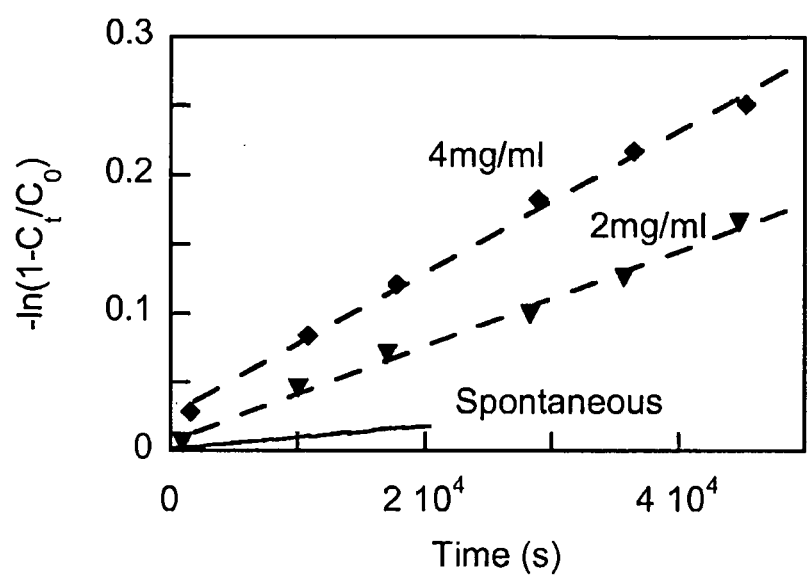
FIG. 45 depicts the pseudo-first order hydrolytic kinetics of methyl-paraoxon with addition of various particle concentration from spontaneous hydrolysis, hydrolysis with 2 mg/mL and 4 mg/mL hydroxamic acid functionalized particles. Solution pH was kept at 9 with 50 mM Tris buffer and 25° C. [Methyl-Paraoxon]$_0$=0.5 mM.
Figure 46:
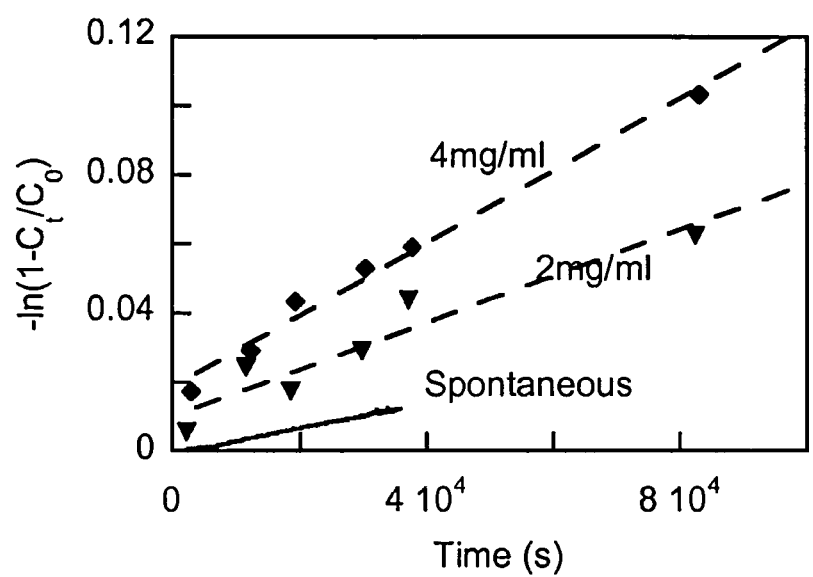
FIG. 46 depicts the pseudo-first order hydrolysis kinetics of ethyl-paraoxon with addition of various particle concentration from spontaneous hydrolysis, hydrolysis with 2 mg/mL and 4 mg/mL hydroxamic acid functionalized particles. Solution pH was kept at 9 with 50 mM Tris buffer and 25° C. [Ethyl-Paraoxon]$_0$=0.5 mM.

The obtained concentration change of p-nitrophenol was then transformed according to the Equation 24. The data points at various times were fitted with a linear function and the fitting slope was the observed kinetic constant for the nucleophilic hydrolysis. The hydrolysis reactions of methyl-paraoxon and ethyl-paraoxon by hydroxamic acid modified particles are shown in FIG. 45 and FIG. 46, respectively.

Based on the linear fitting results, the systems have shown clear pseudo-first order kinetics during the initial stage. The addition of hydroxamic acid modified particles significantly increased the hydrolysis rate of methyl-paraoxon and ethyl-paraoxon.

The obtained kinetic constants were then plotted against the particle concentration. The results for the hydrolysis of methyl-paraoxon (a) and ethyl-paraoxon (b) are shown in FIG. 47. The kinetic constants increased linearly with the increase of particle concentration, indicating that there were no inter-particle interactions to affect the hydrolytic capability of the hydroxamic acid groups on the particle surface.

The homogenous hydrolysis of methyl-paraoxon and ethyl-paraoxon accelerated by acetohydroxamic acid and polyhydroxamic acid was also measured with the UV/Vis technique. The kinetic constants for the OP hydrolysis were obtained through the same procedure as done previously with the modified particles. The second order kinetic constants of these nucleophiles are listed in Table 4 and Table 5 for methyl-paraoxon and ethyl-paraoxon, respectively. These results showed that the monomeric acetohydroxamic acid was much more reactive against the OP hydrolysis than both the polyhydroxamic acid and the modified particles due to the steric hindrance from the polymer chains. 2 mg/mL particle dispersion had similar kinetic constants as 1 mM PHA against both substrates, consistent with the result from PNPA hydrolysis as well.

The substrate structures affect also significantly on the hydrolysis enhancement. Since the two ethyl groups have more steric hindrance toward the incoming nucleophiles than the methyl groups, paraoxon hydrolysis by nucleophiles was much slower than the methyl-paraoxon hydrolysis. The comparison between AHA and PHA has shown that the reactivity differences between these two nucleophiles are 4, 14, and 17 against the hydrolysis of p-nitrophenyl acetate, methyl-paraoxon, and ethyl-paraoxon respectively. This suggests that the steric hindrance from the substrate decrease the accessibility of the phosphorus center for the polymeric form more than that for the monomeric form.

TABLE 4

Second order kinetic constants of hydrolysis of methyl-paraoxon by hydroxamic acid nucleophiles at pH 9

| Nucleophiles | Second order kinetic constant |
|---|---|
| Acetohydroxamic acid (AHA) | $2.5 \times 10^{-5}$ mM$^{-1}$s$^{-1}$ |
| Polyhydroxamic acid (PHA) | $1.8 \times 10^{-6}$ mM$^{-1}$s$^{-1}$ |
| Hydroxamic acid modified particles | $1.1 \times 10^{-6}$ (mg/mL)$^{-1}$s$^{-1}$ |

TABLE 5

Second order kinetic constants of hydrolysis of ethyl-paraoxon by hydroxamic acid nucleophiles at pH 9

| Nucleophiles | Second order kinetic constant |
|---|---|
| Acetohydroxamic acid (AHA) | $7.5 \times 10^{-6}$ mM$^{-1}$s$^{-1}$ |
| Polyhydroxamic acid (PHA) | $4.4 \times 10^{-7}$ mM$^{-1}$s$^{-1}$ |
| Hydroxamic acid modified particles | $1.8 \times 10^{-7}$ (mg/mL)$^{-1}$s$^{-1}$ |

Example 23

Catalyst Recovery and Stability of Magnetic Nanoparticles

After the magnetic particles reacted with the first batch of OP substrates and were recovered by HGMS, they were readily washed out of the column with water. They were then used for the hydrolysis reaction of another batch of OP substrates. Unfortunately, no reaction acceleration was observed for the hydrolysis of either methyl-paraoxon or ethyl-paraoxon from the hydroxamic acid modified particles. This is due to the fact that the phosphoryl hydroxamic acid groups underwent Lossen rearrangement to form the stable alkylcarbamoyl hydroxamate, which were not converted back to the original hydroxamic acid groups under the solution conditions. However, due to the presence of strong surface changes from sulfonic acid groups during the particle synthesis, the particles maintained the excellent colloidal stability even after the hydroxamic acid groups were consumed as a result of the decomposition.

It has been shown that the Lossen rearrangement would be significantly reduced if the proton attached with the nitrogen atom in the hydroxamic acid groups was substituted with alkyl groups because of the lone electron pair of nitrogen would not be available for Lossen rearrangement. However, this substitution would significantly reduce the nucleophilicity of the hydroxamic acid group and therefore its reactivity toward the hydrolysis of carboxyl and phosphorus esters due to the steric hindrance introduced by the added alkyl groups.
Incorporation by Reference All of the U.S. patents and U.S. patent application publications cited herein are hereby incorporated by reference.
Equivalents Those skilled in the art will recognize, or be able to ascertain using no more than routine experimentation, many equivalents to the specific embodiments of the invention described herein. Such equivalents are intended to be encompassed by the following claims.

We claim:

1. A composition, comprising a substrate, a cluster, and a reactive group, wherein
the cluster comprises ceria, silica, titania, or an iron oxide;
the reactive group comprises an oximate, an iodosobenzoate, an iodoxybenzoate, an amidooxime, a hydroxamate, an imidazole, an amine, a peroxide, a guanidine, a nucleophile, an oxidant, or a bactericide;
a bond connects the cluster to the substrate; and
a linker connects the cluster to the reactive group or a second bond connects the cluster to the reactive group.

2. The composition of claim 1, wherein the substrate is a polymer having pendant hydroxyl, carboxylate, or amino groups.

3. The composition of claim 1, wherein the substrate is a polysaccharide, cellulose or poly(vinyl alcohol).

4. The composition of claim 1, wherein the bond is a coordination bond metal-organic, a covalent bond, a hydrogen bond or an ionic bond.

5. The composition of claim 1, wherein the second bond is a coordination bond metal-organic, a covalent bond, a hydrogen bond or an ionic bond.

6. The composition of claim 1, wherein the cluster is ceria, silica, titania or an iron oxide.

7. The composition of claim 1, wherein the substrate is a polymer having pendant hydroxyl, carboxylate, or amino groups; and the bond is a bond from the oxygen of the pendant hydroxyl, an oxygen of the pendant carboxylate, or the nitrogen of the pendant amino, to a cerium atom, a silicon atom, a titanium atom, or an iron atom in the cluster.

8. The composition of claim 1, wherein the linker is a bond or is represented by $B^1$—Y—Z—$B^2$; wherein $B^1$ is a bond to the cluster; Y is alkylene; Z is absent, —O—, —N(H)—, —S—, —C(=O)O—, —C(=O)N(H)—, —OC(=O)O—, —OC(=O)N(H)—, —N(H)C(=O)O—, —N(H)C(=O)N(H)—, —C(=O)S—, —S(=O)—, —S(=O)$_2$—, —C(=O)—, —C(=NH)—, —C(=S)—, or —C(=O)N(H) N(H)—; and $B^2$ is a bond to the reactive group.

9. The composition of claim 1, wherein the reactive group is chlorhexidine; and said chlorhexidine is bonded to the linker through one of its amines.

10. The composition of claim 1, wherein the cluster is silica; and the tether-reactive group is

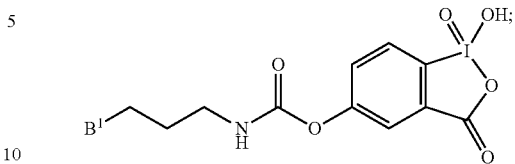

and $B^1$ is a bond to a silicon atom in the cluster.

11. A composition, comprising a substrate, a cluster, and a reactive group, wherein
the cluster comprises ceria, silica, titania, or an iron oxide;
the reactive group comprises an oximate, an iodosobenzoate, an iodoxybenzoate, an amidooxime, a hydroxamate, an imidazole, an amine, a peroxide, a guanidine, a nucleophile, an oxidant, or a bactericide;
a bond connects the cluster to the substrate; and
a linker connects the substrate to the reactive group.

12. The composition of claim 11, wherein the substrate is a polymer having pendant hydroxyl, carboxylate, or amino groups.

13. The composition of claim 11, wherein the substrate is an acrylic acid-vinylsulfonic acid, 4-styrenesulfonic acid copolymer.

14. The composition of claim 13, wherein the substrate further comprises 10-undecenoic acid.

15. The composition of claim 11, wherein the cluster is ceria, silica, titania, or an iron oxide.

16. The composition of claim 11, wherein the substrate is a polymer having pendant hydroxyl, carboxylate, or amino groups; and the bond is a bond from the oxygen of the pendant hydroxyl, an oxygen of the pendant carboxylate, or the nitrogen of the pendant amino, to a cerium atom, a silicon atom, a titanium atom, or an iron atom in the cluster.

17. The composition of claim 11, wherein the linker is a bond or is represented by $B^1$—Y—Z—$B^2$; wherein $B^1$ is a bond to the reactive group; Y is alkylene; Z is absent, —O—, —N(H)—, —S—, —C(=O)O—, —C(=O)N(H)—, —OC(=O)O—, —OC(=O)N(H)—, —N(H)C(=O)O—, —N(H)C(=O)N(H)—, —C(=O)S—, —S(=O)—, —S(=O)$_2$—, —C(=O)—, —C(=NH)—, —C(=S)—, or —C(=O)N(H)N(H)—; and $B^2$ is a bond to the substrate.

18. The composition of claim 11, wherein the reactive group is chlorhexidine; and said chlorhexidine is bonded to the linker through one of its amines.

19. A method of making a modified substrate,
comprising the step of reacting under sol-gel conditions a substrate with pendant hydroxyl or amino groups with a compound comprising a cluster tethered via a tether to a reactive group; or
comprising the step of reacting a substrate with pendant hydroxyl or amino groups with a ceria, silica, titania, or an iron oxide, thereby forming a cluster bonded to said substrate;
and reacting said cluster with a compound having a reactive group, thereby tethering the reactive group to the cluster via a tether,
wherein
the cluster comprises ceria, silica, titania, or an iron oxide;
the reactive group comprises an oximate, an iodosobenzoate, an iodoxybenzoate, an amidooxime, a hydroxamate, an imidazole, an amine, a peroxide, a guanidine, a nucleophile, an oxidant, or a bactericide.

20. A method for the hydrolysis of a compound which contains at least one oxidized phosphorus group or killing a bacterium, comprising the step of contacting said compound or said bacterium with a composition for sufficient time to hydrolyze at least some of the oxidized phosphorus groups in said compound or to kill the bacterium, wherein said composition comprises a substrate, a cluster, and a reactive group;

the cluster comprises ceria, silica, titania, or an iron oxide;

the reactive group comprises an oximate, an iodosobenzoate, an iodoxybenzoate, an amidooxime, a hydroxamate, an imidazole, an amine, a peroxide, a guanidine, a nucleophile, an oxidant, or a bactericide;

a bond connects the cluster to the substrate; and a linker connects the cluster to the reactive group, a second bond connects the cluster to the reactive group, or a linker connects the substrate to the reactive group.

* * * * *